US010208035B2

(12) United States Patent
Zhao et al.

(10) Patent No.: US 10,208,035 B2
(45) Date of Patent: Feb. 19, 2019

(54) COMPOUNDS FOR INHIBITING DRUG-RESISTANT STRAINS OF HIV-1 INTEGRASE

(71) Applicant: The United States of America, as represented by the Secretary, Department of Health and Human Services, Washington, DC (US)

(72) Inventors: Xue Zhi Zhao, Frederick, MD (US); Steven Smith, Thurmont, MD (US); Mathieu Metifiot, Saint Andre de Cubzac (FR); Barry Johnson, Chincoteague, VA (US); Christophe Marchand, Silver Spring, MD (US); Stephen H. Hughes, Smithsburg, MD (US); Yves Pommier, Bethesda, MD (US); Terrence R. Burke, Jr., Bethesda, MD (US)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 19 days.

(21) Appl. No.: 15/589,590

(22) Filed: May 8, 2017

(65) Prior Publication Data
US 2017/0305904 A1    Oct. 26, 2017

Related U.S. Application Data

(62) Division of application No. 14/891,309, filed as application No. PCT/US2014/037905 on May 13, 2014, now Pat. No. 9,676,771.

(60) Provisional application No. 61/824,306, filed on May 16, 2013, provisional application No. 61/899,061, filed on Nov. 1, 2013.

(51) Int. Cl.
| C07D 471/04 | (2006.01) |
| A61K 31/4375 | (2006.01) |
| A61K 45/06 | (2006.01) |
| A61K 31/4704 | (2006.01) |
| A61K 31/496 | (2006.01) |
| A61K 31/5377 | (2006.01) |
| C07D 215/58 | (2006.01) |
| C07D 215/60 | (2006.01) |
| C07D 491/147 | (2006.01) |

(52) U.S. Cl.
CPC ........ *C07D 471/04* (2013.01); *A61K 31/4375* (2013.01); *A61K 31/4704* (2013.01); *A61K 31/496* (2013.01); *A61K 31/5377* (2013.01); *A61K 45/06* (2013.01); *C07D 215/58* (2013.01); *C07D 215/60* (2013.01); *C07D 491/147* (2013.01)

(58) Field of Classification Search
None
See application file for complete search history.

(56) References Cited

U.S. PATENT DOCUMENTS

| 2004/0044207 A1 | 3/2004 | Anthony et al. |
| 2010/0056516 A1 | 3/2010 | Williams et al. |

(Continued)

FOREIGN PATENT DOCUMENTS

| WO | WO 2008/010964 | 1/2008 |
| WO | WO 2008/014307 | 1/2008 |
| WO | WO 2013/016441 | 1/2013 |

OTHER PUBLICATIONS

Geretti et al., "Emerging patterns and implications of HIV-1 integrase inhibitor resistance," *Curr. Opin. Infect. Dis.*, 25(6): 677-686, Dec. 2012. (Abstract only).

(Continued)

*Primary Examiner* — Bong-Sook Baek
(74) *Attorney, Agent, or Firm* — Klarquist Sparkman, LLP

(57) ABSTRACT

A method of inhibiting drug-resistant HIV-1 integrase in a subject comprising administering to a subject in need thereof a therapeutically effective amount of a compound of formula I, or a pharmaceutically acceptable salt or ester thereof, having a structure of:

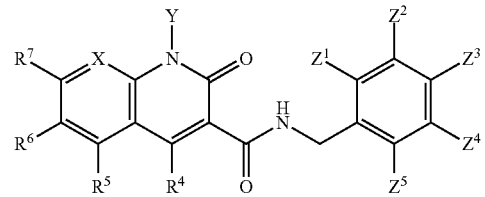

wherein X is N, C(OH), or CH;
Y is H or OH;
each of $Z^1$-$Z^5$ is independently H or halogen;
$R^4$ is H, OH, $NH_2$, $NHR^8$, $NR^8R^9$ or $R^8$;
$R^5$, $R^6$, and $R^7$ is each independently H, halogen, $OR^8$, $R^8$, $NHR^8$, $NR^8R^9$, $CO_2R^8$, $CONR^8R^9$, $SO_2NR^8R^9$, or $R^5$ and $R^6$ together with the carbon atoms to which $R^5$ and $R^6$ are attached form an optionally-substituted carbocycle or optionally-substituted heterocycle; and
$R^8$ and $R^9$ is each independently H, optionally-substituted alkyl, optionally-substituted alkenyl, optionally-substituted alkynyl, optionally-substituted aryl, optionally-substituted cycloalkyl, optionally-substituted cycloalkylene, optionally-substituted heterocycle, optionally-substituted amide, optionally-substituted ester, or $R^8$ and $R^9$ together with the nitrogen to which $R^8$ and $R^9$ are attached form an optionally-substituted heterocycle.

21 Claims, 3 Drawing Sheets

(56) References Cited

U.S. PATENT DOCUMENTS

| | | |
|---|---|---|
| 2010/0056563 A1 | 3/2010 | Guiadeen et al. |
| 2012/0053205 A1 | 3/2012 | Kuhnert et al. |
| 2012/0115900 A1 | 5/2012 | Brown et al. |
| 2013/0096109 A1 | 4/2013 | Hattori et al. |
| 2013/0217693 A1 | 8/2013 | Danter et al. |

OTHER PUBLICATIONS

International Search Report issued in International Application No. PCT/US2014/037905 dated Aug. 4, 2014, 5 pages.

Johnson et al., "Design and synthesis of novel N-hydroxy-dihydronaphthyridinones as potent and orally bioavailable HIV-1 integrase inhibitors," *J. Med. Chem.*, 54(9): 3393-3417, Mar. 29, 2011.

Kawasuji et al., "Carbamoyl pyridine HIV-1 integrase inhibitors. 1. Molecular design and establishment of an advanced two-metal binding pharmacophore," *J. Med. Chem.*, 55(20): 8735-8744, Sep. 10, 2012. (Abstract only).

Liao et al., "Authentic HIV-1 integrase inhibitors," *Future Med. Chem*, 2(7): 1107-1122, Jul. 12, 2010.

Marchand et al., "HIV-1 inhibitors: 2010 update and perspectives," *Curr Top Med Chem*, 9(11): 1016-1037, Apr. 28, 2010.

Metifiot et al., "Resistance to Integrase Inhibitors," *Viruses*, 2(7): 1347-1367, Jun. 25, 2010.

Mospanova et al., "Search for new analgesics among 4-hydroxy-6,7-dimethoxy-2-oxo-1,2-dihydroquinoline-3-carboxylic acid benzylamides," *Zhurnal Organichnoi Ta FarmatSevtichnoi Khimii*, 10(2): 50-53, 2012. (Full Russian text with English abstract).

Quashie et al., "Novel therapeutic strategies targeting HIV integrase," *BMC Medicine*, 10(34): 1-11, 2012.

Sabbah et al., "Biological evaluation and docking studies of recently identified inhibitors of phosphoinositide-3-kinases," *Bioorganic & Medical Chemistry Letters*, 22(2): 876-880, Jan. 15, 2012.

Sabbah et al., "N-Phenyl-4-hydroxy-2-quinolone-3-carboxamides as selective inhibitors of mutant H1047R phosphoinositide-3-kinase (PI3K[alpha])," *Bioorganic & Medicinal Chemistry*, 20(24): 7175-7183, Dec. 1, 2012.

Su et al., "Structural Basis for the Inhibition of RNase H Activity of HIV-1 Reverse Transcriptase by RNase H Active Site-Directed Inhibitors" *Journal of Virology*, pp. 7625-7633, 2010. (full text in EIR).

Summa et al., "Discovery of raltegravir, a potent, selective orally bioavailable HIV-integrase inhibitor for the treatment of HIV-AIDS infection," *J. Med. Chem.*, 51(18): 5843-5855, Sep. 3, 2008.

Williams et al., "Potent and selective HIV-1 ribonuclease H inhibotors based on a 1-hydroxy-1, 8-naphthyridin-2(1H)-one scaffold," *Bioorganic & Medicinal Chemistry Letters*, 20(22), 6754-6757, Nov. 15, 2010.

Zhao et al., "4-Amino-1-hydroxy-2-oxo-1, 8-naphthyridine-containing compounds having high potency against raltegravir-resistant integrase mutants of HIV-1," *Journal of Medicinal Chemistry*, 57(12): 5190-5202, Jun. 26, 2014.

Zhao et al., "Bicyclic 1-Hydroxy-2-oxo-1, 2-dihydropyridine-3-carboxamide-Containing HIV-1 Integrase Inhibitors Having High Antiviral Potency Against Cells Harboring Raltegravir-Resistant Integrase Mutants," *Journal of Medicinal Chemistry*, 57(4): 1573-1582, Feb. 27, 2014.

COMPOUNDS FOR INHIBITING DRUG-RESISTANT STRAINS OF HIV-1 INTEGRASE

This application is a divisional of U.S. application Ser. No. 14/891,309, filed Nov. 13, 2015, which is the U.S. National Stage of International Application No. PCT/US2014/037548, filed May 13, 2014, which was published in English under PCT Article 21(2), which in turn claims the benefit of U.S. Provisional Appl. No. 61/824,306, filed May 16, 2013, and U.S. Provisional Appl. No. 61/899,061, filed Nov. 1, 2013. Both of the provisional applications are incorporated herein by reference.

BACKGROUND

Although there are currently two FDA-approved HIV integrase inhibitors on the market (raltegravir and elvitegravir), both show a low to moderate genetic barrier to resistance and extensive cross-resistance, increasing the need for inhibitors with improved efficacy against raltegravir-resistant strains.

SUMMARY

Disclosed herein is a method of inhibiting drug-resistant HIV-1 integrase in a subject comprising administering to a subject in need thereof a therapeutically effective amount of a compound of formula I, or a pharmaceutically acceptable salt or ester thereof, having a structure of:

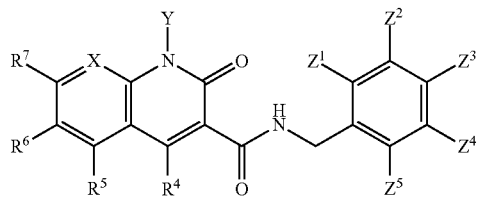

wherein X is N, C(OH), or CH;
Y is H or OH;
each of $Z^1$-$Z^5$ is independently H or halogen;
$R^4$ is H, OH, $NH_2$, $NHR^8$, $NR^8R^9$ or $R^8$;
$R^5$, $R^6$, and $R^7$ is each independently H, halogen, $OR^8$, $R^8$, $NHR^8$, $NR^8R^9$, $CO_2R^8$, $CONR^8R^9$, $SO_2NR^8R^9$, or $R^5$ and $R^6$ together with the carbon atoms to which $R^5$ and $R^6$ are attached form an optionally-substituted carbocycle or optionally-substituted heterocycle; and
$R^8$ and $R^9$ is each independently H, optionally-substituted alkyl, optionally-substituted alkenyl, optionally-substituted alkynyl, optionally-substituted aryl, optionally-substituted cycloalkyl, optionally-substituted cycloalkylene, optionally-substituted heterocycle, optionally-substituted amide, optionally-substituted ester, or $R^8$ and $R^9$ together with the nitrogen to which $R^8$ and $R^9$ are attached form an optionally-substituted heterocycle.

Also disclosed herein is a compound of formula IV, or a pharmaceutically acceptable salt or ester thereof, having a structure of:

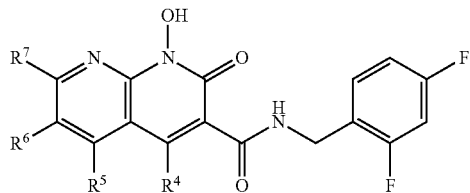

wherein $R^4$ is H, OH, $NH_2$, $NHR^8$, or $NR^8R^9$;
$R^5$, $R^6$, and $R^7$ is each independently H, $OR^8$, $R^8$, $NHR^8$, $NR^8R^9$, $CO_2R^8$, $SO_2NR^8R^9$, or $R^5$ and $R^6$ together with the carbon atoms to which $R^5$ and $R^6$ are attached form an optionally-substituted carbocycle or optionally-substituted heterocycle; and
$R^8$ and $R^9$ is each independently H, optionally-substituted alkyl, optionally-substituted alkylene, optionally-substituted aryl, optionally-substituted cycloalkyl, optionally-substituted cycloalkylene, optionally-substituted heterocycle, optionally-substituted amide, optionally-substituted ester, or $R^8$ and $R^9$ together with the nitrogen to which $R^8$ and $R^9$ are attached form an optionally-substituted heterocycle.

Further disclosed herein is a compound of formula V, or a pharmaceutically acceptable salt or ester thereof, having a structure of:

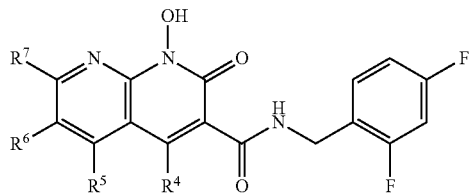

wherein $R^5$ and $R^7$ are each H;
$R^4$ is H, OH, $NH_2$, $NHR^8$, $NR^8R^9$ or $R^8$;
$R^8$ and $R^9$ is each independently H, optionally-substituted alkyl, optionally-substituted alkylene, optionally-substituted aryl, optionally-substituted cycloalkyl, optionally-substituted cycloalkylene, optionally-substituted heterocycle, optionally-substituted amide, optionally-substituted ester, or $R^8$ and $R^9$ together with the nitrogen to which $R^8$ and $R^9$ are attached form an optionally-substituted heterocycles; and
$R^6$ is substituted alkyl, halogen, optionally substituted aryl, amino, ester, sulfonate, or substituted sulfonyl.

Also disclosed herein is a compound of formula VI, or a pharmaceutically acceptable salt or ester thereof, having a structure of:

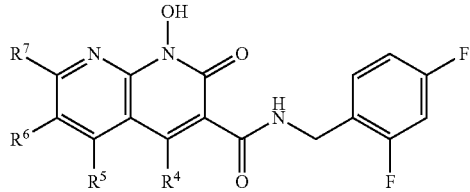

wherein $R^5$ and $R^7$ are each H;
$R^4$ is H, OH, $NH_2$, $NHR^8$, $NR^8R^9$ or $R^8$;
$R^8$ and $R^9$ is each independently H, optionally-substituted alkyl, optionally-substituted alkylene, optionally-substituted aryl, optionally-substituted cycloalkyl, optionally-substituted cycloalkylene, optionally-substituted heterocycle, optionally-substituted amide, optionally-substituted ester, or $R^8$ and $R^9$ together with the nitrogen to which $R^8$ and $R^9$ are attached form an optionally-substituted heterocycles; and $R^6$ is a substituent that interacts with amino acid residues Thr122, Ser 119, Gly118, Pro142, Tyr143 that are present in a cavity of HIV-1 integrase.

Further disclosed herein is a method for inhibiting the integration of HIV-1 integrase, comprising contacting HIV-1 integrase with a compound that interacts with amino acid residues Thr122, Ser 119, Gly118, Pro142, Tyr143 that are present in a cavity of the HIV-1 integrase.

Additionally disclosed herein is a method of treating HIV in a subject comprising administering to a subject in need thereof a therapeutically effective amount of a compound of formula V or VI.

Further disclosed herein is a method of preventing HIV infection in a subject administering to a subject in need thereof a therapeutically effective amount of a compound of formula V or VI.

Additionally disclosed herein is a method of inhibiting drug-resistant HIV-1 integrase in a subject comprising administering to a subject in need thereof a therapeutically effective amount of a compound of formula V or VI.

DETAILED DESCRIPTION

Terminology

Figure 1:
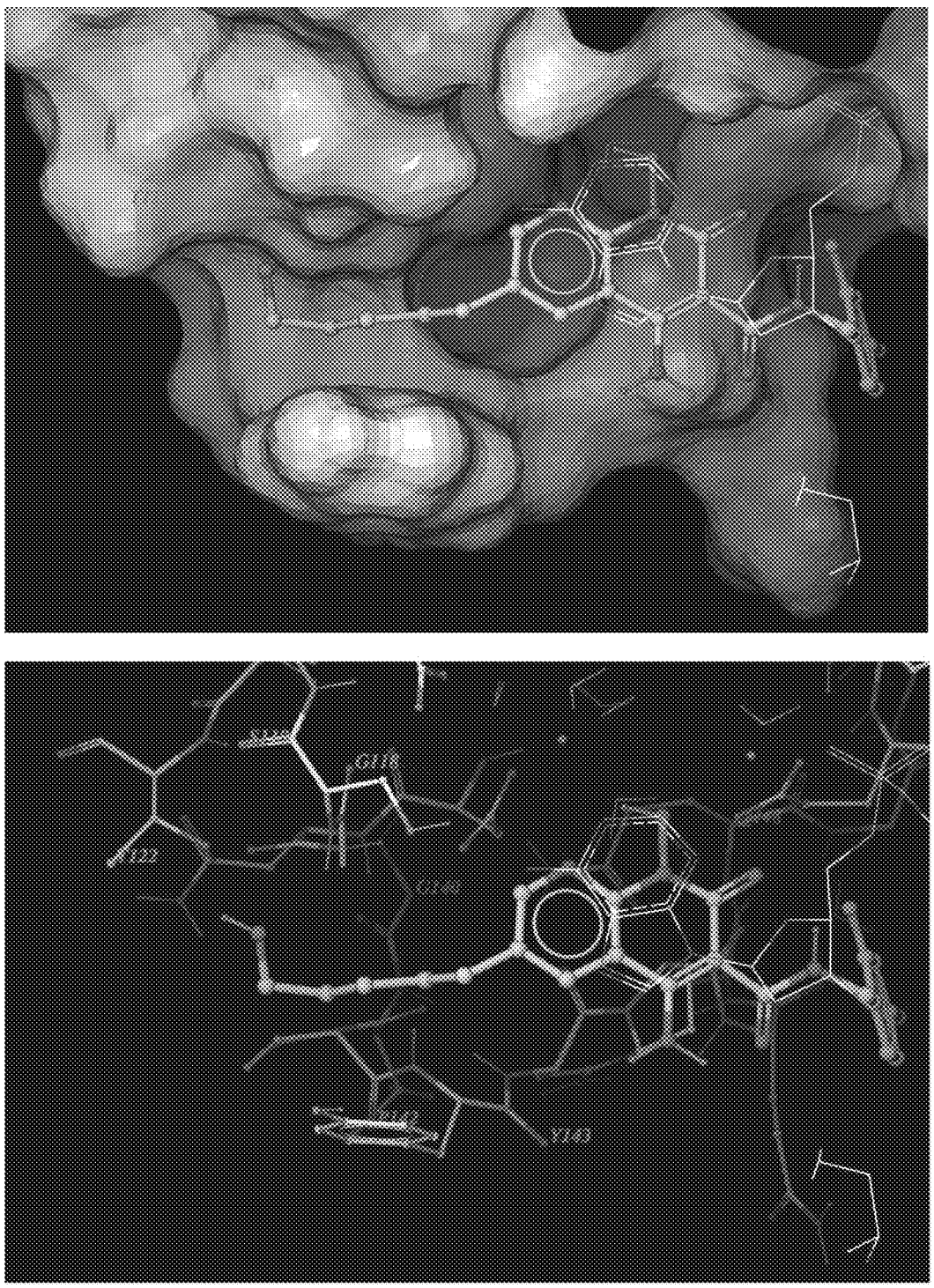
FIG. 1. Docking of XZ419 in a homology model of HIV-1 IN derived from the co-crystal dolutegravir (DTG) bound to the PFV IN along with DNA substrate using Molsoft ICM software.

As used herein, the singular terms "a," "an," and "the" include plural referents unless context clearly indicates otherwise. Also, as used herein, the term "comprises" means "includes."

Although methods and materials similar or equivalent to those described herein can be used in the practice or testing of the present disclosure, suitable methods and materials are described below. In addition, the materials, methods, and examples are illustrative only and not intended to be limiting.

To facilitate review of the various examples of this disclosure, the following explanations of specific terms are provided:

"Acyl" refers to a group having the structure —C(O)R, where R may be, for example, optionally substituted alkyl, optionally substituted aryl, or optionally substituted heteroaryl. "Lower acyl" groups are those that contain one to six carbon atoms.

"Acyloxy" refers to a group having the structure —OC(O)R—, where R may be, for example, optionally substituted alkyl, optionally substituted aryl, or optionally substituted heteroaryl. "Lower acyloxy" groups contain one to six carbon atoms.

"Administration" as used herein is inclusive of administration by another person to the subject or self-administration by the subject.

The term "aliphatic" is defined as including alkyl, alkenyl, alkynyl, halogenated alkyl and cycloalkyl groups. A "lower aliphatic" group is a branched or unbranched aliphatic group having from 1 to 10 carbon atoms.

"Alkanediyl," "cycloalkanediyl," "aryldiyl," "alkanearyldiyl" refers to a divalent radical derived from aliphatic, cycloaliphatic, aryl, and alkanearyl hydrocarbons.

"Alkenyl" refers to a cyclic, branched or straight chain group containing only carbon and hydrogen, and contains one or more double bonds that may or may not be conjugated. Alkenyl groups may be unsubstituted or substituted. "Lower alkenyl" groups contain one to six carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, isobutoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$ alkanoyl can be acetyl, propanoyl or butanoyl; halo$(C_1-C_6)$ alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy; thioalkyl can be -alkyl-SH or -alkyl-alkylthio.

"Alkynyl" refers to a cyclic, branched or straight chain group containing only carbon and hydrogen, and contains one or more triple bonds. Alkynyl groups may be unsubstituted or substituted. "Lower alkynyl" groups are those that contain one to six carbon atoms.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group. For example, an "alkylamino" or "alkylated amino" refers to —NRR', wherein at least one of R or R' is an alkyl.

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H). A suitable aminocarbonyl group is acetamido.

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Aryl" refers to a monovalent unsaturated aromatic carbocyclic group having a single ring (e.g., phenyl) or multiple condensed rings (e.g., naphthyl or anthryl), which can optionally be unsubstituted or substituted. A "heteroaryl group," is defined as an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

The term "aralkyl" refers to an alkyl group wherein an aryl group is substituted for a hydrogen of the alkyl group. An example of an aralkyl group is a benzyl group.

"Aryloxy" or "heteroaryloxy" refers to a group of the formula —OAr, wherein Ar is an aryl group or a heteroaryl group, respectively.

The term "carbocycle" refers to a cyclic structure that only includes carbon atoms as part of the core ring structure. Carbocycle is inclusive, for example, of cycloalkyl, cycloalkenyl, and aryl. In certain embodiments, the carbocycle has 3, 4, 5, 6, 7 or 8 ring carbon atoms.

The term "carboxylate" or "carboxyl" refers to the group —COO or —COOH.

The term "co-administration" or "co-administering" refers to administration of a HIV-1 integrase inhibitor disclosed herein with at least one other therapeutic agent, preferably another anti-HIV agent, within the same general time period, and does not require administration at the same exact moment in time (although co-administration is inclusive of administering at the same exact moment in time). Thus, co-administration may be on the same day or on different days, or in the same week or in different weeks. The additional therapeutic agent may be included in the same composition, or different composition, as the HIV-1 integrase inhibitor. In certain embodiments, "co-administration" or "co-administering" is inclusive of administering a compound disclosed herein with at least one anti-HIV agent as component of a combination antiretroviral therapy or highly active antiretroviral therapy (HAART).

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "ester" refers to a carboxyl group having the hydrogen replaced with, for example, a $C_{1-6}$alkyl group ("carboxyl$C_{1-6}$alkyl" or "alkylester"), an aryl or aralkyl group ("arylester" or "aralkylester") and so on. $CO_2C_{1-3}$alkyl groups are preferred, such as for example, methylester ($CO_2Me$), ethylester ($CO_2Et$) and propylester ($CO_2Pr$) and includes reverse esters thereof (e.g. —OCOMe, —OCOEt and —OCOPr).

The term "halogen" refers to fluoro, bromo, chloro and iodo substituents.

The terms 'halogenated alkyl" or "haloalkyl group" refer to an alkyl group as defined above with one or more hydrogen atoms present on these groups substituted with a halogen (F, Cl, Br, I).

The term "hydroxyl" is represented by the formula —OH.

"Inhibiting" refers to inhibiting the full development of a disease or condition. "Inhibiting" also refers to any quantitative or qualitative reduction in biological activity or binding, relative to a control.

"N-heterocyclic" or "N-heterocycle" refers to mono or bicyclic rings or ring systems that include at least one nitrogen heteroatom. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as pyrrolyl rings.

Examples of 5-membered monocyclic N-heterocycles include pyrrolyl, H-pyrrolyl, pyrrolinyl, pyrrolidinyl, oxazolyl, oxadiazolyl, (including 1,2,3 and 1,2,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), and dithiazolyl. Examples of 6-membered monocyclic N-heterocycles include pyridyl, pyrimidinyl, pyridazinyl, pyrazinyl, piperidinyl, morpholinyl, thiomorpholinyl, piperazinyl, and triazinyl. The heterocycles may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. The N-heterocyclic group may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, indolyl, isoindolyl, benzoxazolyl, benzothiazolyl, benzisoxazolyl, benzisothiazolyl, benzimidazolyl, indazolyl, isoquinolinyl, quinolinyl, quinoxalinyl, purinyl, cinnolinyl, phthalazinyl, quinazolinyl, quinoxalinyl, benzotriazinyl, and the like. These heterocycles may be optionally substituted, for example with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. Unless otherwise defined optionally substituted N-heterocyclics includes pyridinium salts and the N-oxide form of suitable ring nitrogens.

"Nitro" refers to an R-group having the structure —$NO_2$.

An "R-group" or "substituent" refers to a single atom (for example, a halogen atom) or a group of two or more atoms that are covalently bonded to each other, which are covalently bonded to an atom or atoms in a molecule to satisfy the valency requirements of the atom or atoms of the molecule, typically in place of a hydrogen atom. Examples of R-groups/substituents include alkyl groups, hydroxyl groups, alkoxy groups, acyloxy groups, mercapto groups, and aryl groups.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Substituted" or "substitution" refer to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

The term "sulfonyl" refers to the group —$SO_2H$.

The term "substituted sulfonyl" refers to a sulfonyl group having the hydrogen replaced with, for example a $C_{1-6}$alkyl group ("sulfonyl$C_{1-6}$alkyl"), an aryl ("arylsulfonyl"), an aralkyl ("aralkylsulfonyl") and so on. Sulfonyl$C_{1-3}$alkyl groups are preferred, such as for example, —$SO_2Me$, —$SO_2Et$ and —$SO_2Pr$.

The term "sulfonate" refers to the group $SO_3H$ and includes groups having the hydrogen replaced with, for example a $C_{1-6}$alkyl group ("alkylsulfonate"), an aryl ("arylsulfonate"), an aralkyl ("aralkylsulfonate") and so on. $C_{1-3}$sulfonates are preferred, such as for example, $SO_3Me$, $SO_3Et$ and $SO_3Pr$.

A "therapeutically effective amount" refers to a quantity of a specified agent sufficient to achieve a desired effect in a subject being treated with that agent. For example, a therapeutically amount may be an amount of an HIV-1 integrase inhibitor that is sufficient to inhibit HIV or the development of AIDS in a subject. Ideally, a therapeutically effective amount of an agent is an amount sufficient to inhibit or treat the disease or condition without causing a substantial toxic effect in the subject. The therapeutically effective amount of an agent will be dependent on the subject being treated, the severity of the affliction, and the manner of administration of the therapeutic composition.

"Thiol" refers to the group —SH.

"$C_{1-6}$alkylthio" refers to a thiol group having the hydrogen replaced with a $C_{1-6}$alkyl group. $C_{1-3}$alkylthio groups are preferred, such as for example, methylthio, ethylthio and propylthio.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition. In certain embodiments disclosed herein, the treatment inhibits the development of AIDS in a subject.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Some of the compounds described herein may also exist in their tautomeric form.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. F or a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Groups which are substituted (e.g. substituted alkyl), may in some embodiments be substituted with a group which is substituted (e.g. substituted aryl). In some embodiments, the number of substituted groups linked together is limited to two (e.g. substituted alkyl is substituted with substituted aryl, wherein the substituent present on the aryl is not further substituted). In some embodiments, a substituted group is not substituted with another substituted group (e.g. substituted alkyl is substituted with unsubstituted aryl).

Overview

The compounds and pharmaceutical compositions disclosed herein may be useful in treating AIDS or an HIV infection. They may be used prophylactically to prevent new HIV infections. In certain embodiments, the compounds disclosed herein exhibit high inhibitory potency against wild-type HIV-1 integrase and raltegravir (RAL)- and elitegravir (EVG)-resistant HIV-1 integrase. Certain compounds disclosed herein exhibit therapeutic selectivity indices of greater than 10,000 based on low cytotoxicity and nanomolar efficacies.

Compounds

Disclosed herein is a compound of formula I, or a pharmaceutically acceptable salt or ester thereof, having a structure of:

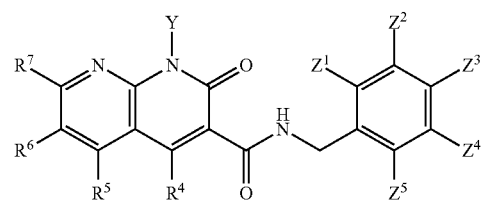

wherein X is N, C(OH), or CH;
Y is H or OH;
each of $Z^1$-$Z^5$ is independently H or halogen;
$R^4$ is H, OH, $NH_2$, $NHR^8$, $NR^8R^9$ or $R^8$;
$R^5$, $R^6$, and $R^7$ is each independently H, halogen, $OR^8$, $R^8$, $NHR^8$, $NR^8R^9$, $CO_2R^8$, $CONR^8R^9$, $SO_2NR^8R^9$, or $R^5$ and $R^6$ together with the carbon atoms to which $R^5$ and $R^6$ are attached form an optionally-substituted carbocycle or optionally-substituted heterocycle; and
$R^8$ and $R^9$ is each independently H, optionally-substituted alkyl, optionally-substituted alkenyl, optionally-substituted alkynyl, optionally-substituted aryl, optionally-substituted cycloalkyl, optionally-substituted cycloalkylene, optionally-substituted heterocycle, optionally-substituted amide, optionally-substituted ester, or $R^8$ and $R^9$ together with the nitrogen to which $R^8$ and $R^9$ are attached form an optionally-substituted heterocycle.

In certain embodiments, at least one, and preferably at least two, of $Z^1$-$Z^5$ is halogen. In certain embodiments, $Z^3$ is a halogen, preferably F. In certain embodiments, $Z^1$ and $Z^3$ are halogen, preferably F, or $Z^5$ and $Z^3$ are halogen, preferably F. In certain embodiments, $Z^3$ is a halogen and $Z^1$, $Z^2$, $Z^4$, and $Z^5$ are H. In certain embodiments, $Z^1$ and $Z^3$ are halogen and $Z^2$, $Z^4$ and $Z^5$ are H. In certain embodiments, $Z^5$ and $Z^3$ are halogen and $Z^2$, $Z^4$ and $Z^1$ are H.

In certain embodiments, X is N. In certain embodiments, Y is OH. In certain embodiments, X is N and Y is OH.

In certain embodiments, $R^4$ is $R^8$ or $NHR^8$, wherein $R^8$ is lower alkyl, phenyl, alkylester-substituted alkyl, aralkyl, substituted biphenylene, acyloxy-substituted alkyl, hydroxyl-substituted alkyl, or —$R^{10}(R^{11})(R^{12})$ wherein $R^{10}$ is an alkyl, $R^{11}$ is phenyl or hydroxyalkyl, and $R^{12}$ is alkylester. In particular, $R^4$ may be H; OH; —NH-phenyl; —NHC$(R^{13})_2$C(O)OCH$_3$, wherein each $R^{13}$ is independently H, lower alkyl, phenyl, or hydroxyalkyl; —NH-lower alkyl; —NH-alkanediyl-phenyl; —NH$_2$; para-substituted biphenylene; —NH-alkanediyl-OAc; —NH-alkanediyl-NH$_2$; or —NH-alkanediyl-OH. In certain embodiments, the alkanediyl of $R^4$ has 1 to 6 carbon atoms.

In certain embodiments, $R^5$ and $R^6$ are each H, and $R^7$ is optionally-substituted alkoxy, or optionally-substituted heterocycle. In certain embodiments, $R^5$ and $R^7$ are each H, and $R^6$ is -alkanediyl-C(O)O-alkyl; -alkenediyl-C(O))-alkyl; optionally-substituted alkoxy; or SO$_2$NR$^8$R$^9$. In certain embodiments, $R^7$ is H, and $R^5$ and $R^6$ are each independently hydroxyalkyl or alkoxyalkyl. In certain embodiments, $R^5$ is hydroxyalkyl.

In certain embodiments, $R^6$ is substituted alkyl, halogen, optionally substituted aryl, or amino. In particular, $R^6$ is a substituted alkyl such as, for example, hydroxyalkyl (e.g., hydroxy(C$_1$-C$_{10}$)alkyl), carboxylate-substituted alkyl (e.g., —(C$_1$-C$_6$)alkyl-C(O)O—CH$_3$, or acetoxy-substituted alkyl (—(C$_1$-C$_6$)alkyl-OC(O)—CH$_3$)), benzoxy-substituted alkyl, aminoalkyl, (cycloalkyl)alkyl, aralkyl, alkoxyalkyl, hydroxyalkoxyalkyl, amidoalkyl, thioalkyl, or sulfonyl alkyl. In more specific embodiments, $R^6$ is a hydroxyalkyl such as, for example, hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; or a carboxylate-substituted alkyl such as 3-methyl propanoate.

In further specific embodiments, $R^6$ is substituted-sulfonyl alkyl. For example, $R^6$ may be -D-S(O)$_2$-E-G, wherein D is (—CH$_2$—)$_n$, E is (—CH$_2$—)$_a$, and G is amino or N-heterocyclic, wherein n is 0 to 6 and a is 0 to 6; or -D-S(O)$_2$-J, wherein D is (—CH$_2$—)$_n$ and J is optionally-substituted alkyl, optionally-substituted aryl or optionally-substituted aryloxy, and n is 0 to 6. In certain embodiments, E, if present, or —S(O)$_2$— is bonded to a nitrogen heteroatom of the N-heterocyclic. In certain embodiments, the N-heterocyclic is piperazinyl or morpholinyl.

In further specific embodiments, $R^6$ is an amidoalkyl of -alkyl-C(O)NR$^{29}$R$^{30}$, wherein $R^{29}$ is H or an optionally-substituted alkyl, and $R^{30}$ is an optionally-substituted alkyl, particularly hydroxyalkyl, or an optionally-substituted aryl, particularly, optionally-substituted phenyl. In further specific embodiments, $R^6$ is an amidoalkenyl of -alkenyl-C(O)NR$^{29}$R$^{30}$, $R^{29}$ is H or an optionally-substituted alkyl, wherein $R^{30}$ is an optionally-substituted alkyl, particularly hydroxyalkyl or an optionally-substituted aryl, particularly, optionally-substituted phenyl.

Also disclosed herein, is a compound of formula II, or a pharmaceutically acceptable salt or ester thereof, having a structure of:

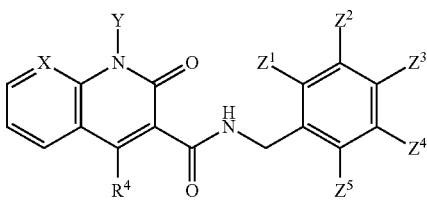

wherein $R^4$ is H or OH; Y is H or OH; and at least one of $Z^1$-$Z^5$ is a halogen.

In certain embodiments, $R^4$ is OH and Y is OH.

In certain embodiments, at least one, and preferably at least two, of $Z^1$-$Z^5$ is halogen. In certain embodiments, $Z^3$ is a halogen, preferably F. In certain embodiments, $Z^1$ and $Z^3$ are halogen, preferably F, or $Z^5$ and $Z^3$ are halogen, preferably F. In certain embodiments, $Z^3$ is a halogen and $Z^1$, $Z^2$, $Z^4$, and $Z^5$ are H. In certain embodiments, $Z^1$ and $Z^3$ are halogen and $Z^2$, $Z^4$ and $Z^5$ are H. In certain embodiments, $Z^5$ and $Z^3$ are halogen and $Z^2$, $Z^4$ and $Z^1$ are H.

Further disclosed herein is a compound of formula III, or a pharmaceutically acceptable salt or ester thereof, having a structure of:

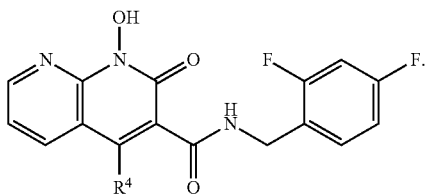

wherein $R^4$ is H, OH, NH$_2$, NHR$^8$, NR$^8$R$^9$ or R$^8$; and $R^8$ and $R^9$ is each independently H, optionally-substituted alkyl, optionally-substituted alkenyl, optionally-substituted alkynyl, optionally-substituted aryl, optionally-substituted cycloalkyl, optionally-substituted cycloalkylene, optionally-substituted heterocycle, optionally-substituted amide, optionally-substituted ester, or $R^8$ and $R^9$ together with the nitrogen to which $R^8$ and $R^9$ are attached form an optionally-substituted heterocycle.

In certain embodiments, $R^4$ is $R^8$ or NHR$^8$, wherein $R^8$ is lower alkyl, phenyl, alkylester-substituted alkyl, aralkyl, substituted biphenylene, acyloxy-substituted alkyl, hydroxyl-substituted alkyl or —$R^{10}(R^{11})(R^{12})$ wherein $R^{10}$ is an alkyl, $R^{11}$ is phenyl or hydroxyalkyl, and $R^{12}$ is alkylester. In particular, $R^4$ may be H; OH; —NH-phenyl; —NHC$(R^{13})_2$C(O)OCH$_3$, wherein each $R^{13}$ is independently H, lower alkyl, phenyl, or hydroxyalkyl; —NH-lower alkyl; —NH-alkanediyl-phenyl; —NH$_2$; para-substituted biphenylene; —NH-alkanediyl-OAc; —NH-alkanediyl-NH$_2$; or —NH-alkanediyl-OH. In certain embodiments, the alkanediyl of $R^4$ has 1 to 6 carbon atoms.

Also disclosed herein is a compound of formula IV, or a pharmaceutically acceptable salt or ester thereof, having a structure of:

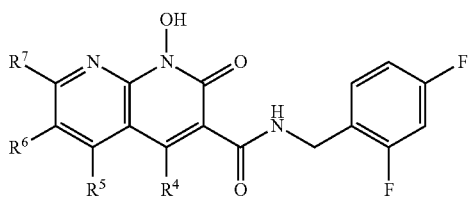

wherein $R^4$ is H, OH, $NH_2$, $NHR^8$, $NR^8R^9$ or R;
$R^5$, $R^6$, and $R^7$ is each independently H, $OR^8$, $R^8$, $NHR^8$, $NR^8R^9$, $CO_2R^8$, $SO_2NR^8R^9$, or $R^5$ and $R^6$ together with the carbon atoms to which $R^5$ and $R^6$ are attached form an optionally-substituted carbocycle or optionally-substituted heterocycle; and
$R^8$ and $R^9$ is each independently H, optionally-substituted alkyl, optionally-substituted alkylene, optionally-substituted aryl, optionally-substituted cycloalkyl, optionally-substituted cycloalkylene, optionally-substituted heterocycle, optionally-substituted amide, optionally-substituted ester, or $R^8$ and $R^9$ together with the nitrogen to which $R^8$ and $R^9$ are attached form an optionally-substituted heterocycle.

In certain embodiments, $R^4$ is $R^8$ or $NHR^8$, wherein $R^8$ is lower alkyl, phenyl, alkylester-substituted alkyl, aralkyl, substituted biphenylene, acyloxy-substituted alkyl, hydroxyl-substituted alkyl, or —$R^{10}(R^{11})(R^{12})$ wherein $R^{10}$ is an alkyl, $R^{11}$ is phenyl or hydroxyalkyl, and $R^{12}$ is alkylester. In particular, $R^4$ may be H; OH; —NH-phenyl; —$NHC(R^{13})_2C(O)OCH_3$, wherein each $R^{13}$ is independently H, lower alkyl, phenyl, or hydroxyalkyl; —NH-lower alkyl; —NH-alkanediyl-phenyl; —$NH_2$; para-substituted biphenylene; —NH-alkanediyl-OAc; —NH-alkanediyl-$NH_2$; or —NH-alkanediyl-OH. In certain embodiments, the alkanediyl of $R^4$ has 1 to 6 carbon atoms.

In certain embodiments, $R^5$ and $R^6$ are each H, and $R^7$ is optionally-substituted alkoxy, or optionally-substituted heterocycle. In certain embodiments, $R^5$ and $R^7$ are each H, and $R^6$ is -alkanediyl-C(O)O-alkyl; -alkenediyl-C(O))-alkyl; optionally-substituted alkoxy; or $SO_2NR^8R^9$. In certain embodiments, $R^7$ is H, and $R^5$ and $R^6$ are each independently hydroxyalkyl or alkoxyalkyl. In certain embodiments, $R^5$ is hydroxyalkyl.

In certain embodiments, $R^6$ is substituted alkyl, halogen, optionally substituted aryl, or amino. In particular, $R^6$ may be a substituted alkyl such as, for example, hydroxyalkyl (e.g., hydroxy($C_1$-$C_{10}$)alkyl), carboxylate-substituted alkyl (e.g., —($C_1$-$C_6$)alkyl-C(O)O—$CH_3$, or acetoxy-substituted alkyl (—($C_1$-$C_6$)alkyl-OC(O)—$CH_3$)), benzoxy-substituted alkyl, aminoalkyl, (cycloalkyl)alkyl, aralkyl, alkoxyalkyl, hydroxyalkoxyalkyl, amidoalkyl, thioalkyl or sulfonylalkyl. In more specific embodiments, $R^6$ is a hydroxyalkyl such as, for example, hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; or a carboxylate-substituted alkyl such as 3-methyl propanoate.

In further specific embodiments, $R^6$ is substituted-sulfonyl alkyl. For example, $R^6$ may be -D-S$(O)_2$-E-G, wherein D is (—$CH_2$—)$_n$, E is (—$CH_2$—)$_a$, and G is amino or N-heterocyclic, wherein n is 0 to 6 and a is 0 to 6; or -D-S$(O)_2$-J, wherein D is (—$CH_2$—)$_n$ and J is optionally-substituted alkyl, optionally-substituted aryl or optionally-substituted aryloxy, and n is 0 to 6. In certain embodiments, E, if present, or —S$(O)_2$— is bonded to a nitrogen heteroatom of the N-heterocyclic. In certain embodiments, the N-heterocyclic is piperazinyl or morpholinyl.

In further specific embodiments, $R^6$ is an amidoalkyl of -alkyl-C(O)$NR^{29}R^{30}$, wherein $R^{29}$ is H or an optionally-substituted alkyl, and $R^{30}$ is an optionally-substituted alkyl, particularly hydroxylalkyl, or an optionally-substituted aryl, particularly, optionally-substituted phenyl. In further specific embodiments, $R^6$ is an amidoalkenyl of -alkenyl-C(O)$NR^{29}R^{30}$, $R^{29}$ is H or an optionally-substituted alkyl, wherein $R^{30}$ is an optionally-substituted alkyl, particularly hydroxylalkyl or an optionally-substituted aryl, particularly, optionally-substituted phenyl.

In certain embodiments, $R^6$ is a substituted alkyl (particularly a hydroxyalkyl, a substituted-sulfonyl alkyl, or an amidoalkyl, as described above); and $R^4$ is OH, —$NH_2$, or —$NHCH_2C(O)OCH_3$.

Also disclosed herein is a compound of formula V, or a pharmaceutically acceptable salt or ester thereof, having a structure of:

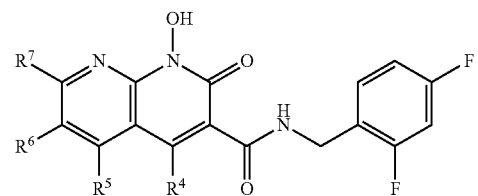

wherein $R^5$ and $R^7$ are each H;
$R^4$ is H, OH, $NH_2$, $NHR^8$, $NR^8R^9$ or $R^8$;
$R^8$ and $R^9$ is each independently H, optionally-substituted alkyl, optionally-substituted alkylene, optionally-substituted aryl, optionally-substituted cycloalkyl, optionally-substituted cycloalkylene, optionally-substituted heterocycle, optionally-substituted amide, optionally-substituted ester, or $R^8$ and $R^9$ together with the nitrogen to which $R^8$ and $R^9$ are attached form an optionally-substituted heterocycle; and
$R^6$ is substituted alkyl, halogen, optionally substituted aryl, amino, ester, sulfonate, or substituted sulfonyl.

In certain embodiments, $R^4$ is $R^8$ or $NHR^8$, wherein $R^8$ is lower alkyl, phenyl, alkylester-substituted alkyl, aralkyl, substituted biphenylene, acyloxy-substituted alkyl, hydroxyl-substituted alkyl, or —$R^{10}(R^{11})(R^{12})$ wherein $R^{10}$ is an alkyl, $R^{11}$ is phenyl or hydroxyalkyl, and $R^{12}$ is alkylester. In particular, $R^4$ may be H; OH; —NH-phenyl; —$NHC(R^{13})_2C(O)OCH_3$, wherein each $R^{13}$ is independently H, lower alkyl, phenyl, or hydroxyalkyl; —NH-lower alkyl; —NH-alkanediyl-phenyl; —$NH_2$; para-substituted biphenylene; —NH-alkanediyl-OAc; —NH-alkanediyl-$NH_2$; or —NH-alkanediyl-OH. In certain embodiments, the alkanediyl of $R^4$ has 1 to 6 carbon atoms.

In particular, $R^6$ may be a substituted alkyl such as, for example, hydroxyalkyl (e.g., hydroxy($C_1$-$C_{10}$)alkyl), carboxylate-substituted alkyl (e.g., —($C_1$-$C_6$)alkyl-C(O)O—$CH_3$, or acetoxy-substituted alkyl (—($C_1$-$C_6$)alkyl-OC(O)—$CH_3$)), benzoxy-substituted alkyl, aminoalkyl, (cycloalkyl)alkyl, aralkyl, alkoxyalkyl, hydroxyalkoxyalkyl, amidoalkyl, thioalkyl, or sulfonylalkyl. In more specific embodiments, $R^6$ is a hydroxyalkyl such as, for example, hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; or a carboxylate-substituted alkyl such as 3-methyl propanoate.

In further specific embodiments, $R^6$ is substituted-sulfonyl alkyl. For example, $R^6$ may be -D-S$(O)_2$-E-G, wherein D is (—$CH_2$—)$_n$, E is (—$CH_2$—)$_a$, and G is amino or N-heterocyclic, wherein n is 0 to 6 and a is 0 to 6; or -D-S(O)$_2$-J, wherein D is (—CH$_2$—)$_n$ and J is optionally-substituted alkyl, optionally-substituted aryl or optionally-substituted aryloxy, and n is 0 to 6. In certain embodiments, E, if present, or —S(O)$_2$— is bonded to a nitrogen heteroatom of the N-heterocyclic. In certain embodiments, the N-heterocyclic is piperazinyl or morpholinyl.

In further specific embodiments, $R^6$ is an amidoalkyl of -alkyl-C(O)NR$^{29}$R$^{30}$, wherein $R^{29}$ is H or an optionally-substituted alkyl, and $R^{30}$ is an optionally-substituted alkyl, particularly hydroxyalkyl, or an optionally-substituted aryl, particularly, optionally-substituted phenyl. In further specific embodiments, $R^6$ is an amidoalkenyl of -alkenyl-C(O) NR$^{29}$R$^{30}$, $R^{29}$ is H or an optionally-substituted alkyl, wherein $R^{30}$ is an optionally-substituted alkyl, particularly hydroxyalkyl or an optionally-substituted aryl, particularly, optionally-substituted phenyl.

In certain embodiments, $R^6$ is a substituted alkyl (particularly a hydroxyalkyl, substituted-sulfonyl alkyl, or an amidoalkyl, as described above); and $R^4$ is OH, —NH$_2$, or —NHCH$_2$C(O)OCH$_3$.

Figure 2:
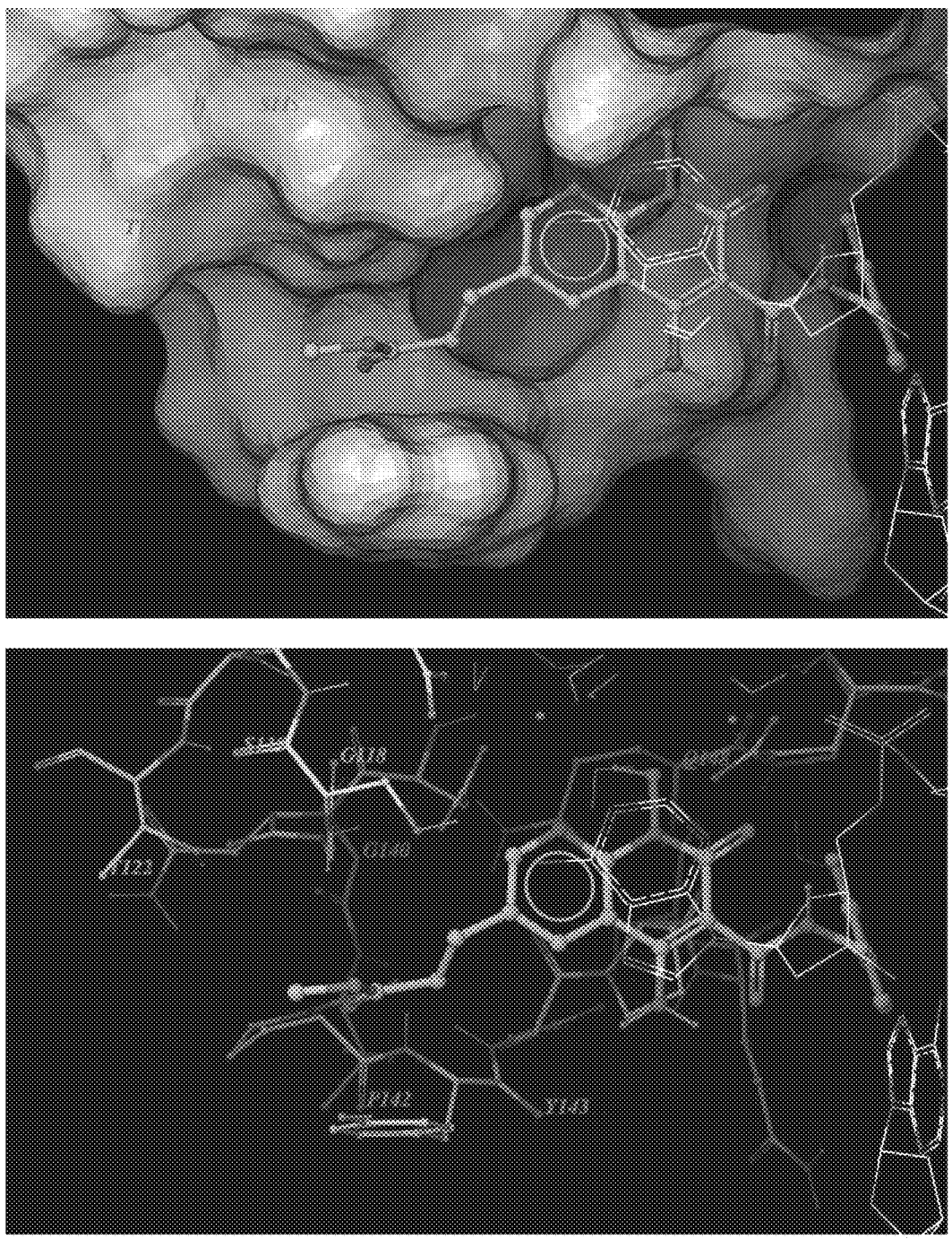
FIG. 2. Docking of XZ434 in a homology model of HIV-1 IN derived from the co-crystal DTG bound to the PFV IN along with DNA substrate using Molsoft ICM software.
Figure 3:
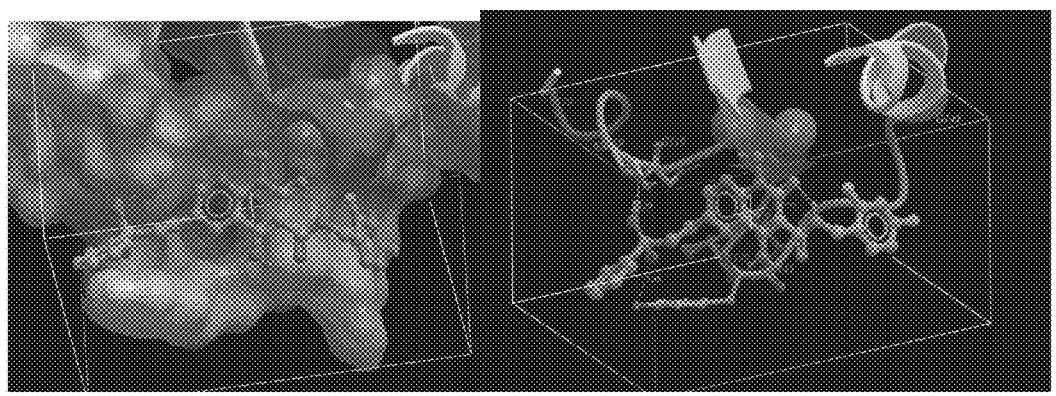
FIG. 3. Docking of XZ446 in a homology model of HIV-1 IN derived from the co-crystal DTG bound to the PFV IN along with DNA substrate using Molsoft ICM software.

Also disclosed herein is a compound of formula VI, or a pharmaceutically acceptable salt or ester thereof, having a structure of:

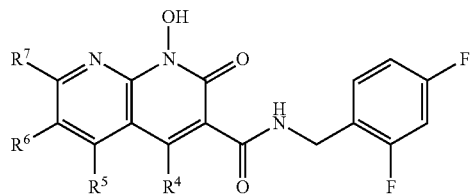

wherein $R^5$ and $R^7$ are each H;
$R^4$ is H, OH, NH$_2$, NHR$^8$, NR$^8$R$^9$ or R;
$R^8$ and $R^9$ is each independently H, optionally-substituted alkyl, optionally-substituted alkylene, optionally-substituted aryl, optionally-substituted cycloalkyl, optionally-substituted cycloalkylene, optionally-substituted heterocycle, optionally-substituted amide, optionally-substituted ester, or $R^8$ and $R^9$ together with the nitrogen to which $R^8$ and $R^9$ are attached form an optionally-substituted heterocycle; and $R^6$ is a substituent that interacts with amino acid residues Thr122, Ser 119, Gly118, Pro142, Tyr143 that are present in a cavity of HIV-1 integrase. These interactions may improve the binding of the related inhibitors, especially to drug resistant integrases. The $R^6$ substituent occupies a valley situated beneath the flexible loop Y143 residue (shown in FIGS. 1 and 2) that improves the binding of the compounds to the active site of HIV-1 integrase. The binding interactions of the $R^6$ substituent reveal a new pattern that differs from those shown by the third ring of heterotricycle core structure of DTG, and is believed to be important in retaining potency against RAL-resistant IN mutants In certain embodiments of formula VI, $R^6$ comprises at least one hydroxyl moiety that forms a hydrogen bond within 3 Å from the hydrogen to oxygen within Thr122 hydroxyl group, or at least one hydroxyl moiety that forms a hydrogen bond within 3 Å from the oxygen to the hydrogen within the amide backbone between Gly118 and Ser119, Thr122 hydroxyl group, or at least one carboxylic moiety that forms a hydrogen bond within 3 Å from the oxygen to the hydrogen within the amide backbone between Gly118 and Ser119, or at least one carboxylic moiety that forms a hydrogen bond within 3 Å from the oxygen to the hydrogen within the amide backbone between Pro142 and Tyr143. In certain embodiments of formula VI, $R^6$ comprises at least one sulfonyl moiety that forms a hydrogen bond within 3 Å from the oxygen to the hydrogen within the amide backbone between Gly118.

In certain embodiments of formula VI, $R^6$ is a substituted alkyl such as, for example, hydroxyalkyl (e.g., hydroxy(C$_1$-C$_{10}$)alkyl), or carboxylate-substituted alkyl (e.g., —(C$_1$-C$_6$) alkyl-C(O)O—CH3, or acetoxy-substituted alkyl (—(C$_1$-C$_6$)alkyl-OC(O)—CH$_3$)). In more specific embodiments, $R^6$ is a hydroxyalkyl such as, for example, hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; or a carboxylate-substituted alkyl such as 3-methyl propanoate.

Also disclosed herein is a method for inhibiting the integration of viral DNA by HIV-1 integrase, comprising contacting HIV-1 integrase with a compound that interacts with amino acid residues Thr122, Ser 119, Gly118, Pro142, Tyr143 that are present in a cavity of the HIV-1 integrase. Docking studies using a homology model of HIV-1 IN based on the co-crystal structure of DTG bound to the primitive foamy virus (PFV) IN along with DNA substrate using Molsoft ICM software, show that a compound moiety (e.g., a hydroxyalkyl substituent) that occupies a valley situated beneath the flexible loop Y143 residue (shown in FIGS. 1 and 2) can be part of a compound that inhibits the activity of HIV-1 IN. The binding interactions of the moiety reveal a new pattern that differs from those shown by the third ring of heterotricycle core structure of DTG, and it is believed to be important in retaining potency against RAL-resistant IN mutants. This new mode of binding may provide an important key to overcome some of the RAL-resistance mutations. For example, in cell-based assays many of the compounds disclosed herein show low cytotoxicity and high selectivity indices [(SI=CC$_{50}$/EC$_{50}$)>100,000], while exhibiting low nanomolar potency against a panel of IN mutants. In certain embodiments, the compound comprises at least one hydroxyl moiety that forms a hydrogen bond within 3 Å from the hydrogen to oxygen within Thr122 hydroxyl group, or at least one hydroxyl moiety that forms a hydrogen bond within 3 Å from the oxygen to the hydrogen within the amide backbone between Gly118 and Ser119, Thr122 hydroxyl group, or at least one carboxylic moiety that forms a hydrogen bond within 3 Å from the oxygen to the hydrogen within the amide backbone between Gly118 and Ser119, or at least one carboxylic moiety that forms a hydrogen bond within 3 Å from the oxygen to the hydrogen within the amide backbone between Pro142 and Tyr143.

Illustrative compounds are shown below and in Tables 1-5. In the compounds shown below, $R^4$ is H, OH, NH$_2$, NHR$^8$, NR$^8$R$^9$ or R$^8$ as described above.

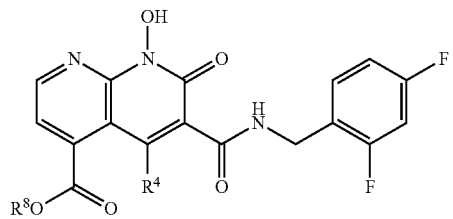

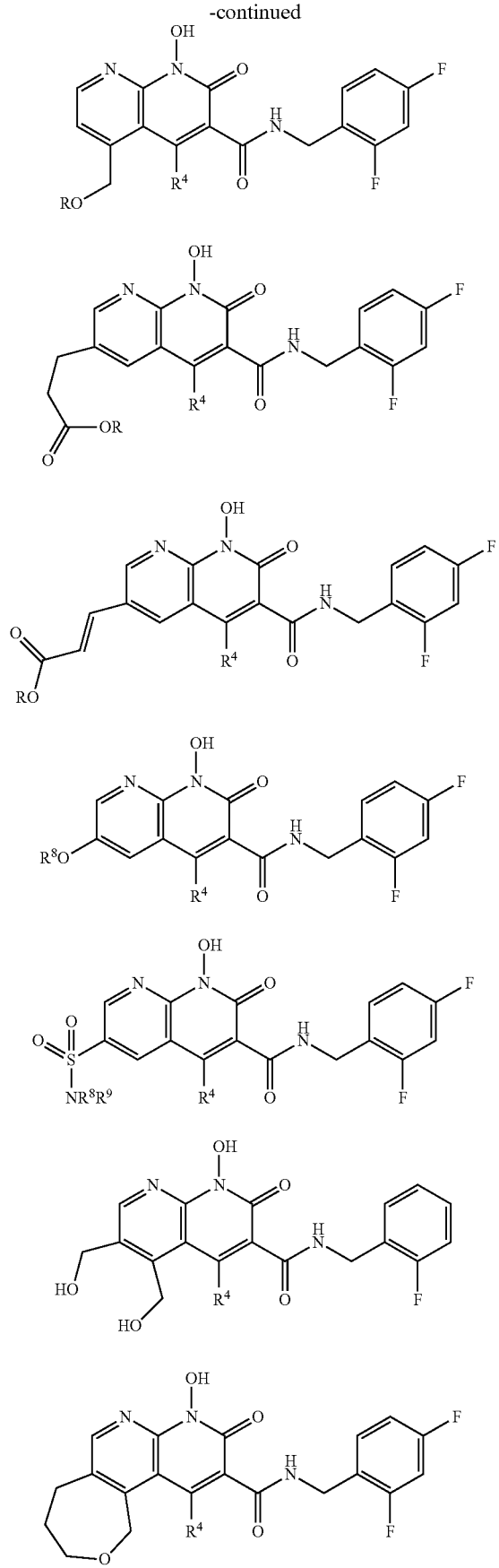
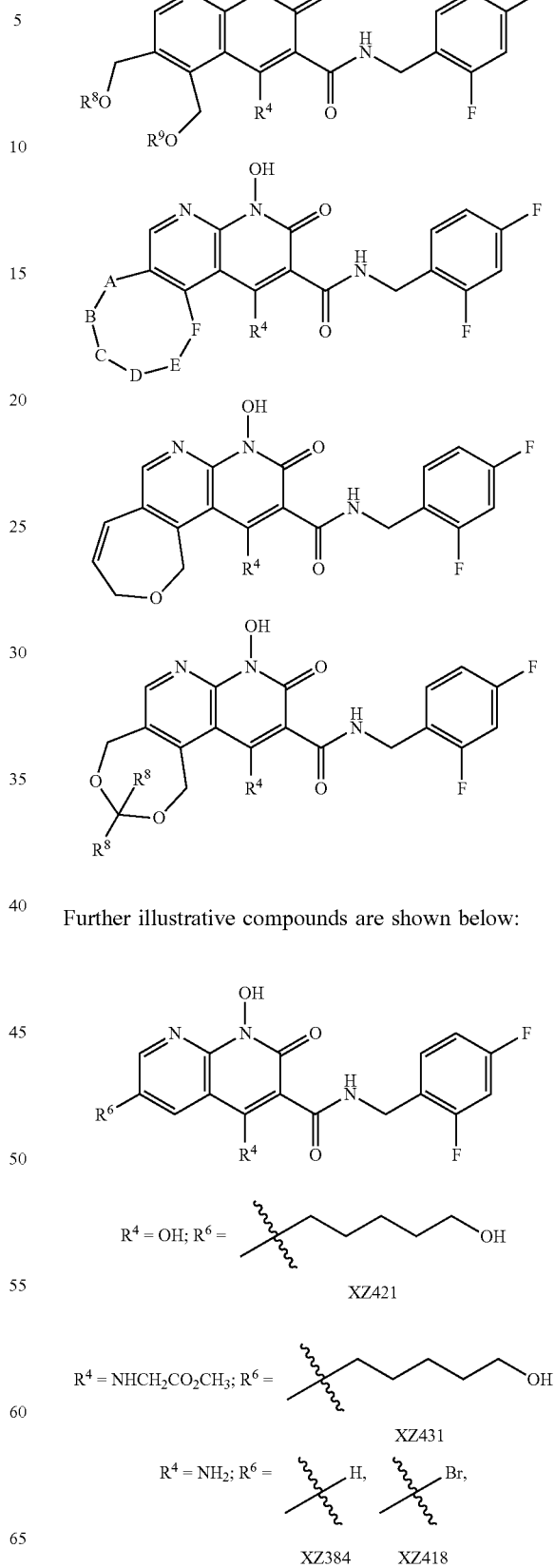
Further illustrative compounds are shown below:

-continued
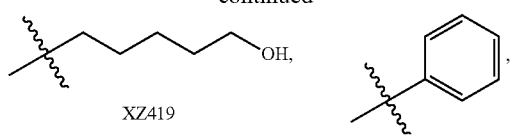
XZ419
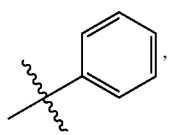
XZ420
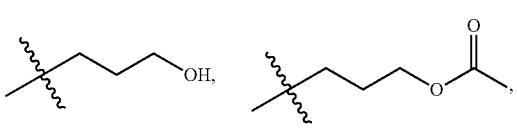
XZ423  XZ424
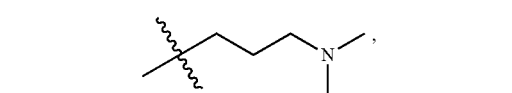
XZ425
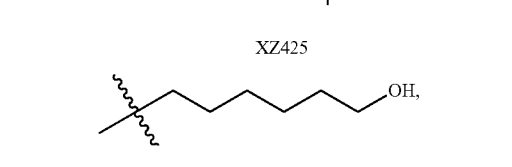
XZ426
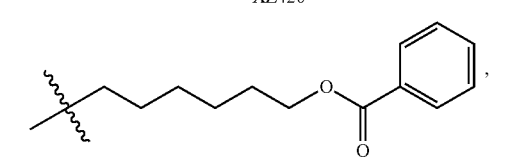
XZ427
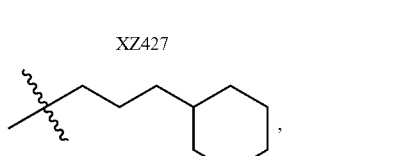
XZ428
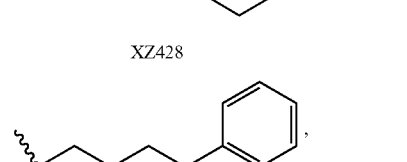
XZ429
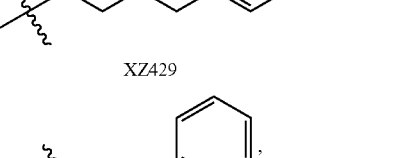
XZ430
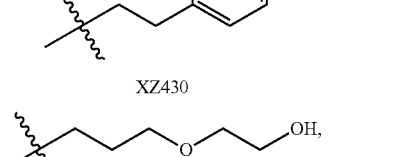
XZ432
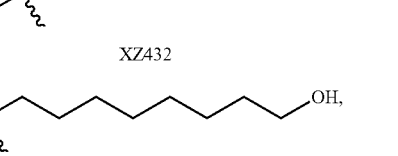
XZ433
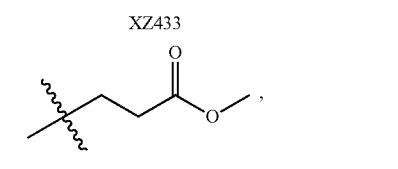
XZ434
-continued
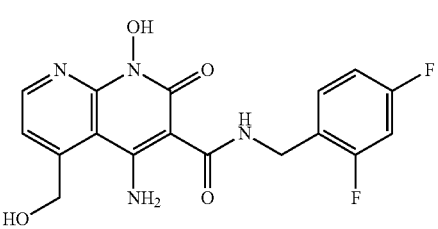
, or
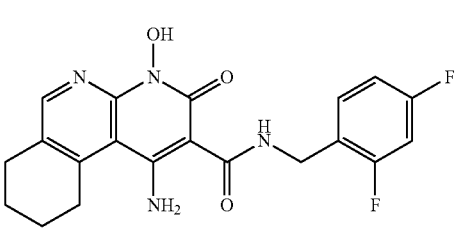
Additional illustrative compounds are shown below:
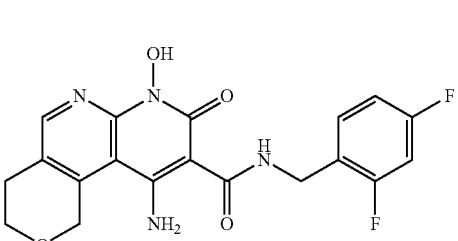
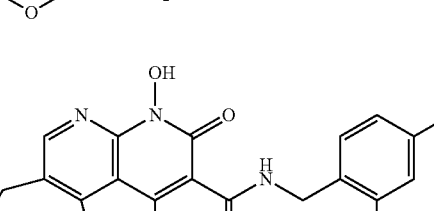
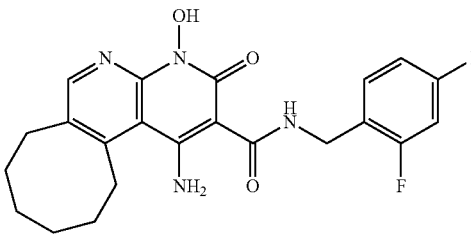

Further illustrative compounds are shown below:
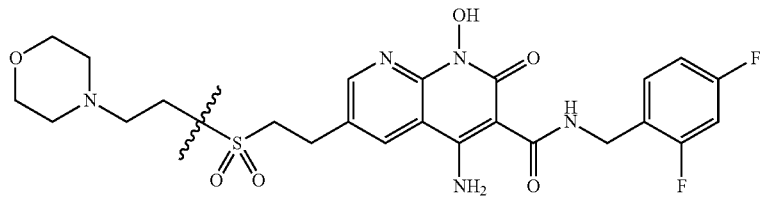
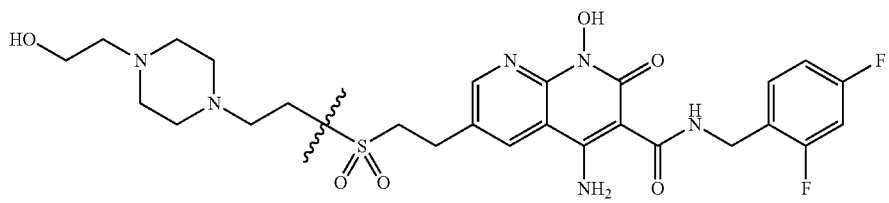
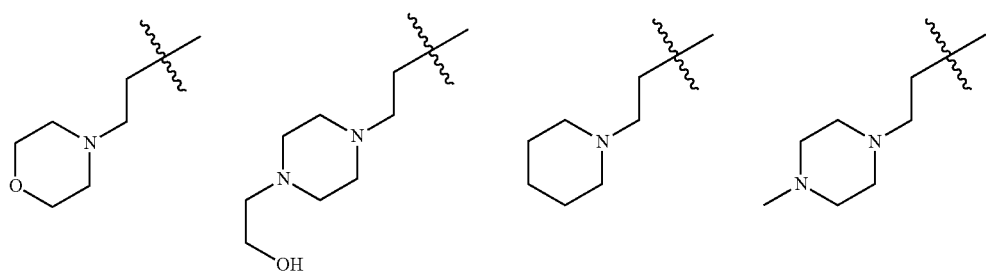
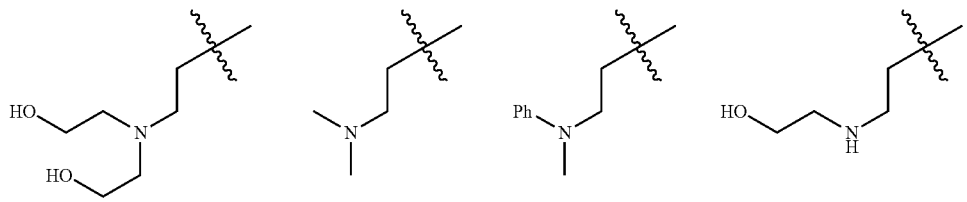
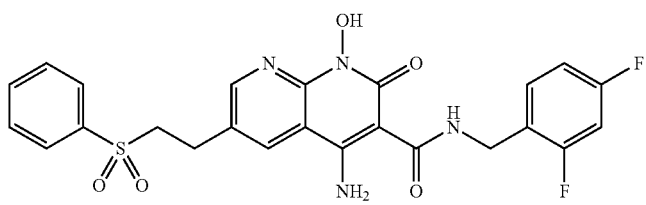
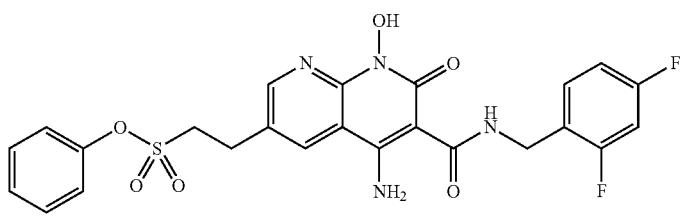
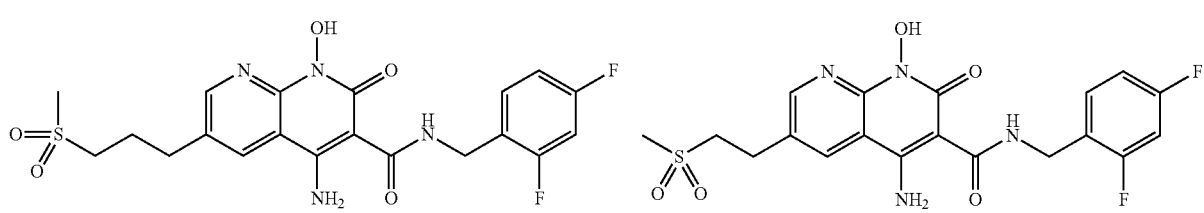 [SMILES: CS(=O)(=O)CCCc1cnc2c(c1)c(N)c(C(=O)NCc1ccc(F)cc1F)c(=O)n2O ; CS(=O)(=O)CCc1cnc2c(c1)c(N)c(C(=O)NCc1ccc(F)cc1F)c(=O)n2O]

The compounds disclosed herein may be synthesized as described below.
Synthesis Protocols:
Schemes
Scheme A. Preparation of 1-hydroxy-2-oxo-1,2-dihydroquinoline-3-carboxamide analogues using Koevenagel reaction.
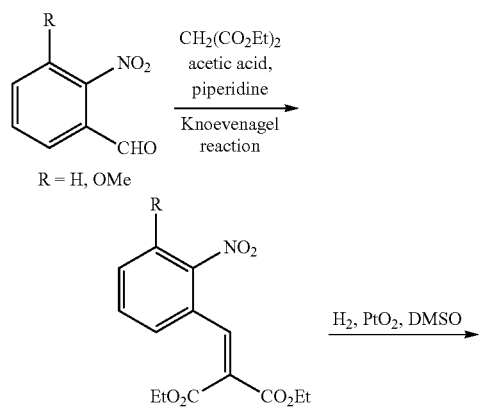
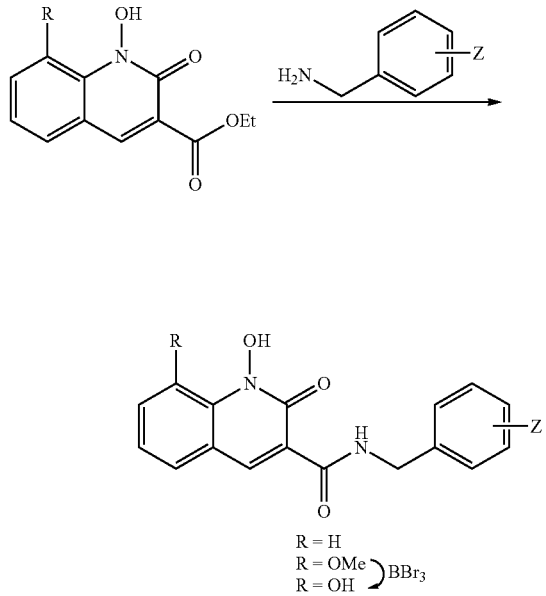
Scheme B. Preparation of starting pyridine analogues.
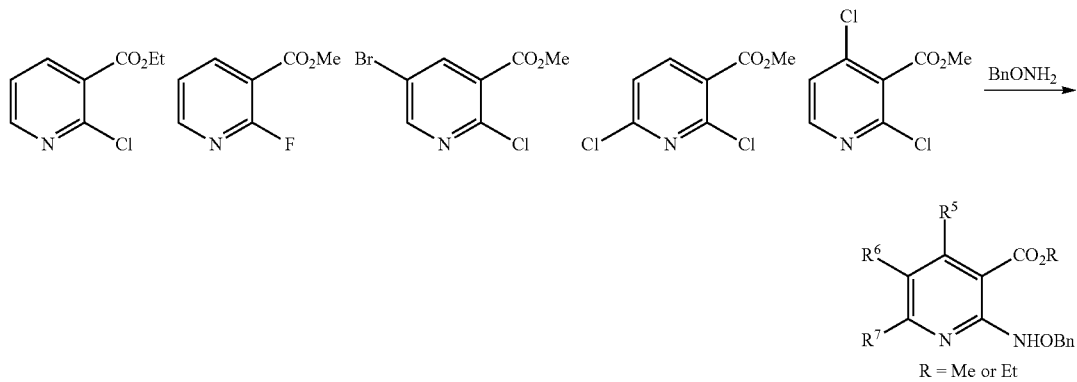
Scheme C. Preparation of 1-hydroxy-2-oxo-1,2-dihydro-1,8-naphthyridine-3-carboxamide analogues.
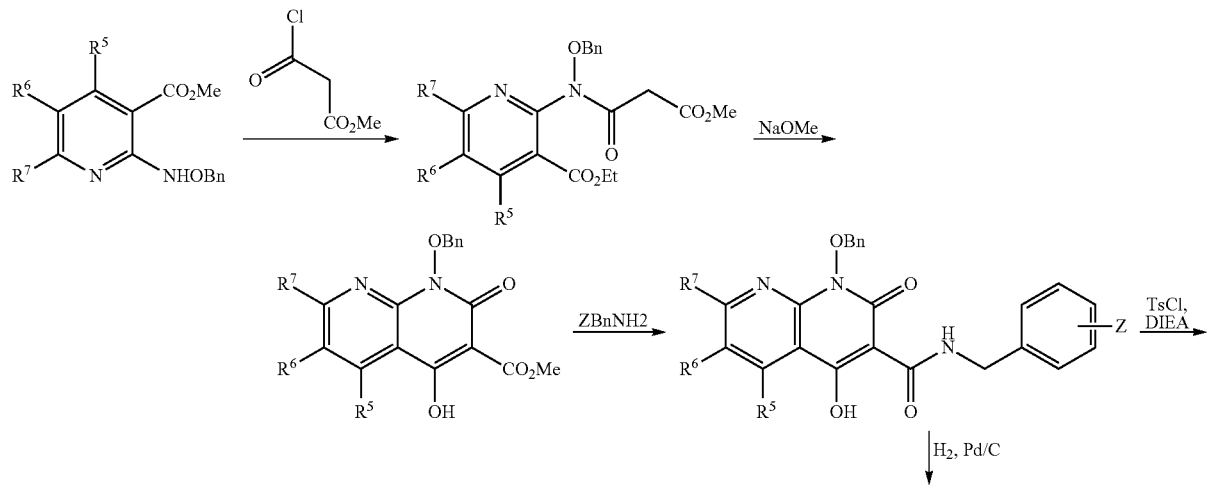

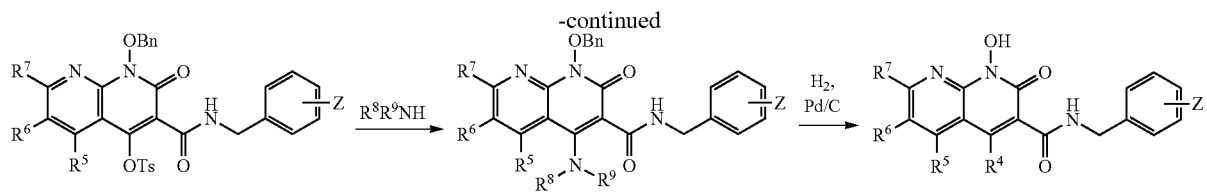
Scheme D. Preparation of 1-hydroxy-2-oxo-1,2-dihydro-1,8-naphthyridine-3-carboxamide and 2-oxo-1,2-dihydro-1,8-naphthyridine-3-carboxamide analogues.
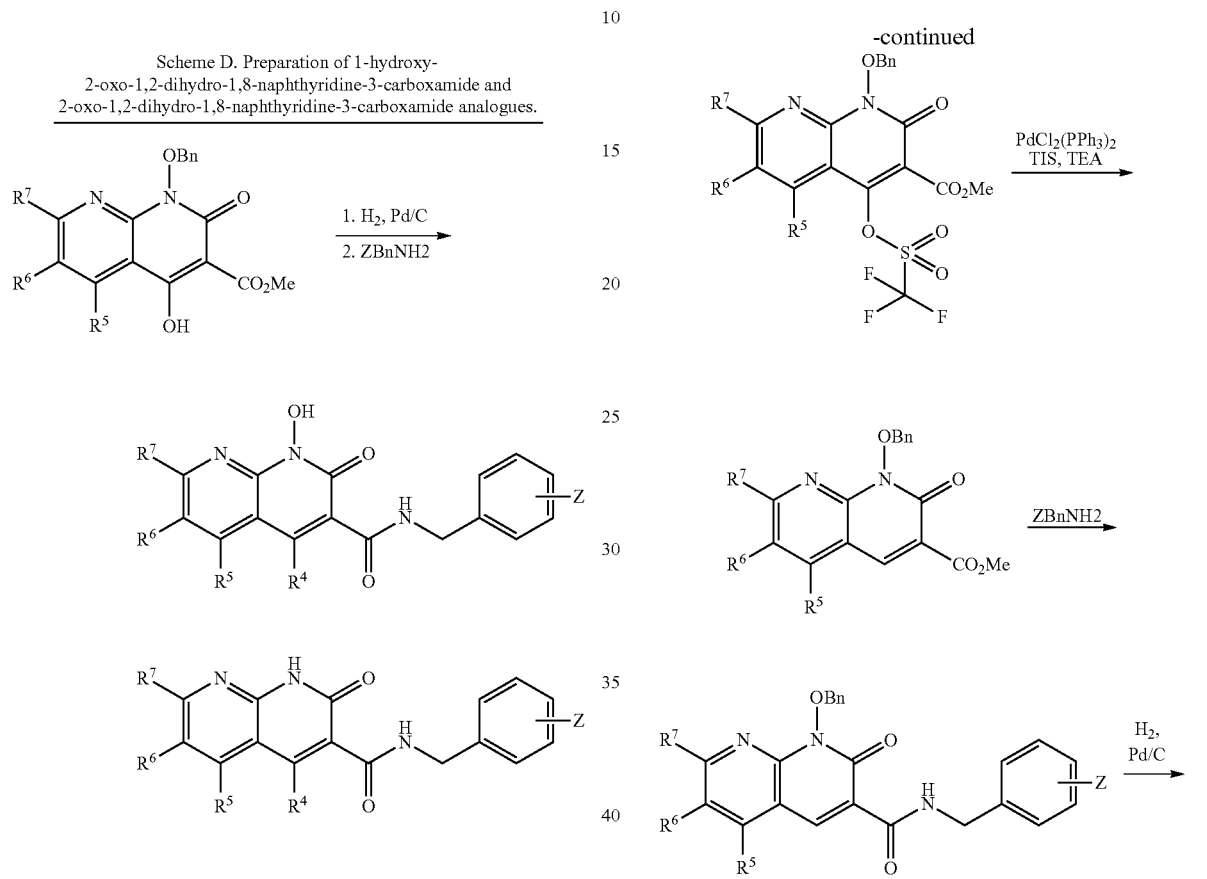
Scheme E. Preparation of 1-hydroxy-2-oxo-1,2-dihydro-1,8-naphthyridine-3-carboxamide analogues.
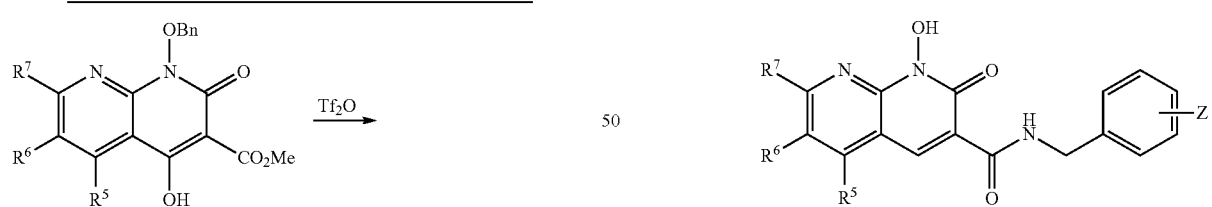
Scheme F. Preparation of 4-amino-1-hydroxy-2-oxo-1,2-dihydro-1,8-naphthyridine-3-carboxamide analogues.
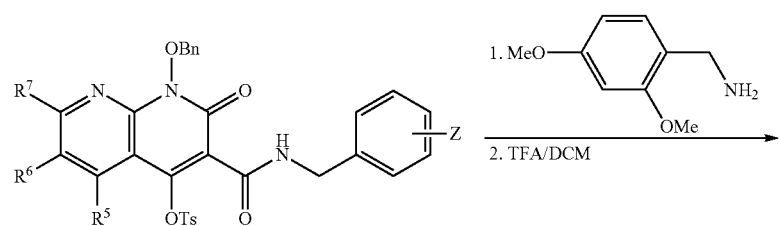

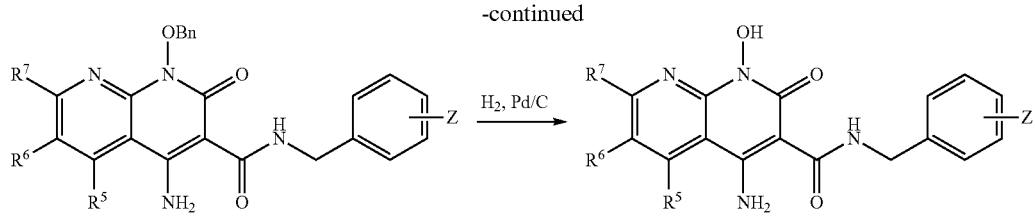

Scheme G. Preparation of 1-hydroxy-2-oxo-1,2-dihydro-1,8-naphthyridine-3-carboxamide analogues using coupling reactions.

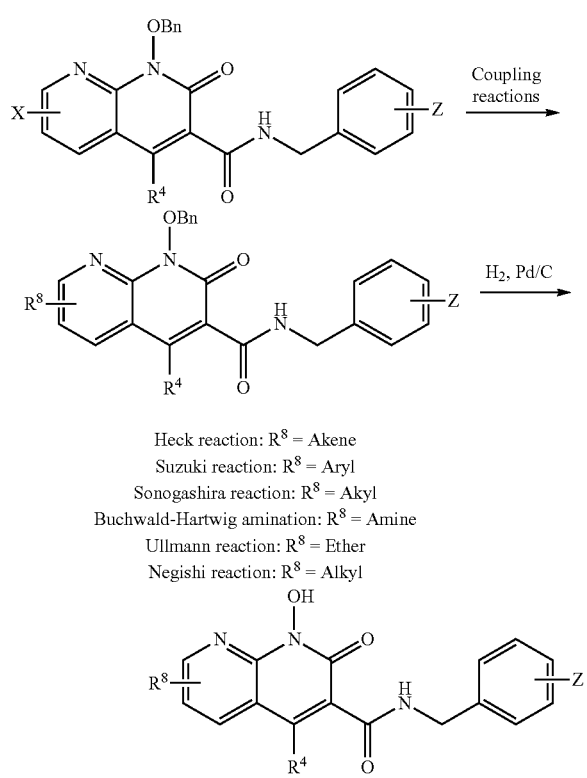

Heck reaction: $R^8$ = Akene
Suzuki reaction: $R^8$ = Aryl
Sonogashira reaction: $R^8$ = Akyl
Buchwald-Hartwig amination: $R^8$ = Amine
Ullmann reaction: $R^8$ = Ether
Negishi reaction: $R^8$ = Alkyl Synthesis:
General Synthetic.

$^1$H and $^{13}$C NMR data were obtained on a Varian 400 MHz spectrometer or a Varian 500 MHz spectrometer and are reported in ppm relative to TMS and referenced to the solvent in which the spectra were collected. Solvent was removed by rotary evaporation under reduced pressure and anhydrous solvents were obtained commercially and used without further drying. Purification by silica gel chromatography was performed using Combiflash with EtOAc-hexanes solvent systems. Preparative high pressure liquid chromatography (HPLC) was conducted using a Waters Prep LC4000 system having photodiode array detection and Phenomenex $C_{18}$ columns (250 mm×21.2 mm 10 μm particle size, 110 Å pore) at a flow rate of 10 mL/min. Binary solvent systems consisting of A=0.1% aqueous TFA and B=0.1% TFA in acetonitrile were employed with gradients as indicated. Products were obtained as amorphous solids following lyophilization. Electrospray ionization-mass spectrometric (ESI-MS) and atmospheric pressure chemical ionization-mass spectrometric (APCI-MS) were acquired with an Agilent LC/MSD system equipped with a multimode ion source. High resolution mass spectrometric (HRMS) were acquired with LTQ-Orbitrap-XL at 30K resolution by LC/MS-ESI.

General Synthesis for Compounds
1-Hydroxy-2-oxo-1,2-dihydroquinoline-3-carboxamide Analogues Scheme 1. Preparation of 1-hydroxy-2-oxo-1,2-dihydroquinoline-3-carboxamide analogues using Knoevenagel reaction.

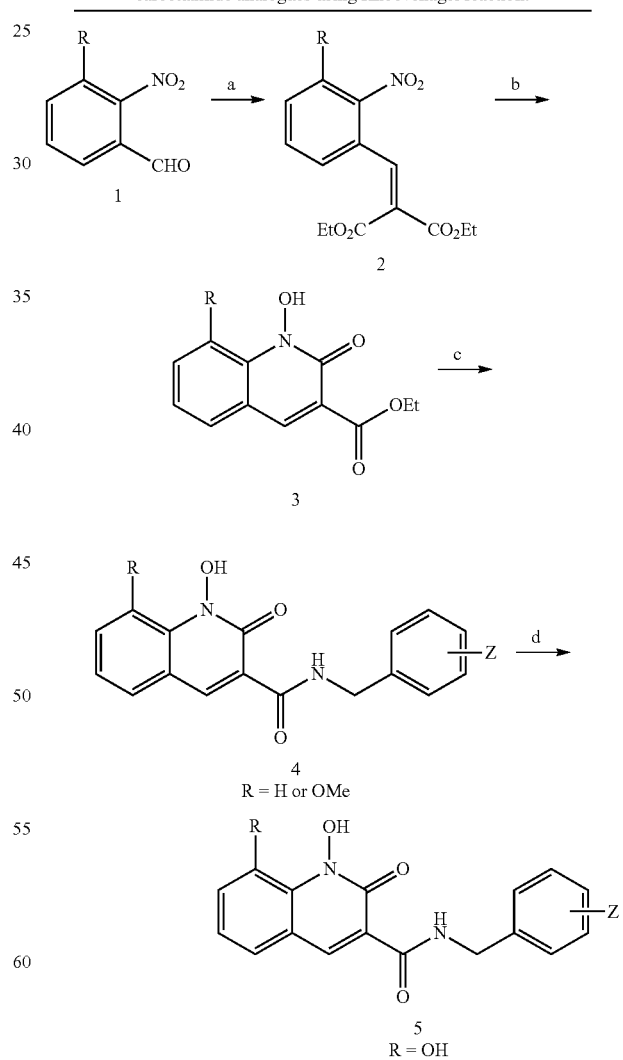

Reagents and conditions: a) HOAc, CH$_2$(CO$_2$Et)$_2$, piperidine; b) H$_2$, PtO$_2$, DMSO; c) ZBnNH$_2$; d) BBr$_3$.

General Procedure A for the Synthesis of Diethyl 2-(2-nitrobenzylidene)malonates (2)

Commercial available 2-nitrobenzaldehyde (1) (5 mmol) was added to a solution of diethyl malonate (60 mmol), acetic acid (20 mmol) and piperidine (6 mmol). The solution was microwave heated at 80° C. for 15 hours. The reaction was diluted with EtOAc (60 mL) and washed with NaHCO$_3$ (aq., 30 mL). The organic layer was dried over Na2SO4. The crude product was filtered and the filtrate was concentrated. The residue was purified by Combiflash and eluted with hexanes and ethyl acetate. Diethyl 2-(2-nitrobenzylidene) malonates (2) were afforded.

General Procedure B for the Synthesis of Ethyl 1-hydroxy-2-oxo-1,2-dihydroquinoline-3-carboxylates (3)

Diethyl 2-(2-nitrobenzylidene)malonate (2) (0.5 mmol) was dissolved in acetic acid (3 mL). DMSO (0.8 mmol) was added, followed by Platinum(IV) oxide (0.075 mmol) was added at rt. The reaction was stirred at rt under hydrogen for 22 hours. The mixture was filtered and washed by methanol. The filtrate was concentrated. The residue was purified by Combiflash and eluted with hexanes and ethyl acetate. Ethyl 1-hydroxy-8-methoxy-2-oxo-1,2-dihydroquinoline-3-carboxylates (3) were afforded.

General Procedure C for the Synthesis of N-(benzyl)-1-hydroxy-2-oxo-1,2-dihydroquinoline-3-carboxamides (4)

Ethyl 1-hydroxy-2-oxo-1,2-dihydroquinoline-3-carboxylate (3) (0.4 mmol) and benzylamine (3 mL) was mixed. The reaction was heated to 60° C. for 14 hours. The mixture was purified by HPLC. N-(benzyl)-1-hydroxy-2-oxo-1,2-dihydroquinoline-3-carboxamides (4) was afforded.

General Procedure D for the Synthesis of N-(halobenzyl)-1,8-dihydroxy-2-oxo-1,2-dihydroquinoline-3-carboxamides (5)

HPLC purified N-(halobenzyl)-1-hydroxy-8-methoxy-2-oxo-1,2-dihydroquinoline-3-carboxamide (4) (0.1 mmol) was mixed with tribromoborane (0.8 mmol, 2.0 M in DCM). The mixture was stirred at rt overnight. Methanol was added dropwise to quench the reaction. The mixture was purified by HPLC. N-(halobenzyl)-1,8-dihydroxy-2-oxo-1,2-dihydroquinoline-3-carboxamides (5) was afforded.

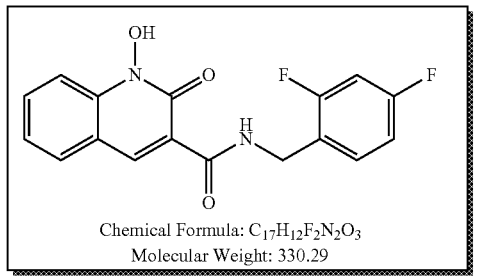

Chemical Formula: C$_{17}$H$_{12}$F$_2$N$_2$O$_3$
Molecular Weight: 330.29

Compound N-(2,4-difluorobenzyl)-1-hydroxy-2-oxo-1,2-dihydroquinoline-3-carboxamide (XZ353)

Purification by preparative HPLC (as indicated in the General Synthetic Procedures using a 00G-4436-P0-AX column with a linear gradient of 30% B to 60% B over 30 minutes; retention time=28.1 minutes), fluffy solid XZ353 was afforded. ESI-MS m/z: 331.1 (M+H$^+$).

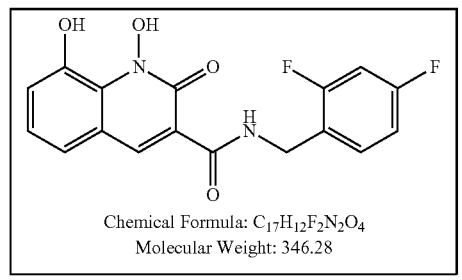 [SMILES: O=C(NCc1ccc(F)cc1F)c1cc2cccc(O)c2n(O)c1=O]

Chemical Formula: C$_{17}$H$_{12}$F$_2$N$_2$O$_4$
Molecular Weight: 346.28

Compound N-(2,4-difluorobenzyl)-1,8-dihydroxy-2-oxo-1,2-dihydroquinoline-3-carboxamide (XZ369)

Purification by preparative HPLC (as indicated in the General Synthetic Procedures using a 00G-4436-P0-AX column with a linear gradient of 30% B to 65% B over 30 minutes; retention time=24.6 minutes), fluffy solid XZ369 was afforded. ESI-MS m/z: 347.1 (M+H$^+$).

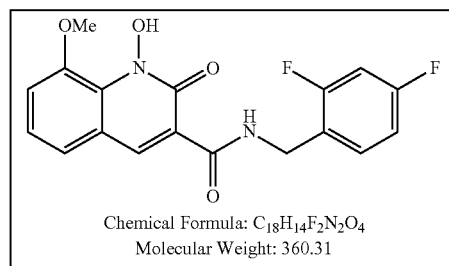

Chemical Formula: C$_{18}$H$_{14}$F$_2$N$_2$O$_4$
Molecular Weight: 360.31

Compound N-(2,4-difluorobenzyl)-1-hydroxy-8-methoxy-2-oxo-1,2-dihydroquinoline-3-carboxamide (XZ370)

Purification by preparative HPLC (as indicated in the General Synthetic Procedures using a 00G-4436-P0-AX column with a linear gradient of 30% B to 65% B over 30 minutes; retention time=27.0 minutes), fluffy solid XZ370 was afforded. ESI-MS m/z: 361.1 (M+H$^+$).

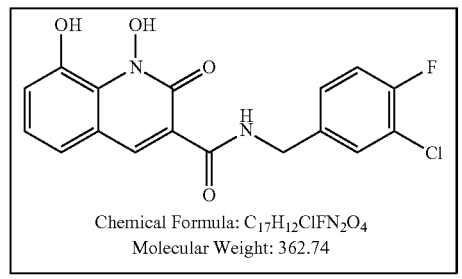 [SMILES: O=C(NCc1ccc(F)c(Cl)c1)c1cc2cccc(O)c2n(O)c1=O]

Chemical Formula: C$_{17}$H$_{12}$ClFN$_2$O$_4$
Molecular Weight: 362.74

Compound N-(3-chloro-4-fluorobenzyl)-1,8-dihydroxy-2-oxo-1,2-dihydroquinoline-3-carboxamide (XZ374)

Purification by preparative HPLC (as indicated in the General Synthetic Procedures using a 00G-4436-P0-AX column with a linear gradient of 30% B to 65% B over 30 minutes; retention time=27.5 minutes), fluffy solid XZ374 was afforded. ESI-MS m/z: 363.0 (M+H$^+$).

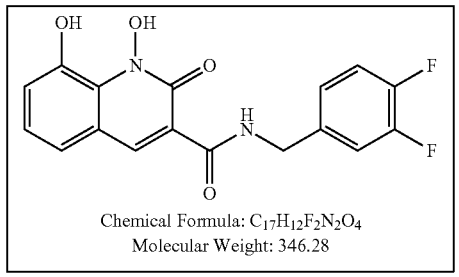 [SMILES: O=C(NCc1ccc(F)c(F)c1)c1cc2cccc(O)c2n(O)c1=O]

Compound N-(3,4-difluorobenzyl)-1,8-dihydroxy-2-oxo-1,2-dihydroquinoline-3-carboxamide (XZ375)

Purification by preparative HPLC (as indicated in the General Synthetic Procedures using a 00G-4436-P0-AX column with a linear gradient of 30% B to 65% B over 30 minutes; retention time=24.9 minutes), fluffy solid XZ375 was afforded. ESI-MS m/z: 347.1 (M+H$^+$).

General Synthesis for Compounds 1-Hydroxy-2-oxo-1,2-dihydro-1,8-naphthyridine-3-carboxamide Analogues General Procedure E for the Synthesis of Benzoxylamines (7)

Methyl 2-fluoronicotinate or Ethyl 2-chloronicotinate (6) (1 mmol), O-benzylhydroxylamine (3 mmol) and N-ethyl-N-isopropylpropan-2-amine (3 mmol) was dissolved in 1,4-Dioxane or DMSO. The reaction mixture was microwave-heated at 140° C. for 10 hours. The resultant mixture was extract by EtOAc. The organic phase was washed by brine and dried by sodium sulfate. The crude product was filtered and the filtrate was concentrated. The residue was purified by Combiflash and eluted with hexanes and ethyl acetate. 2-((Benzyloxy)amino)nicotinates (7) were afforded.

General Procedure F for the Synthesis of Methyl 1-(benzyloxy)-6-bromo-4-hydroxy-2-oxo-1,2-dihydro-1,8-naphthyridine-3-carboxylates (8)

To a solution of methyl or ethyl 2-((benzyloxy)amino) nicotinate (7) (2 mmol) and triethylamine (4 mmol) in DCM (10 ml), methyl 3-chloro-3-oxopropanoate (4 mmol) was added drop wise. The mixture was stirred at rt for 2 hours. The crude product was filtered and the filtrate was concentrated. The residue was purified by Combiflash and eluted with hexanes and ethyl acetate. Methyl or ethyl 2-(N-(benzyloxy)-3-methoxy-3-oxopropanamido)nicotinate (8) were afforded.

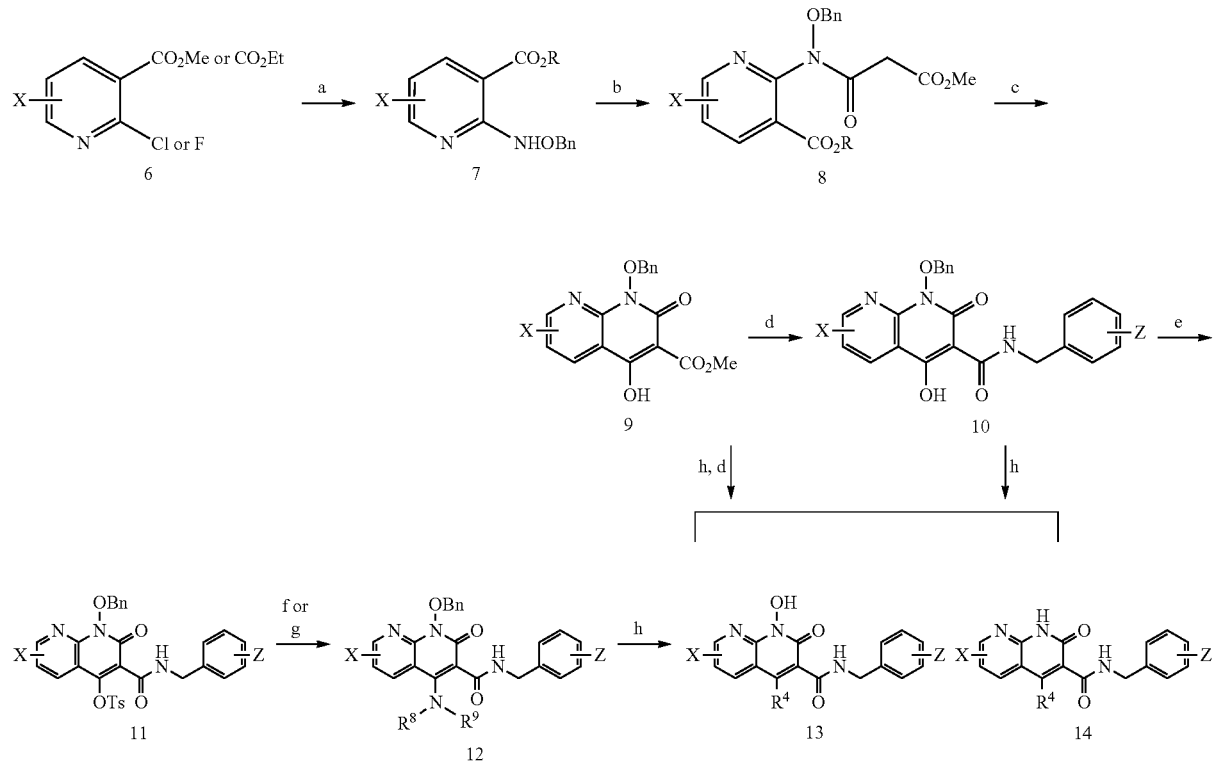

Scheme 2. General synthesis of 1-hydroxy-2-oxo-1,2-dihydro-1,8-naphthyridine-3-carboxamide.

Reagents and conditions: a) BnONH$_2$; b) ClCOCH$_2$CO$_2$CH$_3$, TEA, DCM; c) NaOMe, MeOH; d) ZBnNH$_2$, DMF; e) TsCl, TEA; f) R$^8$R$^9$NH or R$^8$R$^9$NH—HCl, DIEA, DMF; g) 2,4-dimethoxylbenzylamine, DMF then TFA, DCM; h) H$_2$, Pd/C.

General Procedure G for the Synthesis of Methyl 1-(benzyloxy)-6-bromo-4-hydroxy-2-oxo-1,2-dihydro-1,8-naphthyridine-3-carboxylates (9)

To a solution of Ethyl 2-(N-(benzyloxy)-3-methoxy-3-oxopropanamido)-5-bromonicotinate (8) (1.7 mmol) in MeOH (30 mL), was added sodium methanolate (4.2 mmol) (25% in methanol) at rt. The resultant yellow suspension was stirred at rt overnight. The reaction was brought to pH 4 by the addition of HCl (aq., 2N). The formed solids were collected. Methyl 1-(benzyloxy)-6-bromo-4-hydroxy-2-oxo-1,2-dihydro-1,8-naphthyridine-3-carboxylates (9) were afforded.

General Procedure H for the Synthesis of Amides (10)

Methyl carboxylates (9) (1.0 mmol) and halobenzylamines (10.0 mmol) was dissolved in DMF (1.0 mL). Microwaved heated to 140° C. for 2 hrs. The crude mixture was purified by Combiflash and eluted with hexanes and ethyl acetate. Amides (10) were afforded.

General Procedure I for the Synthesis of Toluenesulfonates (11)

Amides (10) (2.0 mmol) was dissolved in $CH_3CN$ (6.0 ml) and DCM (3.0 ml). Triethylamine (12.0 mmol) and 4-methylbenzene-1-sulfonyl chloride (6.0 mmol) was added. The mixture was stirred at rt overnight. The crude mixture was purified by Combiflash and eluted with hexanes and ethyl acetate. Toluenesulfonates (11) were afforded.

General Procedure J for the Synthesis of Amines (12)

p-Methylbenzenesulfonates (11) (1 mmol), N-ethyl-N-isopropylpropan-2-amine (10 mmol) and amines $R^8R^9NH$ or $R^8R^9NH$—HCl (5 mmol) in DMF (2 mL) was heated to 50° C. for 1 hr. The crude mixture was purified by Combiflash and eluted with hexanes and ethyl acetate. Amines (12) were afforded.

General Procedure K for the Synthesis of Amines (12)

Toluenesulfonates (11) (1 mmol), N-ethyl-N-isopropylpropan-2-amine (10 mmol) and (2,4-dimethoxyphenyl)methanamine (5 mmol) in DMF (2 mL) was heated to 50° C. for 1 hr. The crude mixture was purified by Combiflash and eluted with hexanes and ethyl acetate. Amines were collected. The amines were mixture with TFA/DCM (4 mL, 1/1) and concentrated. The left residue was purified by Combiflash and eluted with hexanes and ethyl acetate. Amines (12) were afforded.

General Procedure L for the Synthesis of Carboxamides (13) or (14)

Amides (12) (0.2 mmol) was dissolved in MeOH (15 mL) and EtOAc (5 mL). Pd/C (10%, 0.2 mmol) was added after degassed. The reaction was stirred at rt under hydrogen for 1 hour. The mixture was filtered and concentrated. The filtrate was concentrated and the residues were purified by HPLC. 1-hydroxy-2-oxo-1,2-dihydro-1,8-naphthyridine-3-carboxamides (13) or (14) were afforded.

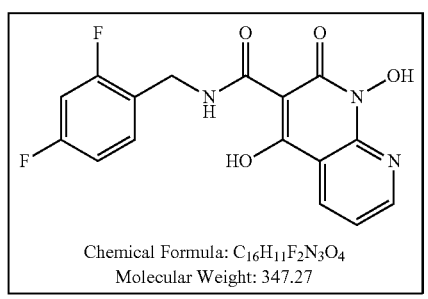

Chemical Formula: $C_{16}H_{11}F_2N_3O_4$
Molecular Weight: 347.27

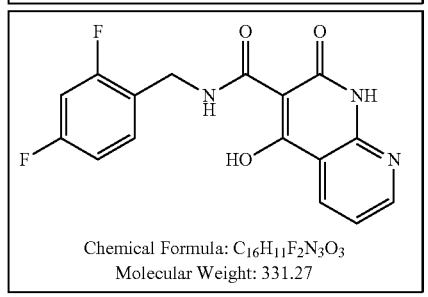

Chemical Formula: $C_{16}H_{11}F_2N_3O_3$
Molecular Weight: 331.27

Compound N-(2,4-difluorobenzyl)-1,4-dihydroxy-2-oxo-1,2-dihydro-1,8-naphthyridine-3-carboxamide (XZ351) and N-(2,4-difluorobenzyl)-4-hydroxy-2-oxo-1,2-dihydro-1,8-naphthyridine-3-carboxamide (XZ352)

Purification by preparative HPLC (as indicated in the General Synthetic Procedures using a 00G-4436-P0-AX column with a linear gradient of 20% B to 80% B over 30 minutes; for XZ351 retention time=24.7 minutes; for XZ352 retention time=29.0 minutes), white fluffy solid XZ351 and XZ352 was afforded. For XZ351: $^1$H NMR (500 MHz, DMSO-$d^6$) δ 10.95 (s, 1H), 10.42 (s, 1H), 8.77 (d, J=4.6 Hz, 1H), 8.40 (d, J=7.9 Hz, 1H), 7.49-7.41 (m, 1H), 7.41-7.34 (m, 1H), 7.21 (t, J=10.1 Hz, 1H), 7.03 (t, J=8.2 Hz, 1H), 4.57 (d, J=5.9 Hz, 2H). ESI-MS m/z: 348.0 (M+H$^+$). For XZ352: $^1$H NMR (500 MHz, DMSO-$d^6$) δ 12.32 (s, 1H), 10.57 (s, 1H), 8.70 (s, 1H), 8.36 (d, J=7.4 Hz, 1H), 7.48 (d, J=7.5 Hz, 1H), 7.36 (s, 1H), 7.28 (t, J=9.6 Hz, 1H), 7.10 (s, 1H), 4.62 (d, J=5.9 Hz, 2H). ESI-MS m/z: 332.1 (M+H$^+$).

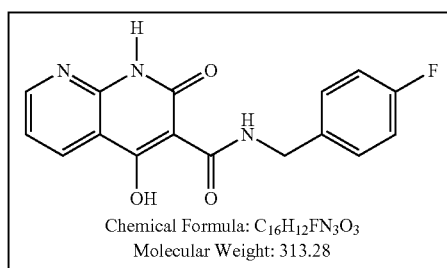

Chemical Formula: $C_{16}H_{12}FN_3O_3$
Molecular Weight: 313.28

Compound N-(4-fluorobenzyl)-4-hydroxy-2-oxo-1,2-dihydro-1,8-naphthyridine-3-carboxamide (XZ364)

Purification by preparative HPLC (as indicated in the General Synthetic Procedures using a 00G-4436-P0-AX column with a linear gradient of 20% B to 80% B over 30 minutes; retention time=27.6 minutes), fluffy solid XZ364 was afforded. ESI-MS m/z: 314.1 (M+H⁺).

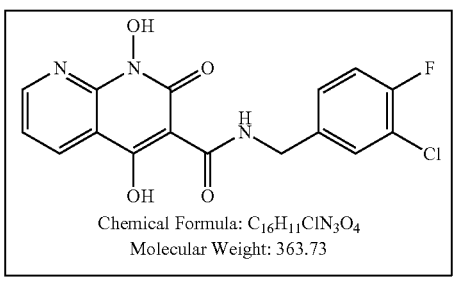 [SMILES: O=C(NCc1ccc(F)c(Cl)c1)c1c(O)c2cccnc2n(O)c1=O]

Compound N-(3-chloro-4-fluorobenzyl)-1,4-dihydroxy-2-oxo-1,2-dihydro-1,8-naphthyridine-3-carboxamide (XZ365)

Purification by preparative HPLC (as indicated in the General Synthetic Procedures using a 00G-4436-P0-AX column with a linear gradient of 20% B to 80% B over 30 minutes; retention time=26.4 minutes), fluffy solid XZ365 was afforded. ESI-MS m/z: 364.0 (M+H⁺).

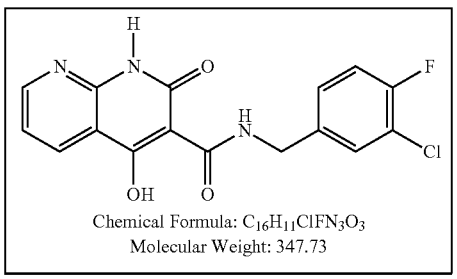 [SMILES: O=C(NCc1ccc(F)c(Cl)c1)c1c(O)c2cccnc2[nH]c1=O]

Compound N-(3-chloro-4-fluorobenzyl)-4-hydroxy-2-oxo-1,2-dihydro-1,8-naphthyridine-3-carboxamide (XZ366)

Purification by preparative HPLC (as indicated in the General Synthetic Procedures using a 00G-4436-P0-AX column with a linear gradient of 20% B to 80% B over 30 minutes; retention time=30.7 minutes), fluffy solid XZ366 was afforded. ESI-MS m/z: 348.0 (M+H⁺).

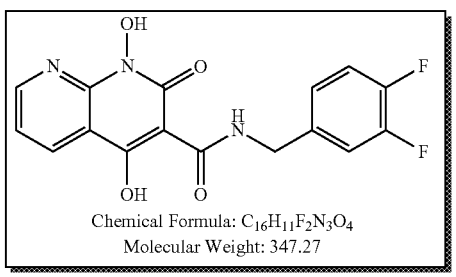

Compound N-(3,4-difluorobenzyl)-1,4-dihydroxy-2-oxo-1,2-dihydro-1,8-naphthyridine-3-carboxamide (XZ367)

Purification by preparative HPLC (as indicated in the General Synthetic Procedures using a 00G-4436-P0-AX column with a linear gradient of 40% B to 90% B over 30 minutes; retention time=22.2 minutes), fluffy solid XZ367 was afforded. ESI-MS m/z: 348.0 (M+H⁺).

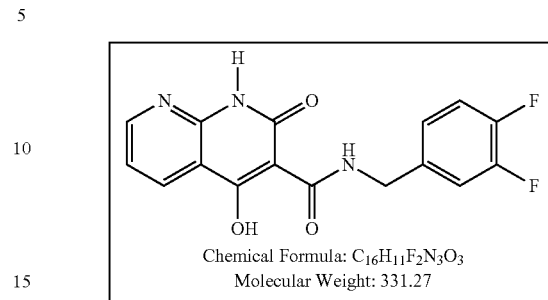

Compound N-(3,4-difluorobenzyl)-4-hydroxy-2-oxo-1,2-dihydro-1,8-naphthyridine-3-carboxamide (XZ368)

Purification by preparative HPLC (as indicated in the General Synthetic Procedures using a 00G-4436-P0-AX column with a linear gradient of 40% B to 90% B over 30 minutes; retention time=27.4 minutes), fluffy solid XZ368 was afforded. ESI-MS m/z: 332.1 (M+H⁺).

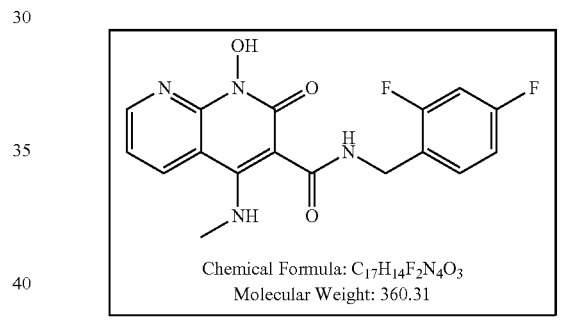

Compound N-(2,4-difluorobenzyl)-1-hydroxy-4-(methylamino)-2-oxo-1,2-dihydro-1,8-naphthyridine-3-carboxamide (XZ371)

Purification by preparative HPLC (as indicated in the General Synthetic Procedures using a 00G-4436-P0-AX column with a linear gradient of 20% B to 50% B over 30 minutes; retention time=26.4 minutes), fluffy solid XZ371 was afforded. ESI-MS m/z: 361.1 (M+H⁺).

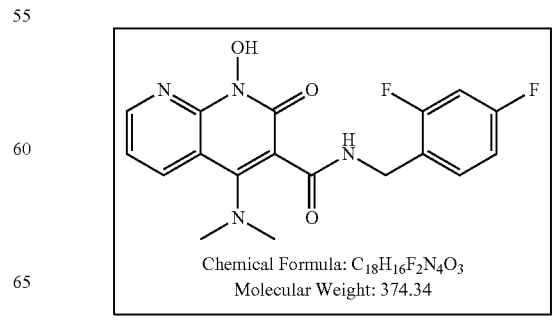

Compound N-(2,4-difluorobenzyl)-4-(dimethylamino)-1-hydroxy-2-oxo-1,2-dihydro-1,8-naphthyridine-3-carboxamide (XZ372)

Purification by preparative HPLC (as indicated in the General Synthetic Procedures using a 00G-4436-P0-AX column with a linear gradient of 20% B to 45% B over 30 minutes; retention time=21.6 minutes), fluffy solid XZ372 was afforded. ESI-MS m/z: 375.1 (M+H$^+$).

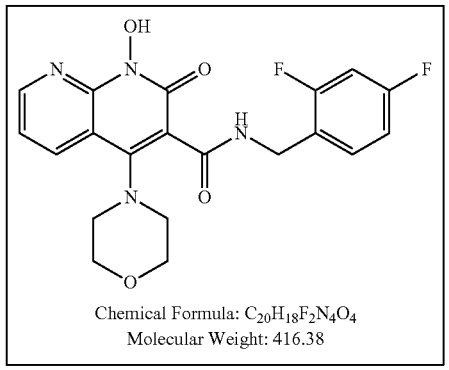 [SMILES: O=C(NCc1ccc(F)cc1F)c1c(N2CCOCC2)c2cccnc2n(O)c1=O]

Chemical Formula: C$_{20}$H$_{18}$F$_2$N$_4$O$_4$
Molecular Weight: 416.38

Compound N-(2,4-difluorobenzyl)-1-hydroxy-4-morpholino-2-oxo-1,2-dihydro-1,8-naphthyridine-3-carboxamide (XZ373)

Purification by preparative HPLC (as indicated in the General Synthetic Procedures using a 00G-4436-P0-AX column with a linear gradient of 20% B to 45% B over 30 minutes; retention time=20.5 minutes), fluffy solid XZ373 was afforded. ESI-MS m/z: 417.1 (M+H$^+$).

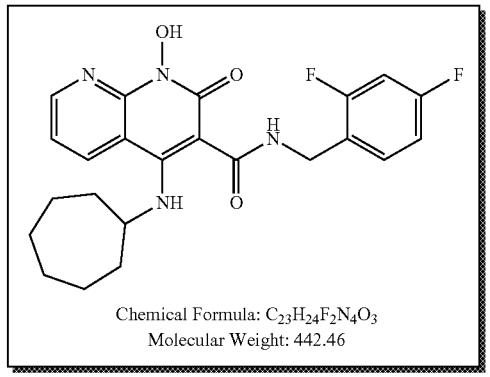

Chemical Formula: C$_{23}$H$_{24}$F$_2$N$_4$O$_3$
Molecular Weight: 442.46

Compound 4-(cycloheptylamino)-N-(2,4-difluorobenzyl)-1-hydroxy-2-oxo-1,2-dihydro-1,8-naphthyridine-3-carboxamide (XZ376)

Purification by preparative HPLC (as indicated in the General Synthetic Procedures using a 00G-4436-P0-AX column with a linear gradient of 40% B to 80% B over 30 minutes; retention time=25.8 minutes), fluffy solid XZ376 was afforded. ESI-MS m/z: 443.1 (M+H$^+$).

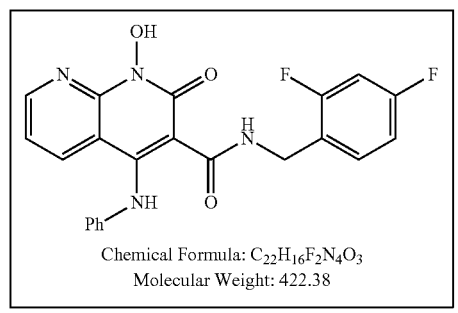 [SMILES: O=C(NCc1ccc(F)cc1F)c1c(Nc2ccccc2)c2cccnc2n(O)c1=O]

Chemical Formula: C$_{22}$H$_{16}$F$_2$N$_4$O$_3$
Molecular Weight: 422.38

Compound N-(2,4-difluorobenzyl)-1-hydroxy-2-oxo-4-(phenylamino)-1,2-dihydro-1,8-naphthyridine-3-carboxamide (XZ377)

Purification by preparative HPLC (as indicated in the General Synthetic Procedures using a 00G-4436-P0-AX column with a linear gradient of 40% B to 90% B over 30 minutes; retention time=20.2 minutes), fluffy solid XZ377 was afforded. ESI-MS m/z: 423.1 (M+H$^+$).

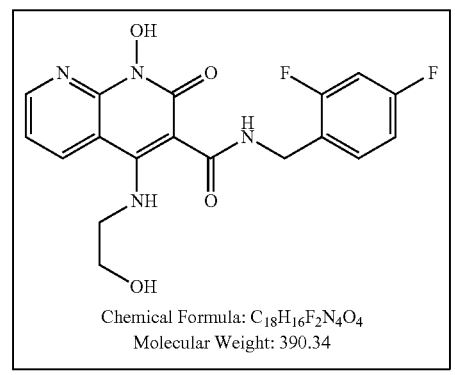 [SMILES: O=C(NCc1ccc(F)cc1F)c1c(NCCO)c2cccnc2n(O)c1=O]

Chemical Formula: C$_{18}$H$_{16}$F$_2$N$_4$O$_4$
Molecular Weight: 390.34

Compound N-(2,4-difluorobenzyl)-1-hydroxy-4-((2-hydroxyethyl)amino)-2-oxo-1,2-dihydro-1,8-naphthyridine-3-carboxamide (XZ378)

Purification by preparative HPLC (as indicated in the General Synthetic Procedures using a 00G-4436-P0-AX column with a linear gradient of 20% B to 50% B over 30 minutes; retention time=21.6 minutes), fluffy solid XZ378 was afforded. ESI-MS m/z: 391.1 (M+H$^+$).

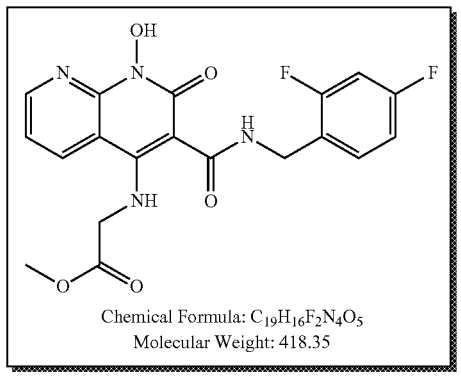

Chemical Formula: C$_{19}$H$_{16}$F$_2$N$_4$O$_5$
Molecular Weight: 418.35

Compound Methyl 2-((3-((2,4-difluorobenzyl)carbamoyl)-1-hydroxy-2-oxo-1,2-dihydro-1,8-naphthyridin-4-yl)amino)acetate (XZ379)

Purification by preparative HPLC (as indicated in the General Synthetic Procedures using a 00G-4436-P0-AX column with a linear gradient of 20% B to 50% B over 30 minutes; retention time=28.4 minutes), white fluffy solid XZ379 was afforded. $^1$H NMR (400 MHz, DMSO-d$^6$) δ 10.43 (brs, 1H), 10.09 (t, J=5.7 Hz, 1H), 8.62 (dd, J=4.5, 1.3 Hz, 1H), 8.43 (dd, J=8.2, 1.4 Hz, 1H), 7.50 (dd, J=15.5, 8.7 Hz, 1H), 7.25 (dd, J=8.2, 4.6 Hz, 1H), 7.20-7.12 (m, 1H), 7.00 (td, J=8.2, 2.4 Hz, 1H), 4.42 (s, 2H), 4.41 (s, 2H), 3.60 (s, 3H). ESI-MS m/z: 419.1 (M+H$^+$).

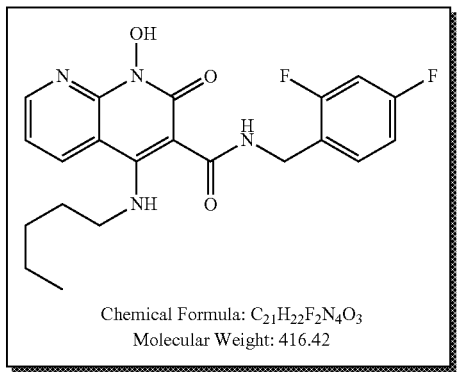

Chemical Formula: C$_{21}$H$_{22}$F$_2$N$_4$O$_3$
Molecular Weight: 416.42

Compound N-(2,4-difluorobenzyl)-1-hydroxy-2-oxo-4-(pentylamino)-1,2-dihydro-1,8-naphthyridine-3-carboxamide (XZ380)

Purification by preparative HPLC (as indicated in the General Synthetic Procedures using a 00G-4436-P0-AX column with a linear gradient of 40% B to 80% B over 30 minutes; retention time=23.7 minutes), fluffy solid XZ380 was afforded. ESI-MS m/z: 417.1 (M+H$^+$).

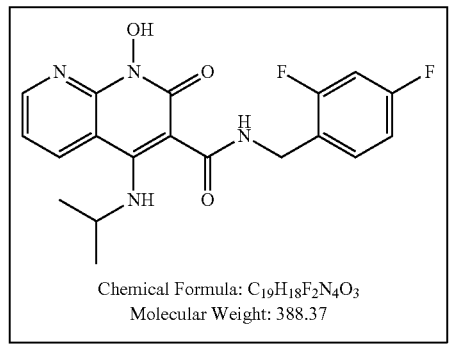 [SMILES: CC(C)Nc1c(C(=O)NCc2ccc(F)cc2F)c(=O)n(O)c2ncccc12]

Chemical Formula: C$_{19}$H$_{18}$F$_2$N$_4$O$_3$
Molecular Weight: 388.37

Compound N-(2,4-difluorobenzyl)-1-hydroxy-4-(isopropylamino)-2-oxo-1,2-dihydro-1,8-naphthyridine-3-carboxamide (XZ381)

Purification by preparative HPLC (as indicated in the General Synthetic Procedures using a 00G-4436-P0-AX column with a linear gradient of 40% B to 80% B over 30 minutes; retention time=17.0 minutes), fluffy solid XZ381 was afforded. ESI-MS m/z: 389.1 (M+H$^+$).

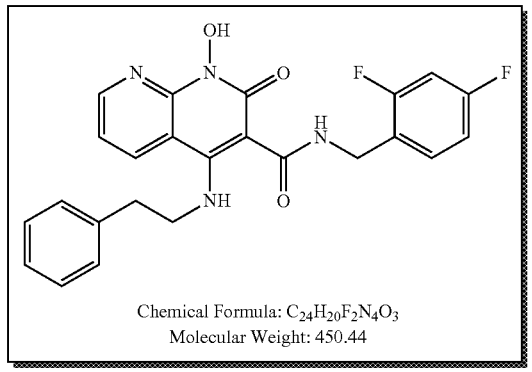

Chemical Formula: C$_{24}$H$_{20}$F$_2$N$_4$O$_3$
Molecular Weight: 450.44

Compound N-(2,4-difluorobenzyl)-1-hydroxy-2-oxo-4-(phenethylamino)-1,2-dihydro-1,8-naphthyridine-3-carboxamide (XZ382)

Purification by preparative HPLC (as indicated in the General Synthetic Procedures using a 00G-4436-P0-AX column with a linear gradient of 40% B to 80% B over 30 minutes; retention time=22.0 minutes), fluffy solid XZ382 was afforded. ESI-MS m/z: 451.1 (M+H$^+$).

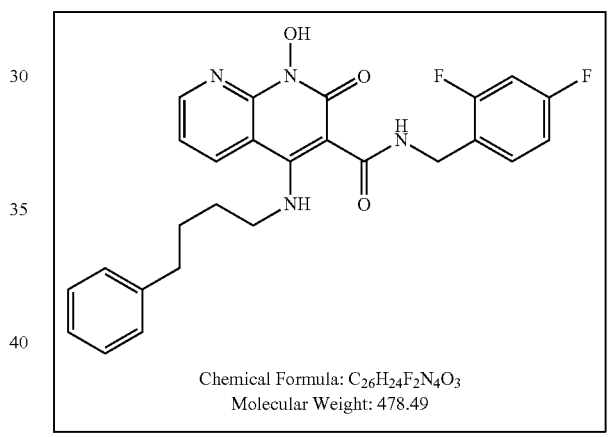

Chemical Formula: C$_{26}$H$_{24}$F$_2$N$_4$O$_3$
Molecular Weight: 478.49

Compound N-(2,4-difluorobenzyl)-1-hydroxy-2-oxo-4-((4-phenylbutyl)amino)-1,2-dihydro-1,8-naphthyridine-3-carboxamide (XZ383)

Purification by preparative HPLC (as indicated in the General Synthetic Procedures using a 00G-4436-P0-AX column with a linear gradient of 40% B to 80% B over 30 minutes; retention time=26.7 minutes), fluffy solid XZ383 was afforded. ESI-MS m/z: 479.2 (M+H$^+$).

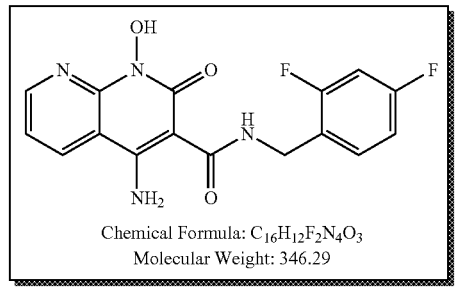

Chemical Formula: C$_{16}$H$_{12}$F$_2$N$_4$O$_3$
Molecular Weight: 346.29

Compound 4-Amino-N-(2,4-difluorobenzyl)-1-hydroxy-2-oxo-1,2-dihydro-1,8-naphthyridine-3-carboxamide (XZ384)

Purification by preparative HPLC (as indicated in the General Synthetic Procedures using a 00G-4436-P0-AX column with a linear gradient of 30% B to 50% B over 30 minutes; retention time=19.5 minutes), white fluffy solid XZ384 was afforded. $^1$H NMR (400 MHz, DMSO-d$^6$) δ 10.59 (t, J=5.8 Hz, 1H), 8.66 (dd, J=4.5, 1.4 Hz, 1H), 8.61 (dd, J=8.1, 1.6 Hz, 1H), 7.36 (d, J=6.6 Hz, 1H), 7.30 (dd, J=8.1, 4.6 Hz, 1H), 7.18 (d, J=9.2 Hz, 1H), 7.00 (d, J=2.4 Hz, 1H), 4.46 (d, J=5.8 Hz, 2H). ESI-MS m/z: 347.1 (M+H$^+$).

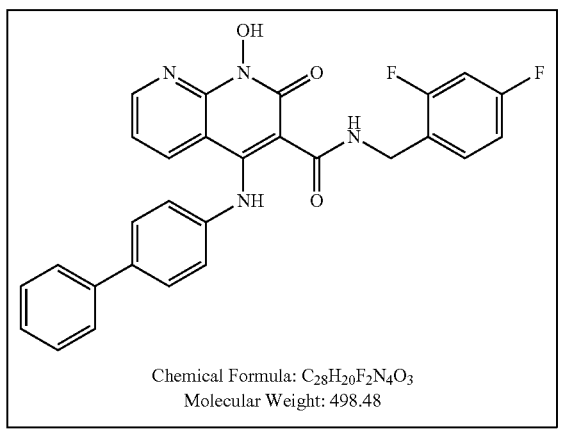 [SMILES: O=C(NCc1ccc(F)cc1F)c1c(Nc2ccc(-c3ccccc3)cc2)c2cccnc2n(O)c1=O]

Chemical Formula: C$_{28}$H$_{20}$F$_2$N$_4$O$_3$
Molecular Weight: 498.48

Compound 4-([1,1'-biphenyl]-4-ylamino)-N-(2,4-difluorobenzyl)-1-hydroxy-2-oxo-1,2-dihydro-1,8-naphthyridine-3-carboxamide (XZ385)

Purification by preparative HPLC (as indicated in the General Synthetic Procedures using a 00G-4436-P0-AX column with a linear gradient of 50% B to 90% B over 30 minutes; retention time=22.8 minutes), fluffy solid XZ385 was afforded. ESI-MS m/z: 499.1 (M+H$^+$).

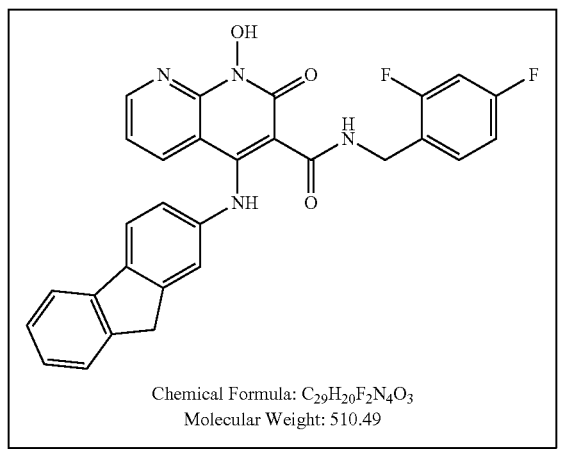 [SMILES: O=C(NCc1ccc(F)cc1F)c1c(Nc2ccc3c(c2)Cc2ccccc2-3)c2cccnc2n(O)c1=O]

Chemical Formula: C$_{29}$H$_{20}$F$_2$N$_4$O$_3$
Molecular Weight: 510.49

Compound 4-((9H-fluoren-2-yl)amino)-N-(2,4-difluorobenzyl)-1-hydroxy-2-oxo-1,2-dihydro-1,8-naphthyridine-3-carboxamide (XZ386)

Purification by preparative HPLC (as indicated in the General Synthetic Procedures using a 00G-4436-P0-AX column with a linear gradient of 60% B to 80% B over 30 minutes; retention time=21.3 minutes), fluffy solid XZ386 was afforded. ESI-MS m/z: 511.1 (M+H$^+$).

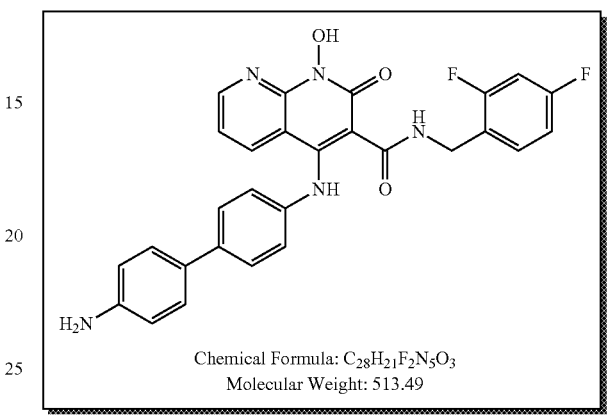

Chemical Formula: C$_{28}$H$_{21}$F$_2$N$_5$O$_3$
Molecular Weight: 513.49

Compound 4-((4'-amino-[1,1'-biphenyl]-4-yl)amino)-N-(2,4-difluorobenzyl)-1-hydroxy-2-oxo-1,2-dihydro-1,8-naphthyridine-3-carboxamide (XZ387)

Purification by preparative HPLC (as indicated in the General Synthetic Procedures using a 00G-4436-P0-AX column with a linear gradient of 30% B to 70% B over 30 minutes; retention time=15.6 minutes), fluffy solid XZ387 was afforded. ESI-MS m/z: 514.1 (M+H$^+$).

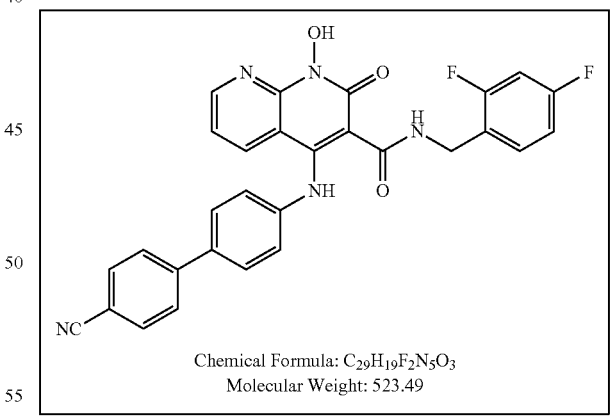

Chemical Formula: C$_{29}$H$_{19}$F$_2$N$_5$O$_3$
Molecular Weight: 523.49

Compound 4-((4'-cyano-[1,1'-biphenyl]-4-yl)amino)-N-(2,4-difluorobenzyl)-1-hydroxy-2-oxo-1,2-dihydro-1,8-naphthyridine-3-carboxamide (XZ388)

Purification by preparative HPLC (as indicated in the General Synthetic Procedures using a 00G-4436-P0-AX column with a linear gradient of 30% B to 80% B over 30 minutes; retention time=22.3 minutes), fluffy solid XZ388 was afforded. ESI-MS m/z: 524.1 (M+H$^+$).

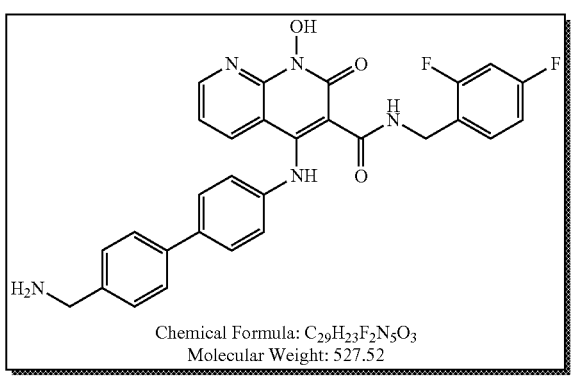

Compound 4-((4'-(aminomethyl)-[1,1'-biphenyl]-4-yl)amino)-N-(2,4-difluorobenzyl)-1-hydroxy-2-oxo-1,2-dihydro-1,8-naphthyridine-3-carboxamide (XZ389)

Purification by preparative HPLC (as indicated in the General Synthetic Procedures using a 00G-4436-P0-AX column with a linear gradient of 30% B to 80% B over 30 minutes; retention time=26.2 minutes), fluffy solid XZ389 was afforded. ESI-MS m/z: 528.2 (M+H$^+$).

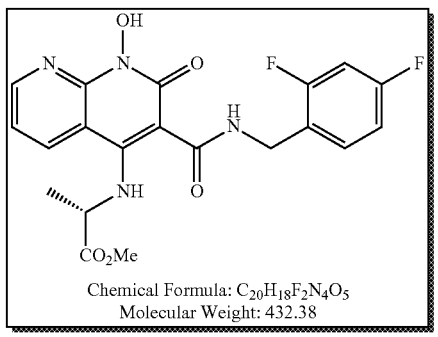

Compound (S)-methyl 2-((3-((2,4-difluorobenzyl)carbamoyl)-1-hydroxy-2-oxo-1,2-dihydro-1,8-naphthyridin-4-yl)amino)propanoat (XZ394)

Purification by preparative HPLC (as indicated in the General Synthetic Procedures using a 00G-4436-P0-AX column with a linear gradient of 30% B to 50% B over 30 minutes; retention time=26.4 minutes), fluffy solid XZ394 was afforded. ESI-MS m/z: 433.1 (M+H$^+$).

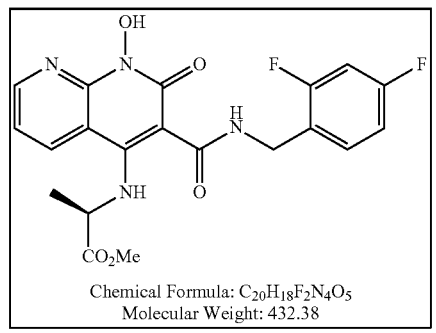 [SMILES: COC(=O)[C@@H](C)Nc1c(C(=O)NCc2ccc(F)cc2F)c(=O)n(O)c2ncccc12]

Compound (R)-methyl 2-((3-((2,4-difluorobenzyl)carbamoyl)-1-hydroxy-2-oxo-1,2-dihydro-1,8-naphthyridin-4-yl)amino)propanoat (XZ395)

Purification by preparative HPLC (as indicated in the General Synthetic Procedures using a 00G-4436-P0-AX column with a linear gradient of 30% B to 50% B over 30 minutes; retention time=26.1 minutes), fluffy solid XZ395 was afforded. ESI-MS m/z: 433.1 (M+H$^+$).

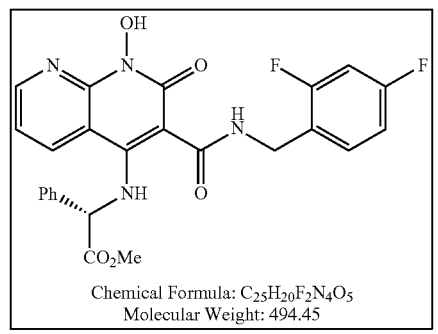 [SMILES: COC(=O)[C@@H](Nc1c(C(=O)NCc2ccc(F)cc2F)c(=O)n(O)c2ncccc12)c1ccccc1]

Compound (S)-methyl 2-((3-((2,4-difluorobenzyl)carbamoyl)-1-hydroxy-2-oxo-1,2-dihydro-1,8-naphthyridin-4-yl)amino)-2-phenylacetate (XZ396)

Purification by preparative HPLC (as indicated in the General Synthetic Procedures using a 00G-4436-P0-AX column with a linear gradient of 40% B to 70% B over 30 minutes; retention time=22.59 minutes), fluffy solid XZ396 was afforded. ESI-MS m/z: 479.1 (M+H$^+$).

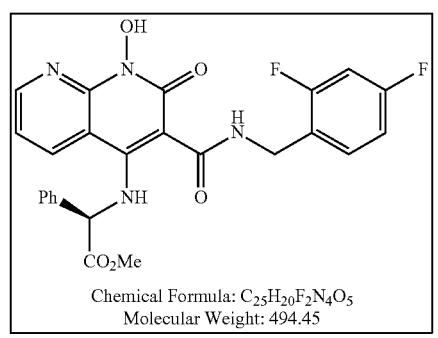 [SMILES: COC(=O)[C@H](Nc1c(C(=O)NCc2ccc(F)cc2F)c(=O)n(O)c2ncccc12)c1ccccc1]

Compound (R)-methyl 2-((3-((2,4-difluorobenzyl)carbamoyl)-1-hydroxy-2-oxo-1,2-dihydro-1,8-naphthyridin-4-yl)amino)-2-phenylacetate (XZ397)

Purification by preparative HPLC (as indicated in the General Synthetic Procedures using a 00G-4436-P0-AX column with a linear gradient of 40% B to 60% B over 30 minutes; retention time=26.3 minutes), fluffy solid XZ397 was afforded. ESI-MS m/z: 495.1 (M+H$^+$).

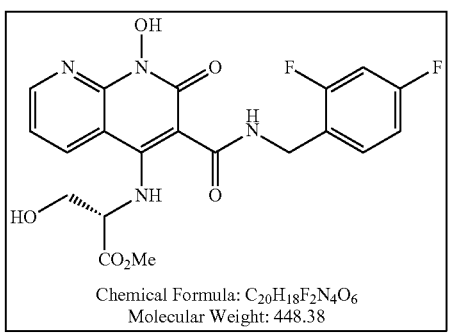 [SMILES: COC(=O)[C@H](CO)Nc1c(C(=O)NCc2ccc(F)cc2F)c(=O)n(O)c2ncccc12]

Compound (S)-methyl 2-((3-((2,4-difluorobenzyl)carbamoyl)-1-hydroxy-2-oxo-1,2-dihydro-1,8-naphthyridin-4-yl)amino)-3-hydroxypropanoate (XZ398)

Purification by preparative HPLC (as indicated in the General Synthetic Procedures using a 00G-4436-P0-AX column with a linear gradient of 30% B to 50% B over 30 minutes; retention time=15.9 minutes), fluffy solid XZ398 was afforded. ESI-MS m/z: 449.1 (M+H$^+$).

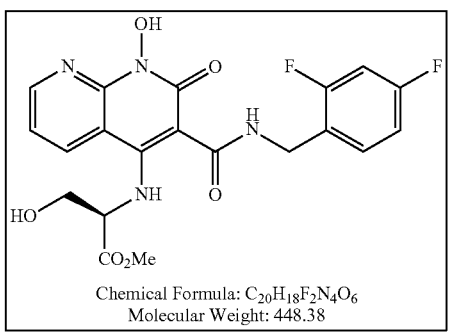 [SMILES: COC(=O)[C@@H](CO)Nc1c(C(=O)NCc2ccc(F)cc2F)c(=O)n(O)c2ncccc12]

Compound (R)-methyl 2-((3-((2,4-difluorobenzyl)carbamoyl)-1-hydroxy-2-oxo-1,2-dihydro-1,8-naphthyridin-4-yl)amino)-3-hydroxypropanoate (XZ399)

Purification by preparative HPLC (as indicated in the General Synthetic Procedures using a 00G-4436-P0-AX column with a linear gradient of 25% B to 50% B over 30 minutes; retention time=20.5 minutes), fluffy solid XZ399 was afforded. ESI-MS m/z: 449.1 (M+H$^+$).

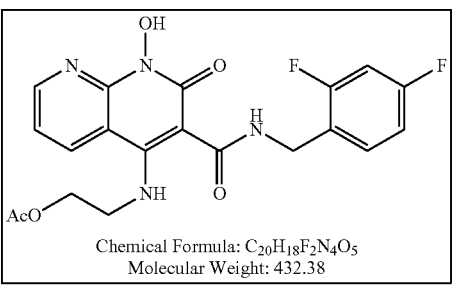 [SMILES: CC(=O)OCCNc1c(C(=O)NCc2ccc(F)cc2F)c(=O)n(O)c2ncccc12]

Compound 2-((3-((2,4-difluorobenzyl)carbamoyl)-1-hydroxy-2-oxo-1,2-dihydro-1,8-naphthyridin-4-yl)amino)ethyl acetate (XZ402)

Purification by preparative HPLC (as indicated in the General Synthetic Procedures using a 00G-4436-P0-AX column with a linear gradient of 30% B to 50% B over 30 minutes; retention time=23.6 minutes), fluffy solid XZ402 was afforded. ESI-MS m/z: 433.1 (M+H$^+$).

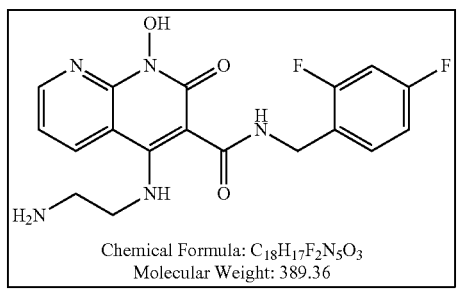 [SMILES: NCCNc1c(C(=O)NCc2ccc(F)cc2F)c(=O)n(O)c2ncccc12]

Compound 4-((2-aminoethyl)amino)-N-(2,4-difluorobenzyl)-1-hydroxy-2-oxo-1,2-dihydro-1,8-naphthyridine-3-carboxamide (XZ403)

Purification by preparative HPLC (as indicated in the General Synthetic Procedures using a 00G-4436-P0-AX column with a linear gradient of 0% B to 40% B over 30 minutes; retention time=25.9 minutes), fluffy solid XZ403 was afforded. ESI-MS m/z: 390.1 (M+H$^+$).

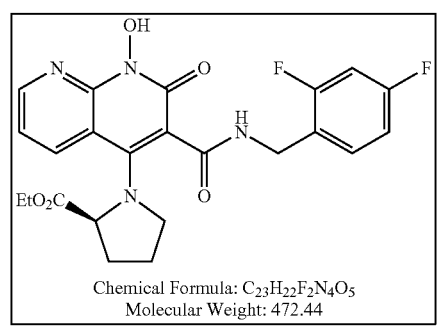 [SMILES: CCOC(=O)[C@@H]1CCCN1c1c(C(=O)NCc2ccc(F)cc2F)c(=O)n(O)c2ncccc12]

Compound (S)-ethyl 1-(3-((2,4-difluorobenzyl)carbamoyl)-1-hydroxy-2-oxo-1,2-dihydro-1,8-naphthyridin-4-yl)pyrrolidine-2-carboxylate (XZ404)

Purification by preparative HPLC (as indicated in the General Synthetic Procedures using a 00G-4436-P0-AX column with a linear gradient of 40% B to 70% B over 30 minutes; retention time=12.5 minutes), fluffy solid XZ404 was afforded. ESI-MS m/z: 473.2 (M+H$^+$).

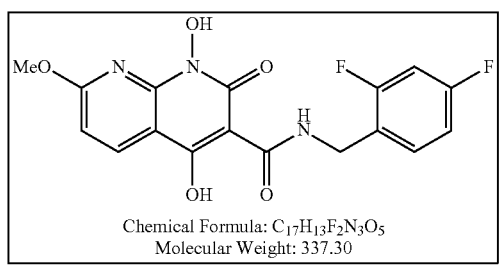 [SMILES: COc1ccc2c(O)c(C(=O)NCc3ccc(F)cc3F)c(=O)n(O)c2n1]

Compound N-(2,4-difluorobenzyl)-1,4-dihydroxy-7-methoxy-2-oxo-1,2-dihydro-1,8-naphthyridine-3-carboxamide (XZ405)

Purification by preparative HPLC (as indicated in the General Synthetic Procedures using a 00G-4436-P0-AX column with a linear gradient of 30% B to 90% B over 30 minutes; retention time=25.5 minutes), fluffy solid XZ405 was afforded. ESI-MS m/z: 378.1 (M+H$^+$).

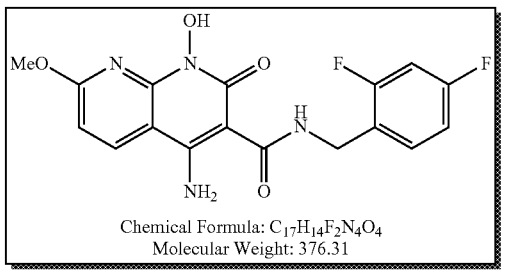

Compound 4-amino-N-(2,4-difluorobenzyl)-1-hydroxy-7-methoxy-2-oxo-1,2-dihydro-1,8-naphthyridine-3-carboxamide (XZ406)

Purification by preparative HPLC (as indicated in the General Synthetic Procedures using a 00G-4436-P0-AX column with a linear gradient of 30% B to 75% B over 30 minutes; retention time=22.35 minutes), fluffy solid XZ406 was afforded. ESI-MS m/z: 377.1 (M+H$^+$).

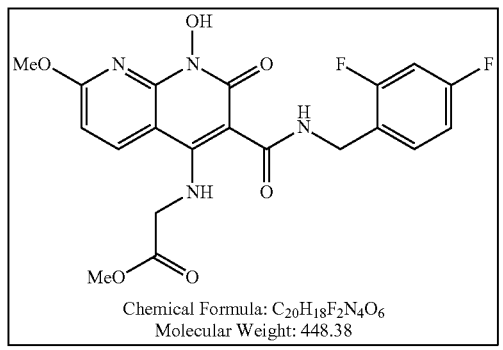 [SMILES: COC(=O)CNc1c(C(=O)NCc2ccc(F)cc2F)c(=O)n(O)c2nc(OC)ccc12]

Compound methyl 2-((3-((2,4-difluorobenzyl)carbamoyl)-1-hydroxy-7-methoxy-2-oxo-1,2-dihydro-1,8-naphthyridin-4-yl)amino)acetate (XZ407)

Purification by preparative HPLC (as indicated in the General Synthetic Procedures using a 00G-4436-P0-AX column with a linear gradient of 30% B to 80% B over 30 minutes; retention time=23.7 minutes), fluffy solid XZ407 was afforded. ESI-MS m/z: 449.1 (M+H$^+$).

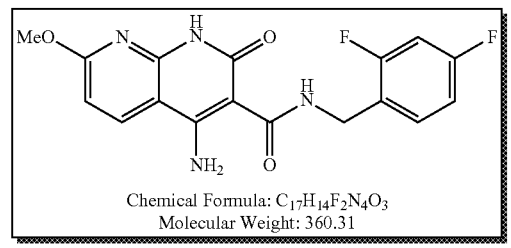

Compound 4-amino-N-(2,4-difluorobenzyl)-7-methoxy-2-oxo-1,2-dihydro-1,8-naphthyridine-3-carboxamide (XZ408)

Purification by preparative HPLC (as indicated in the General Synthetic Procedures using a 00G-4436-P0-AX column with a linear gradient of 30% B to 75% B over 30 minutes; retention time=24.5 minutes), fluffy solid XZ408 was afforded. ESI-MS m/z: 361.1 (M+H$^+$).

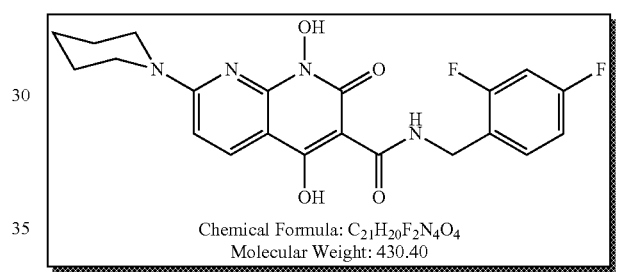

Compound N-(2,4-difluorobenzyl)-1,4-dihydroxy-2-oxo-7-(piperidin-1-yl)-1,2-dihydro-1,8-naphthyridine-3-carboxamide (XZ409)

Purification by preparative HPLC (as indicated in the General Synthetic Procedures using a 00G-4436-P0-AX column with a linear gradient of 50% B to 90% B over 30 minutes; retention time=24.0 minutes), fluffy solid XZ409 was afforded. ESI-MS m/z: 431.2 (M+H$^+$).

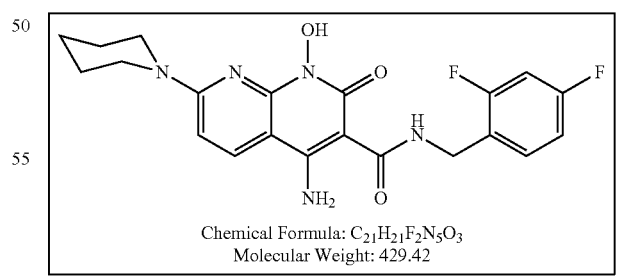

Compound 4-amino-N-(2,4-difluorobenzyl)-1-hydroxy-2-oxo-7-(piperidin-1-yl)-1,2-dihydro-1,8-naphthyridine-3-carboxamide (XZ410)

Purification by preparative HPLC (as indicated in the General Synthetic Procedures using a 00G-4436-P0-AX column with a linear gradient of 50% B to 70% B over 30 minutes; retention time=20.6 minutes), fluffy solid XZ410 was afforded. ESI-MS m/z: 430.2 (M+H$^+$).

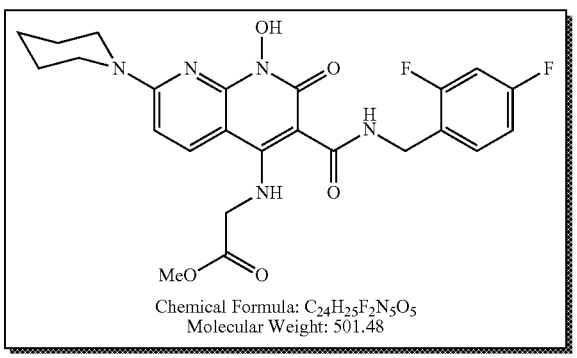

Compound methyl 2-((3-((2,4-difluorobenzyl)carbamoyl)-1-hydroxy-2-oxo-7-(piperidin-1-yl)-1,2-dihydro-1,8-naphthyridin-4-yl)amino)acetate (XZ411)

Purification by preparative HPLC (as indicated in the General Synthetic Procedures using a 00G-4436-P0-AX column with a linear gradient of 50% B to 70% B over 30 minutes; retention time=22.9 minutes), fluffy solid XZ411 was afforded. ESI-MS m/z: 502.2 (M+H$^+$).

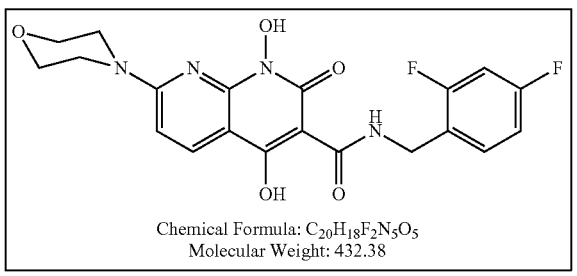 [SMILES: O=C(NCc1ccc(F)cc1F)c1c(O)c2ccc(N3CCOCC3)nc2n(O)c1=O]

Compound N-(2,4-difluorobenzyl)-1,4-dihydroxy-7-morpholino-2-oxo-1,2-dihydro-1,8-naphthyridine-3-carboxamide (XZ412)

Purification by preparative HPLC (as indicated in the General Synthetic Procedures using a 00G-4436-P0-AX column with a linear gradient of 30% B to 90% B over 30 minutes; retention time=24.3 minutes), fluffy solid XZ412 was afforded. ESI-MS m/z: 433.1 (M+H$^+$).

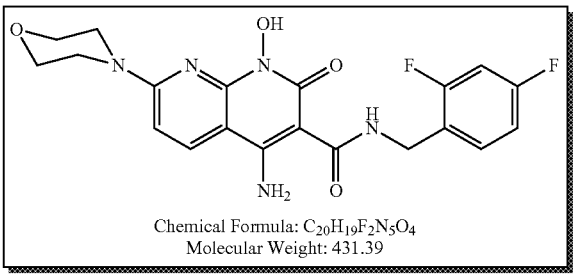

Compound 4-amino-N-(2,4-difluorobenzyl)-1-hydroxy-7-morpholino-2-oxo-1,2-dihydro-1,8-naphthyridine-3-carboxamide (XZ413)

Purification by preparative HPLC (as indicated in the General Synthetic Procedures using a 00G-4436-P0-AX column with a linear gradient of 30% B to 65% B over 30 minutes; retention time=24.0 minutes), fluffy solid XZ413 was afforded. ESI-MS m/z: 432.1 (M+H$^+$).

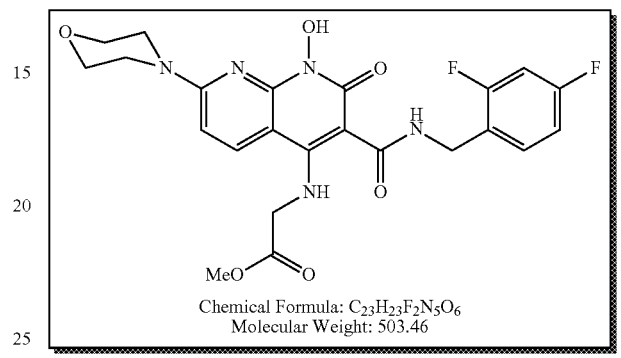

Compound methyl 2-((3-((2,4-difluorobenzyl)carbamoyl)-1-hydroxy-7-morpholino-2-oxo-1,2-dihydro-1,8-naphthyridin-4-yl)amino)acetate (XZ414)

Purification by preparative HPLC (as indicated in the General Synthetic Procedures using a 00G-4436-P0-AX column with a linear gradient of 30% B to 70% B over 30 minutes; retention time=26.0 minutes), fluffy solid XZ414 was afforded. ESI-MS m/z: 504.2 (M+H$^+$).

General Synthesis for Compounds 1-Hydroxy-2-oxo-1,2-dihydro-1,8-naphthyridine-3-carboxamide analogues Scheme 3. General synthesis of 1-hydroxy-2-oxo-1,2-dihydro-1,8-naphthyridine-3-carboxamide analogues.

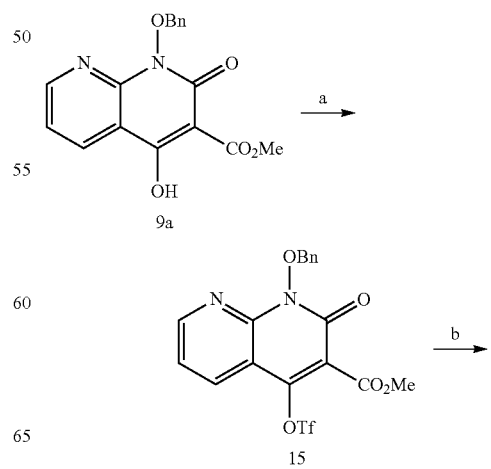

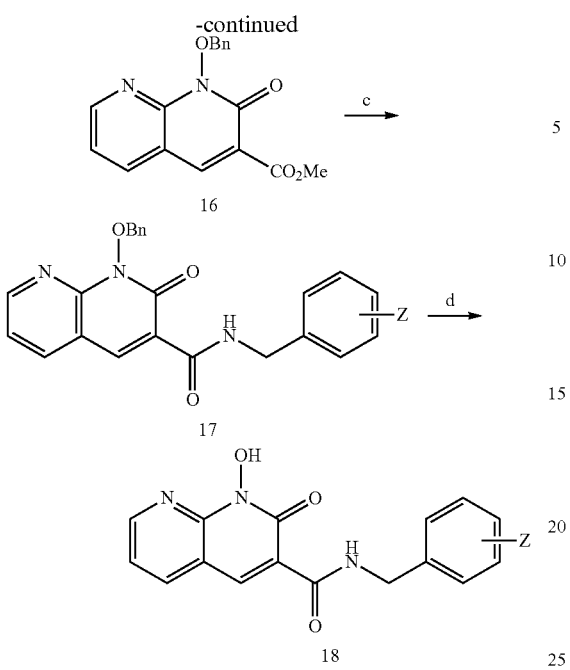

Reagents and conditions: a) Tf₂O; b) PdCl₂(PPh₃)₂, TIS, TEA; c) ZBnNH₂, DMF; d) H₂, Pd/C.

Preparation of Methyl 1-(benzyloxy)-2-oxo-4-(((trifluoromethyl)sulfonyl)oxy)-1,2-dihydro-1,8-naphthyridine-3-carboxylate (15)

Methyl 1-(benzyloxy)-4-hydroxy-2-oxo-1,2-dihydro-1,8-naphthyridine-3-carboxylate (9a) (268 mg, 0.82 mmol) was dissolved in CH₂Cl₂ (15 ml). Triethylamine (0.27 ml, 1.97 mmol) was added. Trifluoromethanesulfonic anhydride (0.17 ml, 0.98 mmol) was added at 0° C. The solution was stirred at 0° C. for 0.5 hour. The mixture was concentrated and purified by Combiflash. White solid methyl 1-(benzyloxy)-2-oxo-4-(((trifluoromethyl)sulfonyl)oxy)-1,2-dihydro-1,8-naphthyridine-3-carboxylate (15) (301 mg, 80% yield) was afforded.

Preparation of Methyl 1-(benzyloxy)-2-oxo-1,2-dihydro-1,8-naphthyridine-3-carboxylate (16)

Methyl 1-(benzyloxy)-2-oxo-4-(((trifluoromethyl)sulfonyl)oxy)-1,2-dihydro-1,8-naphthyridine-3-carboxylate (15) (34 mg, 0.074 mmol) and PdCl₂(PPh₃)₂(5 mg, 7.37 μmol) was dissolved in DMF (1 mL). Triethylamine (0.030 mL, 0.22 mmol) and triisopropylsilane (17 mg, 0.15 mmol) was added. The mixture was heated to 85° C. for 24 hrs. The crude mixture was purified by Combiflash and eluted with hexanes and ethyl acetate. Methyl 1-(benzyloxy)-2-oxo-1,2-dihydro-1,8-naphthyridine-3-carboxylate (16) (12 mg, 52% yield).

General Procedure M for the Synthesis of 1-(Benzyloxy)-N-(halobenzyl)-2-oxo-1,2-dihydro-1,8-naphthyridine-carboxamides (17)

Ethyl 1-(benzyloxy)-2-oxo-1,2-dihydro-1,8-naphthyridine-3-carboxylate (0.6 mmol) mixed with (halophenyl)methanamine (1 mL). The reaction was heated to 60° C. for 14 hrs. The mixture was extracted by chloroform and washed by HCl (aq., 1N) and brine. After dried over Na₂SO₄, The organic phase was filtered and concentrated. The crude residue was purified by Combiflash and eluted with hexanes and ethyl acetate. Product 1-(benzyloxy)-N-(halobenzyl)-2-oxo-1,2-dihydro-1,8-naphthyridine-3-carboxamides (17) were afforded.

N-(2,4-difluorobenzyl)-1-hydroxy-2-oxo-1,2-dihydro-1,8-naphthyridine-3-carboxamides (18) were prepared from 1-(Benzyloxy)-N-(halobenzyl)-2-oxo-1,2-dihydro-1,8-naphthyridine-3-carboxamides (17) using General Procedure L

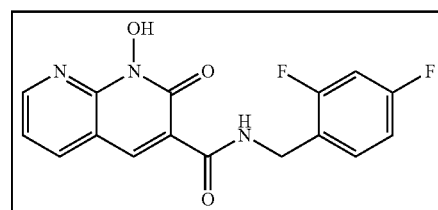

Chemical Formula: C₁₆H₁₁F₂N₃O₃
Molecular Weight: 331.27

Compound N-(2,4-difluorobenzyl)-1-hydroxy-2-oxo-1,2-dihydro-1,8-naphthyridine-3-carboxamide (XZ390)

Purification by preparative HPLC (as indicated in the General Synthetic Procedures using a 00G-4436-P0-AX column with a linear gradient of 20% B to 80% B over 30 minutes; retention time=19.2 minutes), fluffy solid XZ390 was afforded. ESI-MS m/z: 332.1 (M+H⁺).

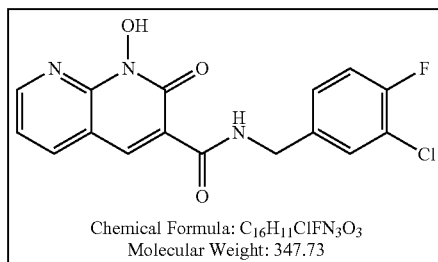

Chemical Formula: C₁₆H₁₁ClFN₃O₃
Molecular Weight: 347.73

Compound N-(3-chloro-4-fluorobenzyl)-1-hydroxy-2-oxo-1,2-dihydro-1,8-naphthyridine-3-carboxamide (XZ391)

Purification by preparative HPLC (as indicated in the General Synthetic Procedures using a 00G-4436-P0-AX column with a linear gradient of 30% B to 50% B over 30 minutes; retention time=22.5 minutes), fluffy solid XZ391 was afforded. ESI-MS m/z: 348.0 (M+H⁺).

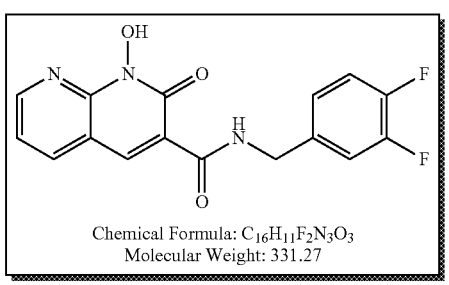

Compound N-(3,4-difluorobenzyl)-1-hydroxy-2-oxo-1,2-dihydro-1,8-naphthyridine-3-carboxamide (XZ392)

Purification by preparative HPLC (as indicated in the General Synthetic Procedures using a 00G-4436-P0-AX column with a linear gradient of 20% B to 50% B over 30 minutes; retention time=26.14 minutes), fluffy solid XZ392 was afforded. ESI-MS m/z: 332.1 (M+H$^+$).

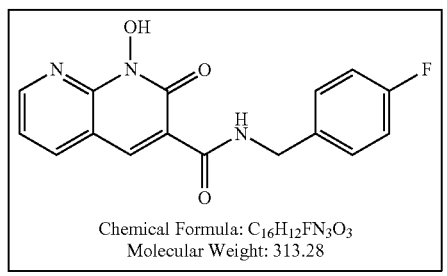 [SMILES: O=C(NCc1ccc(F)cc1)c1cc2cccnc2n(O)c1=O]

Compound N-(4-fluorobenzyl)-1-hydroxy-2-oxo-1,2-dihydro-1,8-naphthyridine-3-carboxamide (XZ393)

Purification by preparative HPLC (as indicated in the General Synthetic Procedures using a 00G-4436-P0-AX column with a linear gradient of 20% B to 50% B over 30 minutes; retention time=24.0 minutes), fluffy solid XZ393 was afforded. ESI-MS m/z: 314.1 (M+H$^+$).

General Synthesis for R$^6$-Substituted Compounds

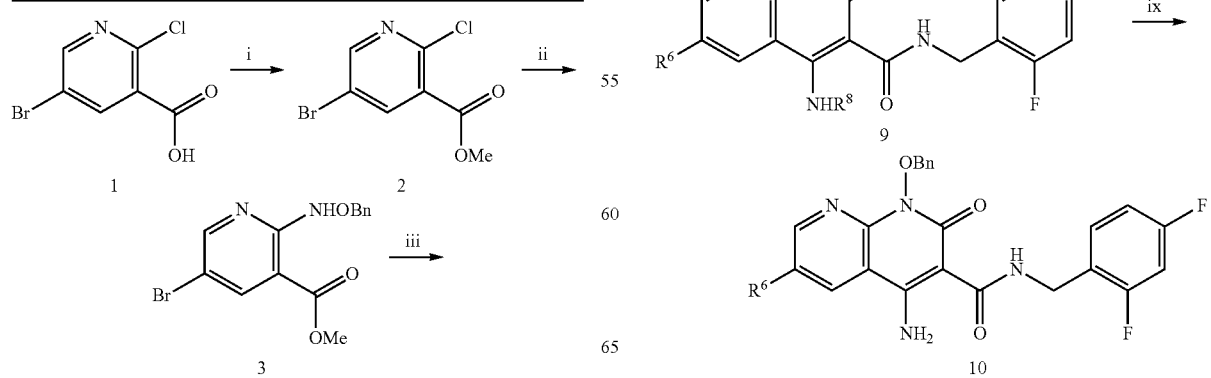

Scheme 2. Preparation of 1-hydroxy-2-oxo-1,2-dihydro-1,8-naphthyridine-3-carboxamide analogues.

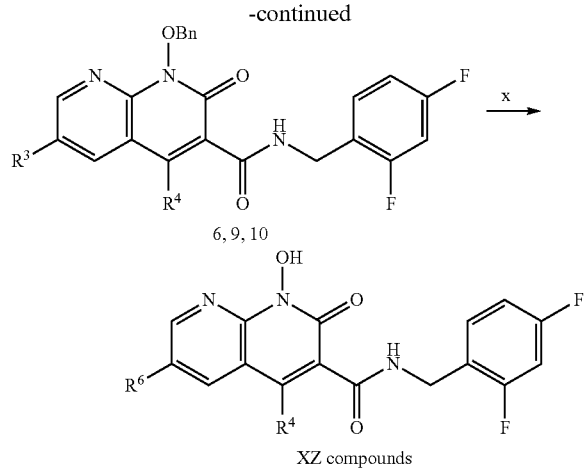

Reagents and conditions: i) H₂SO₄, MeOH; ii) BnONH₂, DMSO; iii) ClCOCH₂CO₂CH₃, TEA, DCM; iv) NaOMe, MeOH; v) 2,4-diF-BnNH₂, DMF; vi) TsCl, TEA, MeCN; vii) R⁸NH₂, DIEA, DMF; viii) ArB(OH)₂, Pd(dppf)Cl₂ (Suzuki Reaction), Cs₂CO₃, toluene; Alkene, Pd(OAc)₂, TEA, PPh₃, (Heck Reaction); or Alkyne, Pd(PPh₃)₂Cl₂, DIEA, CuI (Sonogachira Reaction). ix) TFA, DCM; x) H₂, 10% Pd/C., MeOH.

General Procedure a to Prepare Carboxamides (8)

The solution of 1-(benzyloxy)-6-bromo-3-((2,4-difluorobenzyl)carbamoyl)-2-oxo-1,2-dihydro-1,8-naphthyridin-4-yl 4-methylbenzenesulfonate (7; 0.2 mmol), N-ethyl-N-isopropylpropan-2-amine (2.0 mmol) and amine (1.0 mmol) in DMF (2.0 mL) was heated to 50° C. for 1 hr. The reaction mixture was cooled to room temperature and purified by Combiflash. Compound 4-substituted 1-(benzyloxy)-6-bromo-N-(2,4-difluorobenzyl)-2-oxo-1,2-dihydro-1,8-naphthyridine-3-carboxamide (8) was afforded.

General Procedure B to Prepare Carboxamides (9)

A mixture of 1-(benzyloxy)-6-bromo-N-(2,4-difluorobenzyl)-4-((2,4-dimethoxybenzyl)amino)-2-oxo-1,2-dihydro-1,8-naphthyridine-3-carboxamide (8) (200 mg, 0.30 mmol), Bis(triphenylphosphine)palladium (II) dichloride (6 mg, 9 µmol), N-ethyl-N-isopropylpropan-2-amine (0.05 ml, 0.30 mmol), copper(I) iodide (6 mg, 0.03 mmol) in DMF (1.5 ml) and alkyne (0.45 mmol) was added. The mixture was flushed with argon and sealed with cap. The reaction mixture was heated at 70° C. for 4 hr. The resultant dark mixture was cooled to rt and purified by Combiflash. Compound 6-substituted 1-(benzyloxy)-N-(2,4-difluorobenzyl)-4-((2,4-dimethoxybenzyl)amino)-2-oxo-1,2-dihydro-1,8-naphthyridine-3-carboxamide (9) was afforded.

General Procedure C to Prepare Carboxamides (9)

The mixture of bromide (8) (0.20), alkene (0.40 mmol), triethylamine (0.071 ml, 0.60 mmol), diacetoxypalladium (0.04 mmol), and triphenylphosphine (0.08 mmol) was flushed with argon and sealed in a tube. The reaction mixture was heated using microwave to 100° C. for 5 hrs. The resultant mixture was cooled to rt and purified by Combi-Flash. Solid carboxamide (9) was afforded.

General Procedure D to Prepare Amines (10)

The 2,4-dimethoxybenzylamino protected carboxamide (9) (0.25 mmol) was dissolved in DCM (2 mL). TFA (2 mL) was added at rt. The solvent was evaporated using rotavapor and the residue was purified by CombiFlash. Amine (10) was afforded.

General Procedure E to prepare 4-amino-N-(2,4-difluorobenzyl)-1-hydroxy-6-(5-hydroxypentyl)-2-oxo-1,2-dihydro-1,8-naphthyridine-3-carboxamides (11)

Carboxamide (6, 9 or 10) (0.1 mmol) was suspended in methanol (10 mL) and ethyl acetate (3 mL). Pd/C (30 mg, 10%) was added. The reaction mixture was stirred at rt under hydrogen. When the starting material disappeared from TLC, the mixture was filtered and washed by methanol. The filtrate was concentrated. The resulting yellow residue was redissolved in DMF and purified by HPLC. Fluffy solid (11) was afforded.

Methyl 5-bromo-2-chloronicotinate (2)

Sulfuric acid (2 mL, 52.1 mmol) was added to the suspension of 5-bromo-2-chloronicotinic acid (1) (12.3 g, 52 mmol) was in methanol (100 mL). The mixture was stirred and refluxed for 15 hours. The solvent was evaporated and the residue was neutralized with saturated aqueous NaHCO₃ (aq.). The result suspension was filtered and the solid was washed by water and dried by pump. Methyl 5-bromo-2-chloronicotinate (2) (11.6 g, 89% yield) was afforded. ¹H NMR (400 MHz, CDCl₃) δ 8.53 (d, J=2.4 Hz, 1H), 8.25 (d, J=2.4 Hz, 1H), 3.93 (s, 3H). ¹³C NMR (101 MHz, CDCl₃) δ 163.58, 152.75, 148.61, 142.49, 127.64, 118.57, 53.10. ESI-MS m/z: 251.9 (M+H⁺).

Methyl 2-((benzyloxy)amino)-5-bromonicotinate (3)

The solution of methyl 5-bromo-2-chloronicotinate (2) (2.01 g, 8.02 mmol) in O-benzylhydroxylamine (4.67 mL, 40.1 mmol) was heated at 110° C. overnight. The reaction mixture was cooled to rt and purified by CombiFlash. Colorless oil methyl 2-((benzyloxy)amino)-5-bromonicotinate (3) (1.53 g, 57% yield) was afforded. ¹H NMR (500 MHz, CDCl₃) δ 10.00 (s, 1H), 8.51 (d, J=2.4 Hz, 1H), 8.24 (d, J=2.4 Hz, 1H), 7.47 (dd, J=8.0, 1.2 Hz, 2H), 7.40-7.32 (m, 3H), 5.06 (s, 2H), 3.84 (s, 3H). ¹³C NMR (101 MHz, CDCl₃) δ 165.60, 158.06, 154.29, 141.72, 136.01, 128.91 (2C), 128.48 (2C), 128.41, 108.50, 108.11, 78.14, 52.46. ESI-MS m/z: 337.0, 339.0 (M+H⁺).

Methyl 2-(N-(benzyloxy)-3-methoxy-3-oxopropanamido)-5-bromonicotinate (4)

Methyl 3-chloro-3-oxopropanoate (3) (1.00 ml, 9.04 mmol) was added dropwise to a solution of methyl 2-((benzyloxy)amino)-5-bromonicotinate (1.52 g, 4.52 mmol) and triethylamine (1.27 ml, 9.04 mmol) in CH₂Cl₂ (10 mL). The reaction mixture was stirred at r.t. for 1 hour. The formed mixture was filtered and the filtrate was concentrated. The residue was purified by CombiFlash. Methyl 2-(N-(benzyloxy)-3-methoxy-3-oxopropanamido)-5-bromonicotinate (4) (1.2 g, 61% yield) was afforded. ¹H NMR (400 MHz, CDCl₃) δ 8.63 (s, 1H), 8.24 (d, J=2.1 Hz, 1H), 7.32-7.27 (m, 5H), 4.95 (s, 2H), 3.82 (s, 3H), 3.67 (s, 3H), 3.55 (s, 2H). ¹³C NMR (101 MHz, CDCl₃) δ 170.00, 167.27, 167.01, 164.06, 152.00, 141.66, 133.59, 129.66 (2C), 129.09, 128.50 (2C), 124.78, 118.85, 78.46, 52.63, 52.44, 40.64. ESI-MS m/z: 437.0, 439.0 (M+H⁺).

Methyl 1-(benzyloxy)-6-bromo-4-hydroxy-2-oxo-1,2-dihydro-1,8-naphthyridine-3-carboxylate (5)

Sodium methanolate (1.44 mL, 25% in methanol, 6.32 mmol) was added dropwise to a solution of ethyl 2-(N-(benzyloxy)-3-methoxy-3-oxopropanamido)-5-bromonicotinate (4) (1.14 g, 2.53 mmol) in MeOH (5.0 mL) at rt. The resultant yellow suspension was stirred at rt for 1 hour, the suspension turned to white. The suspension was stirred at rt overnight (19 h). The reaction was brought to pH 4 by the addition of HCl (2N, aq.). After 15 minutes, the formed solids were collected by filtration and washed by water. The white solid was dried by pump. Methyl 1-(benzyloxy)-6-bromo-4-hydroxy-2-oxo-1,2-dihydro-1,8-naphthyridine-3-carboxylate (5) (1.0 g, 98% yield) was afforded. $^1$H NMR (400 MHz, CDCl$_3$) δ 8.76 (d, J=2.4 Hz, 1H), 8.51 (d, J=2.4 Hz, 1H), 7.66-7.63 (m, 2H), 7.37-7.30 (m, 3H), 5.20 (s, 2H), 4.04 (s, 3H). $^{13}$C NMR (101 MHz, CDCl$_3$) δ 172.06, 169.01, 156.03, 155.37, 148.03, 136.42, 133.78, 130.02 (2C), 129.11, 128.41 (2C), 113.94, 110.71, 99.52, 78.30, 53.46. ESI-MS m/z: 405.0, 407.0 (M+H$^+$).

1-(benzyloxy)-6-bromo-N-(2,4-difluorobenzyl)-4-hydroxy-2-oxo-1,2-dihydro-1,8-naphthyridine-3-carboxamide (6)

Methyl 1-(benzyloxy)-6-bromo-4-hydroxy-2-oxo-1,2-dihydro-1,8-naphthyridine-3-carboxylate (5) (2.22 g, 5.48 mmol) and (2,4-difluorophenyl)methanamine (6.51 mL, 54.8 mmol) was mixed in a tube with DMF (3 mL). The solution was heated by Microwave to 140° C. for 2 hrs. The resultant mixture was filtered and washed by methanol. The solid was collected. The filtrate was purified by CombiFlash. The fractions were collected and recrystallized from methanol. Combined the solids, 1-(benzyloxy)-6-bromo-N-(2,4-difluorobenzyl)-4-hydroxy-2-oxo-1,2-dihydro-1,8-naphthyridine-3-carboxamide (6) (2.18 g, 77% yield) was afforded. $^1$H NMR (500 MHz, CDCl$_3$) δ 10.21 (s, 1H), 8.73 (dd, J=2.4, 1.2 Hz, 1H), 8.51 (dd, J=2.3, 1.2 Hz, 1H), 7.62-7.50 (m, 2H), 7.37-7.25 (m, 4H), 6.86-6.71 (m, 2H), 5.18 (s, 2H), 4.59 (d, J=5.9 Hz, 2H). ESI-MS m/z: 516.0, 518.0 (M+H$^+$).

1-(benzyloxy)-6-bromo-3-((2,4-difluorobenzyl)carbamoyl)-2-oxo-1,2-dihydro-1,8-naphthyridin-4-yl 4-methylbenzenesulfonate (7)

Triethylamine (4.38 mL, 31.3 mmol) and 4-methylbenzene-1-sulfonyl chloride (2.98 g, 15.6 mmol) was added to the mixture of 1-(benzyloxy)-6-bromo-N-(2,4-difluorobenzyl)-4-hydroxy-2-oxo-1,2-dihydro-1,8-naphthyridine-3-carboxamide (6) (2.69 g, 5.21 mmol) in CH$_3$CN (6 mL) and DCM (3 mL) at rt. The reaction mixture was stirred at rt overnight. The mixture was purified by Combiflash. Yellow solid 1-(benzyloxy)-6-bromo-3-((2,4-difluorobenzyl)carbamoyl)-2-oxo-1,2-dihydro-1,8-naphthyridin-4-yl 4-methylbenzenesulfonate (7) (2.76 g, 79% yield) was afforded. $^1$H NMR (500 MHz, CDCl$_3$) δ 8.75 (d, J=2.2 Hz, 1H), 8.28 (t, J=5.8 Hz, 1H), 8.03 (d, J=2.2 Hz, 1H), 7.89 (d, J=8.3 Hz, 2H), 7.64 (dd, J=6.6, 2.7 Hz, 2H), 7.49 (dd, J=15.1, 8.5 Hz, 1H), 7.40 (dd, J=5.0, 3.1 Hz, 5H), 6.85 (ddd, J=19.1, 10.0, 4.3 Hz, 2H), 5.29 (s, 2H), 4.59 (d, J=5.9 Hz, 2H), 2.51 (s, 3H). ESI-MS m/z: 670.0, 672.0 (M+H$^+$).

1-(Benzyloxy)-6-bromo-N-(2,4-difluorobenzyl)-4-((2,4-dimethoxybenzyl)amino)-2-oxo-1,2-dihydro-1,8-naphthyridine-3-carboxamide (8a)

According to general procedure A, the title compound was prepared in 89% yield from 1-(benzyloxy)-6-bromo-3-((2,4-difluorobenzyl)carbamoyl)-2-oxo-1,2-dihydro-1,8-naphthyridin-4-yl 4-methylbenzenesulfonate (7). $^1$H NMR (400 MHz, CDCl$_3$) δ 12.05 (t, J=6.2 Hz, 1H), 10.61 (t, J=5.7 Hz, 1H), 8.58 (d, J=2.1 Hz, 1H), 8.34 (d, J=2.2 Hz, 1H), 7.57 (dd, J=7.3, 1.9 Hz, 2H), 7.39-7.22 (m, 4H), 7.17 (dd, J=8.9, 4.3 Hz, 1H), 6.85-6.63 (m, 2H), 6.47-6.34 (m, 2H), 5.15 (s, 2H), 4.64 (d, J=6.3 Hz, 2H), 4.52 (d, J=5.7 Hz, 2H), 3.74 (s, 3H), 3.73 (s, 3H).

Methyl 2-((1-(benzyloxy)-6-bromo-3-((2,4-difluorobenzyl)carbamoyl)-2-oxo-1,2-dihydro-1,8-naphthyridin-4-yl)amino)acetate (8b)

According to general procedure A, the title compound was prepared in 73.6% yield from 1-(benzyloxy)-6-bromo-3-((2,4-difluorobenzyl)carbamoyl)-2-oxo-1,2-dihydro-1,8-naphthyridin-4-yl 4-methylbenzenesulfonate (7). $^1$H NMR (400 MHz, CDCl$_3$) δ 12.05 (t, J=6.2 Hz, 1H), 10.61 (t, J=5.7 Hz, 1H), 8.58 (d, J=2.1 Hz, 1H), 8.34 (d, J=2.2 Hz, 1H), 7.57 (dd, J=7.3, 1.9 Hz, 2H), 7.39-7.22 (m, 4H), 7.17 (dd, J=8.9, 4.3 Hz, 1H), 6.85-6.63 (m, 2H), 6.47-6.34 (m, 2H), 5.15 (s, 2H), 4.64 (d, J=6.3 Hz, 2H), 4.52 (d, J=5.7 Hz, 2H), 3.74 (s, 3H), 3.73 (s, 3H). ESI-MS m/z: 587.1, 589.1 (MH$^+$).

1-(Benzyloxy)-6-bromo-N-(2,4-difluorobenzyl)-4-((2-hydroxyethyl)amino)-2-oxo-1,2-dihydro-1,8-naphthyridine-3-carboxamide (8c)

According to general procedure A, the title compound was prepared in 93% yield from 1-(benzyloxy)-6-bromo-3-((2,4-difluorobenzyl)carbamoyl)-2-oxo-1,2-dihydro-1,8-naphthyridin-4-yl 4-methylbenzenesulfonate (7). $^1$H NMR (500 MHz, CDCl$_3$) δ 11.65 (bs, 1H), 10.65 (bs, 1H), 8.64 (d, J=1.9 Hz, 1H), 8.47 (d, J=1.9 Hz, 1H), 7.58 (d, J=6.1 Hz, 2H), 7.31 (t, J=7.2 Hz, 4H), 6.79-6.73 (m, 2H), 5.15 (s, 2H), 4.55 (d, J=5.6 Hz, 2H), 3.88-3.86 (m, 2H), 3.78-3.75 (m, 2H). ESI-MS m/z: 559.1, 561.1 (MH$^+$).

1-(Benzyloxy)-N-(2,4-difluorobenzyl)-4-((2,4-dimethoxybenzyl)amino)-2-oxo-6-phenyl-1,2-dihydro-1,8-naphthyridine-3-carboxamide (9a)

A mixture of 1-(benzyloxy)-6-bromo-N-(2,4-difluorobenzyl)-4-((2,4-dimethoxybenzyl)amino)-2-oxo-1,2-dihydro-1,8-naphthyridine-3-carboxamide (8a; 147 mg, 0.22 mmol)), Cesium carbonate (288 mg, 0.88 mmol), phenylboronic acid (108 mg, 0.88 mmol) and [1,1'-Bis(diphenylphosphino)ferrocene]dichloropalladium(II) (8 mg, 0.011 mmol) in toluene (2 mL) was flushed with argon and sealed with cap. The sealed mixture tube was heated at 100° C. for 8 hrs. The resultant mixture was purified by CombiFlash. Solid 1-(benzyloxy)-N-(2,4-difluorobenzyl)-4-((2,4-dimethoxybenzyl)amino)-2-oxo-6-phenyl-1,2-dihydro-1,8-naphthyridine-3-carboxamide (9a; 89 mg) was afforded in 61% yield. $^1$H NMR (400 MHz, CDCl$_3$) δ 12.17 (t, J=6.3 Hz, 1H), 10.79 (t, J=5.7 Hz, 1H), 8.87-8.86 (m, 1H), 8.40 (d, J=2.1 Hz, 1H), 7.68 (d, J=7.4 Hz, 2H), 7.39-7.32 (m, 7H), 7.30-7.27 (m, 3H), 6.84-6.76 (m, 2H), 6.45 (s, 2H), 5.27 (s, 2H), 4.77 (d, J=6.5 Hz, 2H), 4.60 (d, J=5.7 Hz, 2H), 3.79 (s, 3H), 3.63 (s, 3H). ESI-MS m/z: 663.2 (MH$^+$).

1-(Benzyloxy)-6-(3-cyclohexylprop-1-yn-1-yl)-N-(2,4-difluorobenzyl)-4-((2,4-dimethoxybenzyl)amino)-2-oxo-1,2-dihydro-1,8-naphthyridine-3-carboxamide (9b)

According to general procedure B, the title compound was prepared in 79% yield from 1-(benzyloxy)-6-bromo-N-

(2,4-difluorobenzyl)-4-((2,4-dimethoxybenzyl)amino)-2-oxo-1,2-dihydro-1,8-naphthyridine-3-carboxamide (8a) and commercial available prop-2-yn-1-ylcyclohexane. ¹H NMR (500 MHz, CDCl₃) δ 12.02 (t, J=5.8 Hz, 1H), 10.70 (t, J=5.7 Hz, 1H), 8.66 (t, J=1.6 Hz, 1H), 8.32 (s, 1H), 7.68 (d, J=7.7 Hz, 2H), 7.40-7.36 (m, 4H), 7.25-7.24 (m, 1H), 6.85-6.78 (m, 2H), 6.48-6.45 (m, 2H), 5.25 (s, 2H), 4.75 (d, J=6.0 Hz, 2H), 4.60 (d, J=5.6 Hz, 2H), 3.82 (s, 3H), 3.80 (s, 3H), 2.32 (d, J=6.6 Hz, 2H), 1.85 (d, J=12.3 Hz, 2H), 1.78-1.68 (m, 3H), 1.57 (ddd, J=10.9, 7.0, 3.6 Hz, 1H), 1.31-1.16 (m, 3H), 1.05 (qd, J=12.4, 3.3 Hz, 2H).

1-(Benzyloxy)-N-(2,4-difluorobenzyl)-4-((2,4-dimethoxybenzyl)amino)-2-oxo-6-(4-phenylbut-1-yn-1-yl)-1,2-dihydro-1,8-naphthyridine-3-carboxamide (9c)

According to general procedure B, the title compound was prepared in 98% from 1-(benzyloxy)-6-bromo-N-(2,4-difluorobenzyl)-4-((2,4-dimethoxybenzyl)amino)-2-oxo-1,2-dihydro-1,8-naphthyridine-3-carboxamide (8a) and commercial available but-3-yn-1-ylbenzene. ¹H NMR (500 MHz, CDCl₃) δ 11.99 (t, J=5.6 Hz, 1H), 10.68 (t, J=5.7 Hz, 1H), 8.62 (s, 1H), 8.31 (s, 1H), 7.68-7.66 (m, 2H), 7.39-7.31 (m, 6H), 7.27-7.21 (m, 4H), 6.85-6.77 (m, 2H), 6.47-6.46 (m, 2H), 5.24 (s, 2H), 4.73 (d, J=5.8 Hz, 2H), 4.59 (d, J=5.7 Hz, 2H), 3.81 (s, 3H), 3.76 (s, 3H), 2.92 (d, J=7.4 Hz, 2H), 2.73 (t, J=7.4 Hz, 2H).

(E)-1-(Benzyloxy)-N-(2,4-difluorobenzyl)-4-((2,4-dimethoxybenzyl)amino)-2-oxo-6-styryl-1,2-dihydro-1,8-naphthyridine-3-carboxamide (9d)

According to general procedure C, the title compound was prepared in 27% yield from 1-(benzyloxy)-6-bromo-N-(2,4-difluorobenzyl)-4-((2,4-dimethoxybenzyl)amino)-2-oxo-1,2-dihydro-1,8-naphthyridine-3-carboxamide (8a) and commercial available styrene. ¹H NMR (500 MHz, CDCl₃) δ 12.14 (t, J=6.7 Hz, 1H), 10.81 (t, J=5.9 Hz, 1H), 8.71 (s, 1H), 8.44 (s, 1H), 7.71 (d, J=6.7 Hz, 2H), 7.44-7.38 (m, 10H), 6.99 (d, J=16.4 Hz, 1H), 6.88-6.81 (m, 2H), 6.58-6.52 (m, 3H), 5.29 (s, 2H), 4.80 (d, J=6.7 Hz, 2H), 4.65 (d, J=5.6 Hz, 2H), 3.86 (s, 3H), 3.77 (s, 3H). DUIS-MS m/z: 689 (M+H⁺).

1-(Benzyloxy)-N-(2,4-difluorobenzyl)-4-((2,4-dimethoxybenzyl)amino)-6-(3-hydroxyprop-1-yn-1-yl)-2-oxo-1,2-dihydro-1,8-naphthyridine-3-carboxamide (9e)

According to general procedure B, the title compound was prepared in 85% yield from 1-(benzyloxy)-6-bromo-N-(2,4-difluorobenzyl)-4-((2,4-dimethoxybenzyl)amino)-2-oxo-1,2-dihydro-1,8-naphthyridine-3-carboxamide (8a) and commercial available prop-2-yn-1-ol. ¹H NMR (500 MHz, CDCl₃) δ 12.02 (t, J=5.8 Hz, 1H), 10.65 (t, J=5.8 Hz, 1H), 8.64 (d, J=1.9 Hz, 1H), 8.33 (d, J=1.9 Hz, 1H), 7.66 (d, J=1.9 Hz, 1H), 7.65 (d, J=1.5 Hz, 1H), 7.40-7.33 (m, 4H), 7.20 (d, J=8.3 Hz, 1H), 6.85-6.78 (m, 2H), 6.46 (q, J=2.1 Hz, 2H), 5.24 (s, 2H), 4.71 (d, J=5.9 Hz, 2H), 4.59 (d, J=5.7 Hz, 2H), 4.46 (d, J=6.1 Hz, 2H), 3.80 (s, 3H), 3.78 (s, 3H).

1-(Benzyloxy)-N-(2,4-difluorobenzyl)-4-((2,4-dimethoxybenzyl)amino)-6-(8-hydroxyoct-1-yn-1-yl)-2-oxo-1,2-dihydro-1,8-naphthyridine-3-carboxamide (9f)

According to general procedure B, the title compound was prepared in 83% yield from 1-(benzyloxy)-6-bromo-N-(2,4-difluorobenzyl)-4-((2,4-dimethoxybenzyl)amino)-2-oxo-1,2-dihydro-1,8-naphthyridine-3-carboxamide (8a) and commercial available oct-7-yn-1-ol. ¹H NMR (500 MHz, CDCl₃) δ 12.00 (t, J=5.8 Hz, 1H), 10.69 (t, J=5.7 Hz, 1H), 8.65 (d, J=1.7 Hz, 1H), 8.33 (d, J=1.8 Hz, 1H), 7.67 (dd, J=7.4, 1.3 Hz, 2H), 7.40-7.33 (m, 4H), 7.23 (d, J=7.9 Hz, 3H), 6.85-6.781 (m, 2H), 6.48-6.46 (m, 2H), 5.24 (s, 2H), 4.75 (d, J=5.9 Hz, 2H), 4.59 (d, J=5.6 Hz, 2H), 3.81 (s, 3H), 3.79 (s, 3H), 3.66 (t, J=6.5 Hz, 2H), 2.43 (t, J=7.1 Hz, 2H), 1.66-1.57 (m, 4H), 1.50-1.41 (m, 4H). ESI-MS m/z: 711.3 (MH⁺).

1-(Benzyloxy)-N-(2,4-difluorobenzyl)-4-((2,4-dimethoxybenzyl)amino)-6-(6-hydroxyhex-1-yn-1-yl)-2-oxo-1,2-dihydro-1,8-naphthyridine-3-carboxamide (9g)

According to general procedure B, the title compound was prepared in 54% yield from 1-(benzyloxy)-6-bromo-N-(2,4-difluorobenzyl)-4-((2,4-dimethoxybenzyl)amino)-2-oxo-1,2-dihydro-1,8-naphthyridine-3-carboxamide hex-5-yn-1-ol. ¹H NMR (500 MHz, CDCl₃) δ 12.01 (t, J=5.9 Hz, 1H), 10.69 (t, J=5.7 Hz, 1H), 8.65 (dd, J=1.8, 0.9 Hz, 1H), 8.31-8.30 (m, 1H), 7.67 (d, J=6.8 Hz, 2H), 7.40-7.35 (m, 4H), 7.23 (s, 1H), 6.85-6.78 (m, 2H), 6.48 (d, J=7.8 Hz, 2H), 5.24 (s, 2H), 4.74 (d, J=6.0 Hz, 2H), 4.59 (d, J=5.7 Hz, 2H), 3.82 (d, J=0.9 Hz, 3H), 3.79 (d, J=0.8 Hz, 3H), 3.71 (dd, J=5.8, 5.3 Hz, 2H), 2.47 (t, J=6.2 Hz, 2H), 1.72-1.70 (m, 4H). ESI-MS m/z: 683.3 (M+H⁺).

6-(8-(Benzyloxy)-6-((2,4-difluorobenzyl)carbamoyl)-5-((2,4-dimethoxybenzyl)amino)-7-oxo-7,8-dihydro-1,8-naphthyridin-3-yl)hex-5-yn-1-yl benzoate (9h)

To the solution of 1-(benzyloxy)-N-(2,4-difluorobenzyl)-4-((2,4-dimethoxybenzyl)amino)-6-(6-hydroxyhex-1-yn-1-yl)-2-oxo-1,2-dihydro-1,8-naphthyridine-3-carboxamide (9g; 50 mg, 0.073 mmol) in pyridine (0.5 mL). benzoic anhydride (25 mg, 0.11 mmol) was added. The solution was stirred at rt for 2 hours. The reaction mixture was purified by CombiFlash. White solid 6-(8-(benzyloxy)-6-((2,4-difluorobenzyl)carbamoyl)-5-((2,4-dimethoxybenzyl)amino)-7-oxo-7,8-dihydro-1,8-naphthyridin-3-yl)hex-5-yn-1-yl benzoate (9h; 56 mg) was afforded in 96% yield. ¹H NMR (500 MHz, CDCl₃) δ 11.99 (t, J=5.8 Hz, 1H), 10.69 (t, J=5.8 Hz, 1H), 8.67 (d, J=1.4 Hz, 1H), 8.34 (d, J=1.7 Hz, 1H), 8.07-8.05 (m, 2H), 7.39-7.68 (m, 2H), 7.57 (t, J=7.4 Hz, 1H), 7.45 (t, J=7.8 Hz, 2H), 7.40-7.36 (m, 4H), 7.23 (d, J=8.9 Hz, 1H), 6.86-6.79 (m, 2H), 6.48-6.46 (m, 2H), 5.26 (s, 2H), 4.75 (d, J=5.9 Hz, 2H), 4.60 (d, J=5.6 Hz, 2H), 4.41 (t, J=6.4 Hz, 2H), 3.81 (s, 3H), 3.78 (s, 3H), 2.54 (t, J=7.0 Hz, 2H), 1.99-1.93 (m, 2H), 1.84-1.78 (m, 2H). ESI-MS m/z: 787.3 (M+H⁺).

1-(Benzyloxy)-N-(2,4-difluorobenzyl)-4-((2,4-dimethoxybenzyl)amino)-6-(3-(2-hydroxyethoxy)prop-1-yn-1-yl)-2-oxo-1,2-dihydro-1,8-naphthyridine-3-carboxamide (9i)

According to general procedure B, the title compound was prepared in 64% yield from 1-(benzyloxy)-6-bromo-N-(2,4-difluorobenzyl)-4-((2,4-dimethoxybenzyl)amino)-2-oxo-1,2-dihydro-1,8-naphthyridine-3-carboxamide (8a) and 2-(prop-2-yn-1-yloxy)ethanol. ¹H NMR (500 MHz, CDCl₃) δ 12.06 (t, J=5.9 Hz, 1H), 10.66 (t, J=5.7 Hz, 1H), 8.70 (d, J=1.2 Hz, 1H), 8.38 (d, J=1.4 Hz, 1H), 7.67 (d, J=6.6 Hz, 2H), 7.41-7.34 (m, 4H), 7.24 (d, J=7.9 Hz, 1H), 6.85-6.79 (m, 2H), 6.49-6.43 (m, 2H), 5.25 (s, 2H), 4.75 (d, J=6.0 Hz, 2H), 4.60 (d, J=5.7 Hz, 2H), 4.45 (s, 2H), 3.82 (s, 3H), 3.84-3.81 (m, 2H), 3.80 (s, 3H), 3.71-3.69 (m, 2H). DUIS-MS m/z: 685 (MH$^+$).

1-(benzyloxy)-N-(2,4-difluorobenzyl)-4-((2,4-dimethoxybenzyl)amino)-6-(5-hydroxypent-1-yn-1-yl)-2-oxo-1,2-dihydro-1,8-naphthyridine-3-carboxamide (9j)

According to general procedure B, the title compound was prepared in 52% yield from 1-(benzyloxy)-6-bromo-N-(2,4-difluorobenzyl)-4-((2,4-dimethoxybenzyl)amino)-2-oxo-1,2-dihydro-1,8-naphthyridine-3-carboxamide (8a) and commercial available pent-4-yn-1-ol. $^1$H NMR (500 MHz, CDCl$_3$) δ 12.02 (t, J=5.9 Hz, 1H), 10.69 (t, J=5.7 Hz, 1H), 8.65 (d, J=1.4 Hz, 1H), 8.30 (d, J=1.5 Hz, 1H), 7.67 (d, J=6.5 Hz, 2H), 7.40-7.36 (m, 4H), 7.26-7.25 (m, 1H), 6.82 (dt, J=11.9, 9.2 Hz, 2H), 6.49 (d, J=8.1 Hz, 2H), 5.25 (s, 2H), 4.74 (d, J=6.0 Hz, 2H), 4.60 (d, J=5.6 Hz, 2H), 3.83 (s, 3H), 3.80 (s, 3H), 3.78-3.73 (m, 2H), 2.56 (t, J=7.0 Hz, 2H), 1.86 (p, J=6.6 Hz, 2H). ESI-MS m/z: 669.2 (M+H$^+$).

(E)-Methyl 3-(8-(benzyloxy)-6-((2,4-difluorobenzyl)carbamoyl)-5-((2,4-dimethoxybenzyl)amino)-7-oxo-7,8-dihydro-1,8-naphthyridin-3-yl)acrylate (9k)

According to general procedure C, the title compound was prepared in 38% yield from 1-(benzyloxy)-6-bromo-N-(2,4-difluorobenzyl)-4-((2,4-dimethoxybenzyl)amino)-2-oxo-1,2-dihydro-1,8-naphthyridine-3-carboxamide (8a) and methyl acrylate. $^1$H NMR (500 MHz, CDCl$_3$) δ 12.35 (t, J=6.6 Hz, 1H), 10.73 (t, J=5.6 Hz, 1H), 8.72 (s, 1H), 8.40 (s, 1H), 7.69-7.66 (m, 2H), 7.59 (d, J=16.1 Hz, 1H), 7.42-7.38 (m, 4H), 7.23 (d, J=8.0 Hz, 1H), 6.88-6.82 (m, 2H), 6.57 (d, J=1.9 Hz, 1H), 6.54-6.50 (m, 1H), 6.34-6.32 (d, J=8.3 Hz, 1H), 6.02 (d, J=16.0 Hz, 1H), 5.27 (s, 2H), 4.78 (d, J=6.7 Hz, 2H), 4.64 (d, J=5.7 Hz, 2H), 3.85 (s, 3H), 3.85 (s, 3H), 3.83 (s, 3H). DUIS-MS m/z: 671 (MH$^+$).

1-(Benzyloxy)-N-(2,4-difluorobenzyl)-4-hydroxy-6-(5-hydroxypent-1-yn-1-yl)-2-oxo-1,2-dihydro-1,8-naphthyridine-3-carboxamide (9l)

According to general procedure B, the title compound was prepared in 54% yield from 1-(benzyloxy)-6-bromo-N-(2,4-difluorobenzyl)-4-hydroxy-2-oxo-1,2-dihydro-1,8-naphthyridine-3-carboxamide and pent-4-yn-1-ol (6). $^1$H NMR (500 MHz, CDCl$_3$) δ 10.31 (t, J=5.6 Hz, 1H), 8.46 (s, 1H), 7.66 (d, J=6.2 Hz, 2H), 7.42-7.35 (m, 5H), 6.90-6.83 (m, 3H), 5.27 (s, 2H), 4.67 (d, J=5.9 Hz, 2H), 3.85 (t, J=6.0 Hz, 2H), 2.61 (t, J=7.0 Hz, 2H), 1.93-1.90 (m, 2H). ESI-MS m/z: 520.2 (M+H$^+$).

Methyl 2-((1-(benzyloxy)-3-((2,4-difluorobenzyl)carbamoyl)-6-(5-hydroxypent-1-yn-1-yl)-2-oxo-1,2-dihydro-1,8-naphthyridin-4-yl)amino)acetate (9m)

According to general procedure B, the title compound was prepared in 45% yield from methyl 2-((1-(benzyloxy)-6-bromo-3-((2,4-difluorobenzyl)carbamoyl)-2-oxo-1,2-dihydro-1,8-naphthyridin-4-yl)amino)acetate (8b) and pent-4-yn-1-ol. $^1$H NMR (500 MHz, CDCl$_3$) δ 12.33 (s, 1H), 10.65 (t, J=5.7 Hz, 1H), 8.69 (s, 1H), 8.19 (s, 1H), 7.67-7.65 (m, 2H), 7.43-7.37 (m, 4H), 6.87-6.80 (m, 2H), 5.24 (s, 2H), 4.67 (d, J=5.6 Hz, 2H), 4.46 (d, J=4.9 Hz, 2H), 3.84 (s, 3H), 3.85-3.83 (m, 2H), 2.61 (t, J=7.0 Hz, 2H), 1.91 (t, J=6.5 Hz, 2H). ESI-MS m/z: 591.2 (M+H$^+$).

1-(Benzyloxy)-N-(2,4-difluorobenzyl)-4-((2-hydroxyethyl)amino)-6-(5-hydroxypent-1-yn-1-yl)-2-oxo-1,2-dihydro-1,8-naphthyridine-3-carboxamide (9n)

According to general procedure B, the title compound was prepared in 57% yield from 1-(benzyloxy)-6-bromo-N-(2,4-difluorobenzyl)-4-((2-hydroxyethyl)amino)-2-oxo-1,2-dihydro-1,8-naphthyridine-3-carboxamide (8c) and pent-4-yn-1-ol. $^1$H NMR (500 MHz, CDCl$_3$) δ 11.68 (s, 1H), 10.69 (t, J=5.5 Hz, 1H), 8.61 (d, J=1.8 Hz, 1H), 8.32 (d, J=1.8 Hz, 1H), 7.61-7.57 (m, 2H), 7.32-7.29 (m, 4H), 6.79-6.72 (m, 2H), 5.16 (s, 2H), 4.55 (d, J=5.5 Hz, 2H), 3.86-3.84 (m, 2H), 3.80-3.75 (m, 2H), 2.52 (t, J=7.0 Hz, 2H), 1.84-1.82 (m, 2H), 1.53-1.49 (m, 2H). ESI-MS: m/z 563.2 (MH$^+$)

(E)-Methyl 3-(8-(benzyloxy)-6-((2,4-difluorobenzyl)carbamoyl)-5-((2-hydroxyethyl)amino)-7-oxo-7,8-dihydro-1,8-naphthyridin-3-yl)acrylate (9o)

According to general procedure C, the title compound was prepared in 52% yield from 1-(benzyloxy)-6-bromo-N-(2,4-difluorobenzyl)-4-((2-hydroxyethyl)amino)-2-oxo-1,2-dihydro-1,8-naphthyridine-3-carboxamide (8c) and methyl acrylate. $^1$H NMR (500 MHz, CDCl$_3$) δ 11.82 (s, 1H), 10.71 (s, 1H), 8.84 (s, 1H), 8.67 (s, 1H), 7.74 (d, J=16.2 Hz, 1H), 7.58-7.55 (m, 2H), 7.41-7.38 (m, 4H), 6.87-6.81 (m, 2H), 6.55 (d, J=16.1 Hz, 1H), 5.26 (s, 2H), 4.64 (d, J=5.6 Hz, 2H), 3.85 (s, 3H), 3.60 (t, J=4.9 Hz, 2H), 2.62-2.60 (m, 2H). ESI-MS m/z: 565.2 (MH$^+$).

4-Amino-1-(benzyloxy)-6-bromo-N-(2,4-difluorobenzyl)-2-oxo-1,2-dihydro-1,8-naphthyridine-3-carboxamide (10a)

According to general procedure D, the title compound was prepared in 96% yield from 1-(benzyloxy)-6-bromo-N-(2,4-difluorobenzyl)-4-((2,4-dimethoxybenzyl)amino)-2-oxo-1,2-dihydro-1,8-naphthyridine-3-carboxamide (8a). $^1$H NMR (400 MHz, CDCl$_3$) δ 10.51 (t, J=5.8 Hz, 1H), 8.68 (d, J=2.1 Hz, 1H), 8.18 (d, J=2.1 Hz, 1H), 7.58 (dd, J=7.2, 2.3 Hz, 2H), 7.41-7.25 (m, 4H), 6.77 (ddd, J=12.6, 8.8, 4.1 Hz, 2H), 5.18 (s, 2H), 4.58 (d, J=5.8 Hz, 2H). ESI-MS m/z: 515.0, 517.0 (M+H$^+$).

4-Amino-1-(benzyloxy)-N-(2,4-difluorobenzyl)-2-oxo-6-phenyl-1,2-dihydro-1,8-naphthyridine-3-carboxamide (10b)

According to general procedure D, the title compound was prepared in 73% yield from 1-(benzyloxy)-N-(2,4-difluorobenzyl)-4-((2,4-dimethoxybenzyl)amino)-2-oxo-6-phenyl-1,2-dihydro-1,8-naphthyridine-3-carboxamide (9a). $^1$H NMR (500 MHz, CDCl$_3$) δ 10.65 (t, J=5.8 Hz, 1H), 8.96 (d, J=1.5 Hz, 1H), 8.22 (d, J=1.5 Hz, 1H), 7.69-7.67 (m, 2H), 7.61-7.59 (m, 2H), 7.48 (t, J=7.7 Hz, 2H), 7.43-7.35 (m, 4H), 6.85-6.78 (m, 2H), 5.29 (s, 3H), 4.62 (d, J=5.8 Hz, 3H). ESI-MS m/z: 513.1 (M+H$^+$).

4-Amino-1-(benzyloxy)-6-(3-cyclohexylprop-1-yn-1-yl)-N-(2,4-difluorobenzyl)-2-oxo-1,2-dihydro-1,8-naphthyridine-3-carboxamide (10c)

According to general procedure D, the title compound was prepared in 91% yield from 1-(benzyloxy)-6-(3-cyclohexylprop-1-yn-1-yl)-N-(2,4-difluorobenzyl)-4-((2,4-dimethoxybenzyl)amino)-2-oxo-1,2-dihydro-1,8-naphthyridine-3-carboxamide (9b). $^1$H NMR (500 MHz, CDCl$_3$) δ 10.60 (t, J=5.8 Hz, 1H), 8.74 (d, J=1.8 Hz, 1H), 8.03 (d, J=1.9 Hz, 1H), 7.66 (dd, J=7.5, 1.8 Hz, 2H), 7.42-7.35 (m, 4H), 6.87-6.80 (m, 2H), 5.25 (s, 2H), 4.63 (d, J=5.8 Hz, 2H), 2.34 (d, J=6.7 Hz, 2H), 1.88 (dd, J=13.5, 1.9 Hz, 2H), 1.78-1.74 (m, 2H), 1.70 (ddd, J=12.6, 5.0, 2.6 Hz, 1H), 1.62-1.55 (m, 1H), 1.34-1.25 (m, 2H), 1.22-1.16 (m, 1H), 1.07 (ddd, J=24.4, 12.4, 3.3 Hz, 2H). ESI-MS m/z: 557.2 (M+H$^+$).

4-Amino-1-(benzyloxy)-N-(2,4-difluorobenzyl)-2-oxo-6-(4-phenylbut-1-yn-1-yl)-1,2-dihydro-1,8-naphthyridine-3-carboxamide (10d)

According to general procedure D, the title compound was prepared in 94% yield from. 1-(benzyloxy)-N-(2,4-difluorobenzyl)-4-((2,4-dimethoxybenzyl)amino)-2-oxo-6-(4-phenylbut-1-yn-1-yl)-1,2-dihydro-1,8-naphthyridine-3-carboxamide (9c). $^1$H NMR (500 MHz, CDCl$_3$) δ 10.61 (t, J=5.8 Hz, 1H), 8.69 (s, 1H), 8.00 (s, 1H), 7.65 (dd, J=7.1, 1.7 Hz, 2H), 7.39-7.32 (m, 6H), 7.28-7.26 (m, 3H), 6.87-6.80 (m, 2H), 5.24 (s, 2H), 4.63 (d, J=5.8 Hz, 2H), 2.94 (t, J=7.4 Hz, 2H), 2.74 (t, J=7.5 Hz, 2H). ESI-MS m/z: 565.2 (M+H$^+$).

(E)-4-Amino-1-(benzyloxy)-N-(2,4-difluorobenzyl)-2-oxo-6-styryl-1,2-dihydro-1,8-naphthyridine-3-carboxamide (10e)

According to general procedure D, the title compound was prepared in 68% yield from (E)-1-(benzyloxy)-N-(2,4-difluorobenzyl)-4-((2,4-dimethoxybenzyl)amino)-2-oxo-6-styryl-1,2-dihydro-1,8-naphthyridine-3-carboxamide (9d). $^1$H NMR (500 MHz, CDCl$_3$) δ 10.65 (t, J=5.4 Hz, 1H), 8.89 (s, 1H), 8.12 (s, 1H), 7.81 (d, J=8.3 Hz, 1H), 7.68 (d, J=7.1 Hz, 2H), 7.63 (d, J=7.0 Hz, 1H), 7.53 (d, J=8.1 Hz, 2H), 7.40-7.38 (m, 4H), 7.33-7.30 (m, 1H), 7.17 (dd, J=47.6, 17.5 Hz, 2H), 6.89-6.79 (m, 2H), 5.28 (s, 2H), 4.64 (d, J=5.2 Hz, 2H). ESI-MS m/z: 539.2 (M+H$^+$).

4-Amino-1-(benzyloxy)-N-(2,4-difluorobenzyl)-6-(3-hydroxyprop-1-yn-1-yl)-2-oxo-1,2-dihydro-1,8-naphthyridine-3-carboxamide (10f)

According to general procedure D, the title compound was prepared in 56% yield from 1-(benzyloxy)-N-(2,4-difluorobenzyl)-4-((2,4-dimethoxybenzyl)amino)-6-(3-hydroxyprop-1-yn-1-yl)-2-oxo-1,2-dihydro-1,8-naphthyridine-3-carboxamide (9e). $^1$H NMR (500 MHz, CDCl$_3$) δ 10.55 (s, 1H), 8.75 (s, 1H), 8.06 (s, 1H), 7.67-7.65 (m, 2H), 7.41-7.37 (m, 4H), 6.84 (dd, J=19.5, 9.2 Hz, 2H), 5.26 (s, 2H), 4.64 (d, J=5.6 Hz, 2H), 4.53 (s, 2H). ESI-MS m/z: 491.1 (MH$^+$).

3-(5-Amino-8-(benzyloxy)-6-((2,4-difluorobenzyl)carbamoyl)-7-oxo-7,8-dihydro-1,8-naphthyridin-3-yl)prop-2-yn-1-yl acetate (10g)

Compound 4-amino-1-(benzyloxy)-N-(2,4-difluorobenzyl)-6-(3-hydroxyprop-1-yn-1-yl)-2-oxo-1,2-dihydro-1,8-naphthyridine-3-carboxamide (10f; 29 mg, 0.059 mmol) mixed with acetic anhydride (8.38 μl, 0.089 mmol) in pyridine (0.5 mL). The solution was stirred at rt for 2 hours. The resultant mixture was purified by CombiFlash. 3-(5-amino-8-(benzyloxy)-6-((2,4-difluorobenzyl)carbamoyl)-7-oxo-7,8-dihydro-1,8-naphthyridin-3-yl)prop-2-yn-1-yl acetate (10g; 24 mg) was afforded in 76% yield. $^1$H NMR (500 MHz, CDCl$_3$) δ 10.54 (t, J=5.7 Hz, 1H), 8.77 (d, J=1.7 Hz, 1H), 8.16 (d, J=1.7 Hz, 1H), 7.65 (dd, J=7.5, 1.6 Hz, 2H), 7.42-7.33 (m, 4H), 6.87-6.80 (m, 2H), 5.25 (s, 2H), 4.93 (s, 2H), 4.63 (d, J=5.7 Hz, 2H), 2.16 (s, 3H). ESI-MS m/z: 533.2 (MH$^+$).

4-Amino-1-(benzyloxy)-N-(2,4-difluorobenzyl)-6-(3-(dimethylamino)prop-1-yn-1-yl)-2-oxo-1,2-dihydro-1,8-naphthyridine-3-carboxamide (10h)

According to general procedure B and D, the title compound was prepared in 33% yield (two steps) from 1-(benzyloxy)-6-bromo-N-(2,4-difluorobenzyl)-4-((2,4-dimethoxybenzyl)amino)-2-oxo-1,2-dihydro-1,8-naphthyridine-3-carboxamide (8a) and N,N-dimethylprop-2-yn-1-amine. $^1$H NMR (500 MHz, CDCl$_3$) δ 10.57 (t, J=5.7 Hz, 1H), 8.77 (d, J=1.6 Hz, 1H), 8.11 (d, J=1.6 Hz, 1H), 7.67-7.65 (m, 2H), 7.42-7.36 (m, 4H), 6.87-6.80 (m, 2H), 5.25 (s, 2H), 4.63 (d, J=5.7 Hz, 2H), 3.51 (s, 2H), 2.42 (s, 6H). ESI-MS m/z: 518.2 (MH$^+$).

4-Amino-1-(benzyloxy)-N-(2,4-difluorobenzyl)-6-(8-hydroxyoct-1-yn-1-yl)-2-oxo-1,2-dihydro-1,8-naphthyridine-3-carboxamide (10i)

According to general procedure D, the title compound was prepared in 61% yield from 1-(benzyloxy)-N-(2,4-difluorobenzyl)-4-((2,4-dimethoxybenzyl)amino)-6-(8-hydroxyoct-1-yn-1-yl)-2-oxo-1,2-dihydro-1,8-naphthyridine-3-carboxamide (9f). $^1$H NMR (400 MHz, CDCl$_3$) δ 10.55 (t, J=5.7 Hz, 1H), 8.65 (s, 1H), 8.11 (s, 1H), 7.61-7.59 (m, 2H), 7.37-7.29 (m, 4H), 6.82-6.74 (m, 2H), 5.19 (s, 2H), 4.58 (d, J=5.6 Hz, 2H), 3.63 (bs, 2H), 2.38 (t, J=6.9 Hz, 4H), 1.59-1.54 (m, 4H), 1.47-1.40 (m, 4H). ESI-MS m/z: 561.2 (MH$^+$).

4-Amino-1-(benzyloxy)-N-(2,4-difluorobenzyl)-6-(6-hydroxyhex-1-yn-1-yl)-2-oxo-1,2-dihydro-1,8-naphthyridine-3-carboxamide (10j)

According to general procedure D, the title compound was prepared in 94% yield from 1-(benzyloxy)-N-(2,4-difluorobenzyl)-4-((2,4-dimethoxybenzyl)amino)-6-(6-hydroxyhex-1-yn-1-yl)-2-oxo-1,2-dihydro-1,8-naphthyridine-3-carboxamide (9g). $^1$H NMR (500 MHz, CDCl$_3$) δ 10.59 (s, 1H), 8.75 (bs, 1H), 8.01 (s, 1H), 7.67 (d, J=6.7 Hz, 2H), 7.42-7.35 (m, 4H), 6.87-6.81 (m, 2H), 5.26 (s, 2H), 4.64 (d, J=5.6 Hz, 2H), 3.78 (d, J=13.5 Hz, 2H), 2.52 (t, J=6.5 Hz, 2H), 1.76-1.74 (m, 2H), 1.66-1.60 (m, 2H). ESI-MS m/z: 533.2 (M+H$^+$).

4-Amino-1-(benzyloxy)-N-(2,4-difluorobenzyl)-6-(3-(2-hydroxyethoxy)prop-1-yn-1-yl)-2-oxo-1,2-dihydro-1,8-naphthyridine-3-carboxamide (10k)

According to general procedure D, the title compound was prepared in 87% yield from 1-(benzyloxy)-N-(2,4-difluorobenzyl)-4-((2,4-dimethoxybenzyl)amino)-6-(3-(2-hydroxyethoxy)prop-1-yn-1-yl)-2-oxo-1,2-dihydro-1,8-naphthyridine-3-carboxamide (9i). $^1$H NMR (500 MHz, CDCl$_3$) δ 10.55 (t, J=5.7 Hz, 1H), 8.79 (d, J=1.7 Hz, 1H), 8.08 (d, J=1.8 Hz, 1H), 7.68-7.67 (m, 2H), 7.41-7.38 (m, 4H), 6.88-6.82 (m, 2H), 5.27 (s, 2H), 4.64 (d, J=5.8 Hz, 2H), 4.49 (s, 2H), 3.86-3.84 (m, 2H), 3.77-3.75 (m, 2H). ESI-MS m/z: 535.2 (MH$^+$).

4-Amino-1-(benzyloxy)-N-(2,4-difluorobenzyl)-6-(5-hydroxypent-1-yn-1-yl)-2-oxo-1,2-dihydro-1,8-naphthyridine-3-carboxamide (10l)

According to general procedure D, the title compound was prepared in 65% yield from 1-(benzyloxy)-N-(2,4-difluorobenzyl)-4-((2,4-dimethoxybenzyl)amino)-6-(5-hydroxypent-1-yn-1-yl)-2-oxo-1,2-dihydro-1,8-naphthyridine-3-carboxamide (9j). $^1$H NMR (400 MHz, CDCl$_3$) δ 10.53 (t, J=5.8 Hz, 1H), 8.68 (d, J=1.7 Hz, 1H), 7.98 (d, J=1.8 Hz, 1H), 7.62 (dd, J=7.3, 1.9 Hz, 2H), 7.38-7.328 (m, 4H), 6.78 (dt, J=9.0, 5.3 Hz, 2H), 5.21 (s, 2H), 4.59 (d, J=5.7 Hz, 2H), 3.79 (t, J=6.1 Hz, 2H), 2.55 (t, J=7.0 Hz, 2H), 1.85 (p, J=6.6 Hz, 2H). ESI-MS m/z: 519.2 (M+H$^+$).

(E)-Methyl 3-(5-amino-8-(benzyloxy)-6-((2,4-difluorobenzyl)carbamoyl)-7-oxo-7,8-dihydro-1,8-naphthyridin-3-yl)acrylate (10m)

According to general procedure D, the title compound was prepared in 38% yield from (E)-methyl 3-(8-(benzyloxy)-6-((2,4-difluorobenzyl)carbamoyl)-5-((2,4-dimethoxybenzyl)amino)-7-oxo-7,8-dihydro-1,8-naphthyridin-3-yl)acrylate (9k). $^1$H NMR (500 MHz, CDCl$_3$) δ 10.54 (d, J=5.6 Hz, 1H), 8.89 (d, J=1.5 Hz, 1H), 8.13 (s, 1H), 7.76 (d, J=16.1 Hz, 1H), 7.67 (d, J=6.1 Hz, 2H), 7.41-7.37 (m, 4H), 6.87-6.81 (m, 2H), 6.59 (d, J=16.1 Hz, 1H), 5.27 (s, 2H), 4.64 (d, J=5.7 Hz, 2H), 3.86 (s, 3H). ESI-MS m/z: 521.2 (MH$^+$).

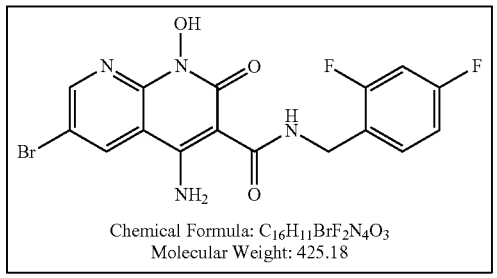 [SMILES: Nc1c(C(=O)NCc2ccc(F)cc2F)c(=O)n(O)c2ncc(Br)cc12]

Chemical Formula: C$_{16}$H$_{11}$BrF$_2$N$_4$O$_3$
Molecular Weight: 425.18

4-Amino-6-bromo-N-(2,4-difluorobenzyl)-1-hydroxy-2-oxo-1,2-dihydro-1,8-naphthyridine-3-carboxamide (XZ418)

According to general procedure E, the title compound was prepared in 25% yield from 4-amino-1-(benzyloxy)-6-bromo-N-(2,4-difluorobenzyl)-2-oxo-1,2-dihydro-1,8-naphthyridine-3-carboxamide (10a) after purification by preparative HPLC (with a linear gradient of 30% B to 70% B over 30 minutes; retention time=22.7 minutes). $^1$H NMR (500 MHz, DMSO-d$_6$) δ 10.71 (s, 1H), 10.58 (t, J=6.0 Hz, 1H), 8.97 (d, J=2.2 Hz, 1H), 8.81 (d, J=2.2 Hz, 1H), 7.42 (dd, J=15.5, 8.7 Hz, 1H), 7.24 (ddd, J=10.6, 9.4, 2.6 Hz, 1H), 7.07 (td, J=8.6, 2.6 Hz, 1H), 4.52 (d, J=5.8 Hz, 2H). ESI-MS m/z: 425.0 (MH$^+$). HRMS calcd C$_{16}$H$_{12}$BrF$_2$N$_4$O$_3$ [MH$^+$], 425.0055; found, 425.0039.

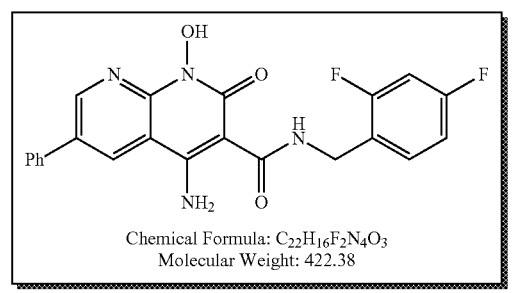

Chemical Formula: C$_{22}$H$_{16}$F$_2$N$_4$O$_3$
Molecular Weight: 422.38

4-Amino-N-(2,4-difluorobenzyl)-1-hydroxy-2-oxo-6-phenyl-1,2-dihydro-1,8-naphthyridine-3-carboxamide (XZ420)

According to general procedure E, the title compound was prepared in 59% yield from 4-amino-1-(benzyloxy)-N-(2,4-difluorobenzyl)-2-oxo-6-phenyl-1,2-dihydro-1,8-naphthyridine-3-carboxamide (10b) after purification by preparative HPLC (with a linear gradient of 30% B to 70% B over 30 minutes; retention time=27.3 minutes). $^1$H NMR (500 MHz, DMSO-d$_6$) δ 10.67 (t, J=5.8 Hz, 1H), 9.08 (d, J=2.1 Hz, 1H), 9.01 (d, J=2.1 Hz, 1H), 7.87 (dd, J=8.2, 1.0 Hz, 2H), 7.55 (t, J=7.7 Hz, 2H), 7.46-7.41 (m, 2H), 7.27-7.22 (m, 1H), 7.08 (td, J=8.6, 2.5 Hz, 1H), 4.54 (d, J=5.8 Hz, 2H). ESI-MS m/z: 423.1 (MH$^+$). HRMS calcd C$_{22}$H$_{17}$F$_2$N$_4$O$_3$[MH$^+$], 423.1263; found, 423.1243.

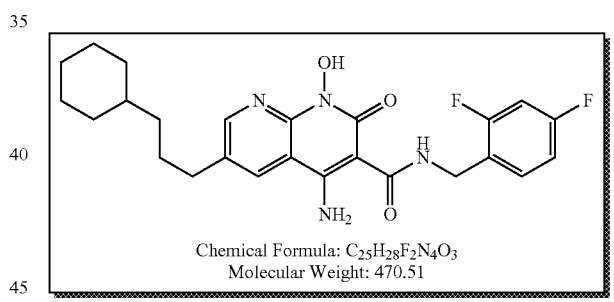

Chemical Formula: C$_{25}$H$_{28}$F$_2$N$_4$O$_3$
Molecular Weight: 470.51

4-Amino-6-(3-cyclohexylpropyl)-N-(2,4-difluorobenzyl)-1-hydroxy-2-oxo-1,2-dihydro-1,8-naphthyridine-3-carboxamide (XZ428)

According to general procedure E, the title compound was prepared in 40% yield from 4-amino-1-(benzyloxy)-6-(3-cyclohexylprop-1-yn-1-yl)-N-(2,4-difluorobenzyl)-2-oxo-1,2-dihydro-1,8-naphthyridine-3-carboxamide (10c) after purification by preparative HPLC (with a linear gradient of 50% B to 80% B over 30 minutes; retention time=27.5 minutes). $^1$H NMR (500 MHz, DMSO-d$_6$) δ 10.63 (t, J=5.8 Hz, 1H), 8.51 (s, 1H), 8.47 (s, 1H), 7.36 (dd, J=15.5, 8.6 Hz, 1H), 7.20-7.15 (m, 1H), 7.00 (t, J=8.5 Hz, 1H), 4.45 (d, J=5.7 Hz, 2H), 2.59 (t, J=7.7 Hz, 2H), 1.63-1.52 (m, 7H), 1.16-1.00 (m, 6H), 0.82-0.75 (m, 2H). ESI-MS m/z: 471.2 (MH$^+$). HRMS calcd C$_{25}$H$_{29}$F$_2$N$_4$O$_3$[MH$^+$], 471.2202; found, 471.2204.

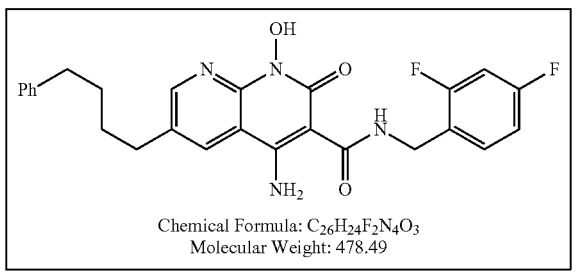 [SMILES: Nc1c(C(=O)NCc2ccc(F)cc2F)c(=O)n(O)c2ncc(CCCCc3ccccc3)cc12]

4-Amino-N-(2,4-difluorobenzyl)-1-hydroxy-2-oxo-6-(4-phenylbutyl)-1,2-dihydro-1,8-naphthyridine-3-carboxamide (XZ429)

According to general procedure E, the title compound was prepared in 27% yield from 4-amino-1-(benzyloxy)-N-(2,4-difluorobenzyl)-2-oxo-6-(4-phenylbut-1-yn-1-yl)-1,2-dihydro-1,8-naphthyridine-3-carboxamide (10d) after purification by preparative HPLC (with a linear gradient of 40% B to 80% B over 30 minutes; retention time=26.0 minutes). $^1$H NMR (500 MHz, DMSO-$d_6$) δ 10.69 (t, J=5.8 Hz, 1H), 8.58 (s, 1H), 8.54 (s, 1H), 7.42 (dd, J=15.5, 8.5 Hz, 1H), 7.26 (t, J=7.6 Hz, 2H), 7.24-7.21 (m, 1H), 7.19-7.14 (m, 3H), 7.07 (t, J=8.5 Hz, 1H), 4.51 (d, J=5.7 Hz, 2H), 2.72 (t, J=7.3 Hz, 2H), 2.62 (t, J=7.5 Hz, 2H), 1.69 (dd, J=14.8, 7.1 Hz, 2H), 1.65-1.53 (m, 2H). ESI-MS m/z: 479.2 (MH$^+$). HRMS calcd $C_{26}H_{25}F_2N_4O_3$[MH$^+$], 479.1889; found, 479.1880.

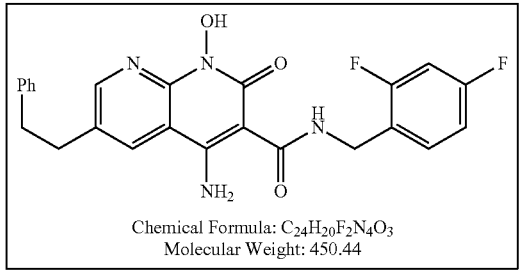 [SMILES: Nc1c(C(=O)NCc2ccc(F)cc2F)c(=O)n(O)c2ncc(CCc3ccccc3)cc12]

4-Amino-N-(2,4-difluorobenzyl)-1-hydroxy-2-oxo-6-phenethyl-1,2-dihydro-1,8-naphthyridine-3-carboxamide (XZ430)

According to general procedure E, the title compound was prepared in 85% yield from (E)-4-amino-1-(benzyloxy)-N-(2,4-difluorobenzyl)-2-oxo-6-styryl-1,2-dihydro-1,8-naphthyridine-3-carboxamide (10e) after purification by preparative HPLC (with a linear gradient of 40% B to 80% B over 30 minutes; retention time=22.5 minutes). $^1$H NMR (500 MHz, DMSO-$d_6$) δ 10.69 (bs, 1H), 10.51 (bs, 1H), 8.61 (s, 1H), 8.53 (s, 1H), 7.45-7.42 (m, 1H), 7.35-7.32 (m, 1H), 7.27 (d, J=7.0 Hz, 1H), 7.23 (d, J=6.7 Hz, 2H), 7.20-7.17 (m, 1H), 7.08-7.05 (m, 1H), 4.52 (d, J=5.5 Hz, 2H), 2.99 (bs, 4H). ESI-MS m/z: 451.1 (MH$^+$). HRMS calcd $C_{24}H_{21}F_2N_4O_3$[MH$^+$], 451.1576; found, 451.1576.

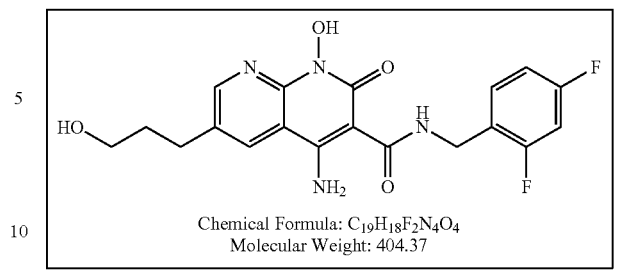

4-Amino-N-(2,4-difluorobenzyl)-1-hydroxy-6-(3-hydroxypropyl)-2-oxo-1,2-dihydro-1,8-naphthyridine-3-carboxamide (XZ423)

According to general procedure E, the title compound was prepared in 76% yield from 4-amino-1-(benzyloxy)-N-(2,4-difluorobenzyl)-6-(3-hydroxyprop-1-yn-1-yl)-2-oxo-1,2-dihydro-1,8-naphthyridine-3-carboxamide (10f) after purification by preparative HPLC (with a linear gradient of 30% B to 70% B over 30 minutes; retention time=15.2 minutes). $^1$H NMR (500 MHz, DMSO-$d_6$) δ 10.70 (t, J=5.7 Hz, 1H), 10.52 (bs, 1H), 8.58 (s, 1H), 8.55 (s, 1H), 7.42 (dd, J=15.5, 8.1 Hz, 1H), 7.24 (t, J=9.9 Hz, 1H), 7.07 (t, J=8.5 Hz, 1H), 4.52 (d, J=5.7 Hz, 2H), 3.46-3.43 (m, 2H), 2.73 (t, J=7.7 Hz, 2H), 1.83-1.77 (m, 2H). ESI-MS m/z: 405.1 (MH$^+$). HRMS calcd $C_{19}H_{19}F_2N_4O_4$[MH$^+$], 405.1369; found, 405.1362.

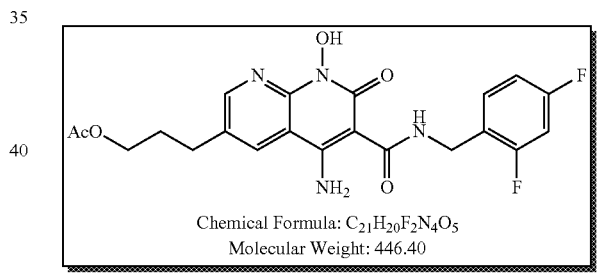

3-(5-Amino-6-((2,4-difluorobenzyl)carbamoyl)-8-hydroxy-7-oxo-7,8-dihydro-1,8-naphthyridin-3-yl)propyl acetate (XZ424)

According to general procedure E, the title compound was prepared in 71% yield from 3-(5-amino-8-(benzyloxy)-6-((2,4-difluorobenzyl)carbamoyl)-7-oxo-7,8-dihydro-1,8-naphthyridin-3-yl)prop-2-yn-1-yl acetate (10g) after purification by preparative HPLC (with a linear gradient of 30% B to 70% B over 30 minutes; retention time=20.6 minutes). $^1$H NMR (500 MHz, DMSO-$d_6$) δ 10.69 (t, J=5.7 Hz, 1H), 8.60 (s, 1H), 8.57 (s, 1H), 7.42 (dd, J=15.6, 7.5 Hz, 1H), 7.24 (t, J=9.9 Hz, 1H), 7.07 (t, J=8.5 Hz, 1H), 4.52 (d, J=5.5 Hz, 2H), 4.05 (t, J=6.3 Hz, 2H), 2.75 (t, J=7.9 Hz, 2H), 2.00 (s, 3H), 1.97 (d, J=7.7 Hz, 2H). ESI-MS m/z: 447.1 (MH$^+$). HRMS calcd $C_{21}H_{21}F_2N_4O_5$[MH$^+$], 447.1475; found, 447.1477.

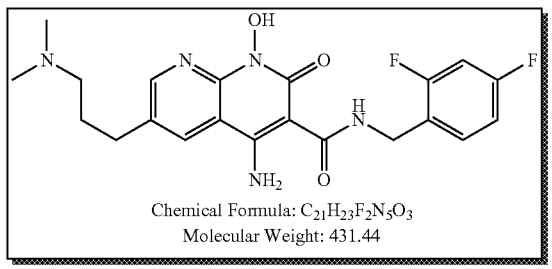

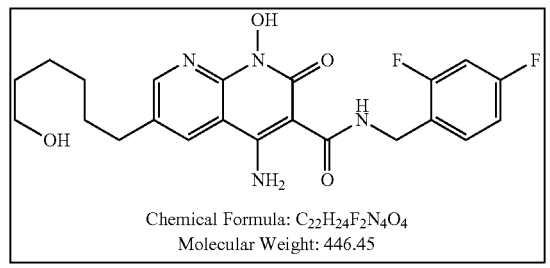

4-Amino-N-(2,4-difluorobenzyl)-6-(3-(dimethylamino)propyl)-1-hydroxy-2-oxo-1,2-dihydro-1,8-naphthyridine-3-carboxamide (XZ425)

According to general procedure E, the title compound was prepared in 52% yield from 4-amino-1-(benzyloxy)-N-(2,4-difluorobenzyl)-6-(3-(dimethylamino)prop-1-yn-1-yl)-2-oxo-1,2-dihydro-1,8-naphthyridine-3-carboxamide (10h) after purification by preparative HPLC (with a linear gradient of 30% B to 55% B over 30 minutes; retention time=17.2 minutes). $^1$H NMR (500 MHz, DMSO-$d_6$) δ 10.68 (t, J=5.8 Hz, 1H), 10.57 (s, 1H), 8.62 (s, 1H), 8.57 (s, 1H), 7.42 (dd, J=15.5, 8.5 Hz, 1H), 7.27-7.22 (m, 1H), 7.07 (dd, J=9.8, 7.3 Hz, 1H), 4.52 (d, J=5.8 Hz, 2H), 3.06 (d, J=7.7 Hz, 2H), 2.78 (s, 6H), 2.74 (t, J=7.5 Hz, 2H), 2.01 (dt, J=15.7, 7.8 Hz, 2H). ESI-MS m/z: 432.2 (MH$^+$). HRMS calcd $C_{21}H_{24}F_2N_5O_3$ [MH$^+$], 432.1842; found, 432.1824.

4-Amino-N-(2,4-difluorobenzyl)-1-hydroxy-6-(6-hydroxyhexyl)-2-oxo-1,2-dihydro-1,8-naphthyridine-3-carboxamide (XZ426)

According to general procedure E, the title compound was prepared in 65% yield from 4-amino-1-(benzyloxy)-N-(2,4-difluorobenzyl)-6-(6-hydroxyhex-1-yn-1-yl)-2-oxo-1,2-dihydro-1,8-naphthyridine-3-carboxamide (10j) after purification by preparative HPLC (with a linear gradient of 30% B to 60% B over 30 minutes; retention time=23.2 minutes). $^1$H NMR (500 MHz, DMSO-$d_6$) δ 10.70 (t, J=5.5 Hz, 1H), 10.53 (bs, 1H), 8.58 (s, 1H), 8.55 (s, 1H), 7.43 (dd, J=15.3, 8.0 Hz, 1H), 7.25 (t, J=9.9 Hz, 1H), 7.07 (t, J=8.3 Hz, 1H), 4.52 (d, J=5.1 Hz, 2H), 3.38 (t, J=6.3 Hz, 2H), 2.68 (t, J=7.5 Hz, 2H), 1.65 (s, 2H), 1.41 (d, J=6.4 Hz, 2H), 1.33 (s, 4H). ESI-MS m/z: 447.2 (M+H$^+$). HRMS calcd $C_{22}H_{25}F_2N_4O_4$ [MH$^+$], 447.1838; found, 447.1838.

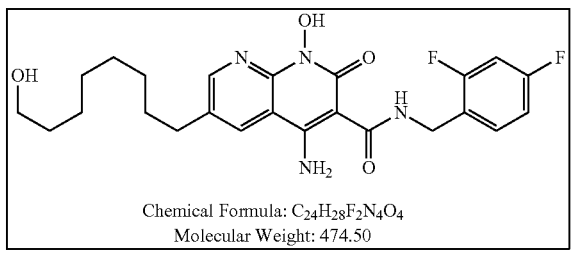 [SMILES: Nc1c(C(=O)NCc2ccc(F)cc2F)c(=O)n(O)c2ncc(CCCCCCCCO)cc12]

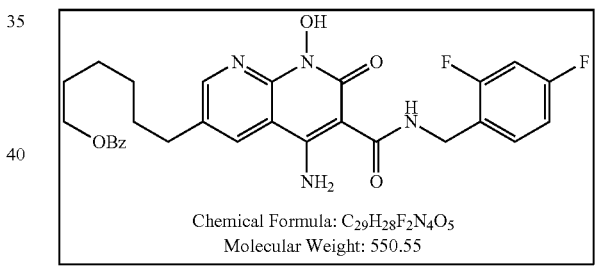

4-Amino-N-(2,4-difluorobenzyl)-1-hydroxy-6-(8-hydroxyoctyl)-2-oxo-1,2-dihydro-1,8-naphthyridine-3-carboxamide (XZ433)

According to general procedure E, the title compound was prepared in 88% yield from 4-amino-1-(benzyloxy)-N-(2,4-difluorobenzyl)-6-(8-hydroxyoct-1-yn-1-yl)-2-oxo-1,2-dihydro-1,8-naphthyridine-3-carboxamide (10i) after purification by preparative HPLC (with a linear gradient of 35% B to 60% B over 30 minutes; retention time=25.8 minutes). $^1$H NMR (500 MHz, DMSO-$d_6$) δ 10.63 (t, J=5.7 Hz, 1H), 8.51 (s, 1H), 8.47 (s, 1H), 7.36 (dd, J=15.5, 8.4 Hz, 1H), 7.17 (dd, J=14.2, 5.7 Hz, 1H), 7.00 (t, J=7.5 Hz, 1H), 4.45 (d, J=5.7 Hz, 2H), 3.29 (d, J=6.6 Hz, 2H), 2.61 (t, J=7.6 Hz, 2H), 1.58 (bs, 2H), 1.32 (d, J=6.5 Hz, 2H), 1.24 (bs, 4H), 1.19 (bs, 4H). ESI-MS m/z: 475.2 (MH$^+$). HRMS calcd $C_{24}H_{29}F_2N_4O_4$ [MH$^+$], 475.2151; found, 475.2151.

6-(5-Amino-6-((2,4-difluorobenzyl)carbamoyl)-8-hydroxy-7-oxo-7,8-dihydro-1,8-naphthyridin-3-yl)hexyl benzoate (XZ427)

According to general procedure E, the title compound was prepared in 45% yield from 6-(8-(benzyloxy)-6-((2,4-difluorobenzyl)carbamoyl)-5-((2,4-dimethoxybenzyl)amino)-7-oxo-7,8-dihydro-1,8-naphthyridin-3-yl)hex-5-yn-1-yl benzoate (9h) after purification by preparative HPLC (with a linear gradient of 55% B to 75% B over 30 minutes; retention time=25.4 minutes). $^1$H NMR (500 MHz, DMSO-$d_6$) δ 10.69 (t, J=5.7 Hz, 1H), 8.58 (d, J=1.9 Hz, 1H), 8.54 (s, 1H), 7.94 (dd, J=8.4, 1.3 Hz, 2H), 7.64 (dt, J=8.7, 1.3 Hz, 1H), 7.53-7.50 (m, 2H), 7.42 (dd, J=15.3, 8.5 Hz, 1H), 7.26-7.21 (m, 1H), 7.06 (dd, J=9.8, 7.3 Hz, 1H), 4.51 (d, J=5.6 Hz, 2H), 4.26 (t, J=6.5 Hz, 2H), 2.70-2.67 (m, 2H), 1.73-1.66 (m, 4H), 1.45-1.42 (m, 2H), 1.39-1.38 (m, 2H). ESI-MS m/z: 551.2 (MH$^+$). HRMS calcd $C_{29}H_{29}F_2N_4O_5$ [MH$^+$], 551.2089; found, 551.2089.

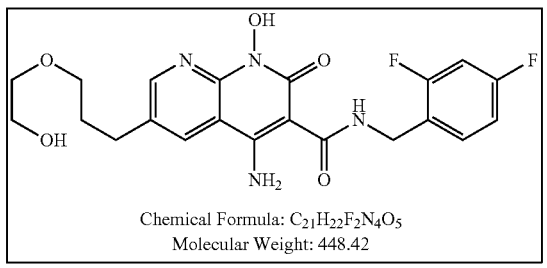 [SMILES: Nc1c(C(=O)NCc2ccc(F)cc2F)c(=O)n(O)c2ncc(CCCOCCO)cc12]

Chemical Formula: $C_{21}H_{22}F_2N_4O_5$
Molecular Weight: 448.42

4-Amino-N-(2,4-difluorobenzyl)-1-hydroxy-6-(3-(2-hydroxyethoxy)propyl)-2-oxo-1,2-dihydro-1,8-naphthyridine-3-carboxamide (XZ432)

According to general procedure E, the title compound was prepared in 86% yield from 4-amino-1-(benzyloxy)-N-(2,4-difluorobenzyl)-6-(3-(2-hydroxyethoxy)prop-1-yn-1-yl)-2-oxo-1,2-dihydro-1,8-naphthyridine-3-carboxamide (10k) after purification by preparative HPLC (with a linear gradient of 30% B to 60% B over 30 minutes; retention time=20.5 minutes). $^1$H NMR (500 MHz, DMSO-$d_6$) δ 10.69 (t, J=5.8 Hz, 1H), 8.59 (d, J=1.9 Hz, 1H), 8.56 (d, J=1.9 Hz, 1H), 7.52-7.35 (m, 1H), 7.24 (ddd, J=10.5, 9.4, 2.6 Hz, 1H), 7.07 (ddd, J=10.4, 8.1, 2.2 Hz, 1H), 4.52 (d, J=5.7 Hz, 2H), 3.51 (t, J=5.3 Hz, 2H), 3.41 (dt, J=7.5, 5.7 Hz, 4H), 2.76-2.73 (m, 2H), 1.92-1.86 (m, 2H). ESI-MS m/z: 449.1 (MH$^+$). HRMS calcd $C_{21}H_{23}F_2N_4O_5$[MH$^+$], 449.1631; found, 449.1631.

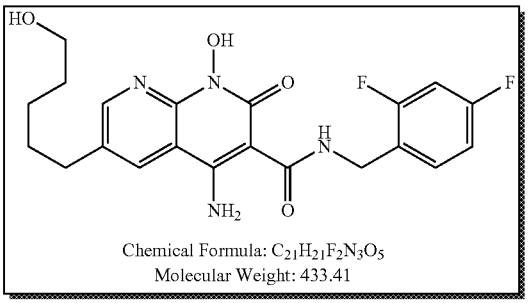

Chemical Formula: $C_{21}H_{21}F_2N_3O_5$
Molecular Weight: 433.41

N-(2,4-Difluorobenzyl)-1,4-dihydroxy-6-(5-hydroxypentyl)-2-oxo-1,2-dihydro-1,8-naphthyridine-3-carboxamide (XZ421)

According to general procedure E, the title compound was prepared in 86% yield from 1-(benzyloxy)-N-(2,4-difluorobenzyl)-4-hydroxy-6-(5-hydroxypent-1-yn-1-yl)-2-oxo-1,2-dihydro-1,8-naphthyridine-3-carboxamide (9l) after purification by preparative HPLC (with a linear gradient of 30% B to 70% B over 30 minutes; retention time=23.8 minutes). $^1$H NMR (500 MHz, DMSO-$d_6$) δ 10.96 (bs, 1H), 10.52 (t, J=6.1 Hz, 1H), 8.70 (d, J=2.0 Hz, 1H), 8.26 (d, J=2.0 Hz, 1H), 7.48 (dd, J=15.3, 8.6 Hz, 1H), 7.30-7.25 (m, 1H), 7.09 (td, J=8.5, 2.5 Hz, 1H), 4.63 (d, J=5.9 Hz, 2H), 3.37 (t, J=6.5 Hz, 2H), 2.73 (t, J=7.6 Hz, 2H), 1.65-1.59 (m, 2H), 1.46-1.42 (m, 2H), 1.35-1.28 (m, 2H). ESI-MS m/z: 434.1 (MH$^+$). HRMS calcd $C_{21}H_{22}F_2N_3O_5$ [MH$^+$], 434.1522; found, 434.1507.

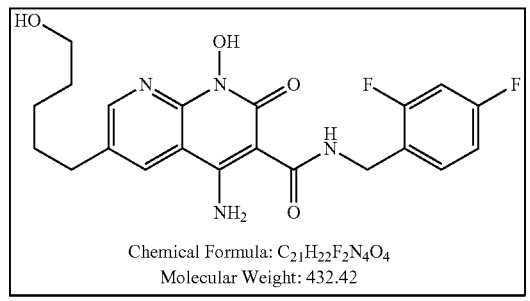 [SMILES: Nc1c(C(=O)NCc2ccc(F)cc2F)c(=O)n(O)c2ncc(CCCCCO)cc12]

Chemical Formula: $C_{21}H_{22}F_2N_4O_4$
Molecular Weight: 432.42

4-Amino-N-(2,4-difluorobenzyl)-1-hydroxy-6-(5-hydroxypentyl)-2-oxo-1,2-dihydro-1,8-naphthyridine-3-carboxamide (XZ419)

According to general procedure E, the title compound was prepared in 75% yield from 4-amino-1-(benzyloxy)-N-(2,4-difluorobenzyl)-6-(5-hydroxypent-1-yn-1-yl)-2-oxo-1,2-dihydro-1,8-naphthyridine-3-carboxamide (10l) after purification by preparative HPLC (with a linear gradient of 30% B to 60% B over 30 minutes; retention time=19.8 minutes). $^1$H NMR (500 MHz, DMSO-$d_6$) δ 10.70 (t, J=5.8 Hz, 1H), 8.58 (d, J=1.8 Hz, 1H), 8.54 (d, J=1.8 Hz, 1H), 7.42 (dd, J=15.4, 8.7 Hz, 1H), 7.24 (ddd, J=10.6, 9.4, 2.6 Hz, 1H), 7.09-7.05 (m, 1H), 4.52 (d, J=5.8 Hz, 2H), 3.39 (t, J=6.5 Hz, 2H), 2.68 (t, J=7.6 Hz, 2H), 1.68-1.62 (m, 2H), 1.49-1.43 (m, 2H), 1.36-1.30 (m, 2H). ESI-MS m/z: 433.2 (MH$^+$). HRMS calcd $C_{21}H_{23}F_2N_4O_4$[MH$^+$], 433.1682; found, 433.1667.

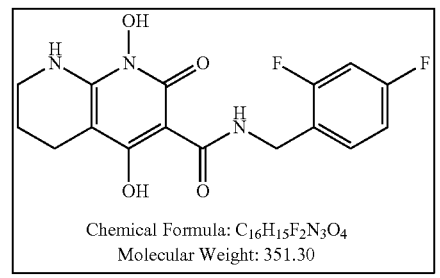 [SMILES: O=C(NCc1ccc(F)cc1F)c1c(O)c2c(n(O)c1=O)NCCC2]

Chemical Formula: $C_{16}H_{15}F_2N_3O_4$
Molecular Weight: 351.30

N-(2,4-Difluorobenzyl)-1,4-dihydroxy-2-oxo-1,2,5,6,7,8-hexahydro-1,8-naphthyridine-3-carboxamide (XZ422)

Purification by preparative HPLC (as indicated in the General Synthetic Procedures using a 00G-4436-P0-AX column with a linear gradient of 30% B to 80% B over 30 minutes; retention time=23.1 minutes), fluffy solid XZ422 was afforded. $^1$H NMR (500 MHz, DMSO-$d_6$) δ 11.10 (bs, 1H), 10.19 (t, J=6.0 Hz, 1H), 7.72 (s, 1H), 7.39 (dd, J=15.0, 8.0 Hz, 1H), 7.26-7.22 (m, 1H), 7.09-7.05 (m, 1H), 4.50 (d, J=6.5 Hz, 2H), 3.27 (bs, 2H), 2.40 (t, J=6.5 Hz, 2H), 1.72 (d, J=5.5 Hz, 2H). ESI-MS m/z: 352.1 (M+H$^+$). HRMS calcd $C_6H_{16}F_2N_3O_4$ [MH$^+$], 352.1103; found, 352.1100.

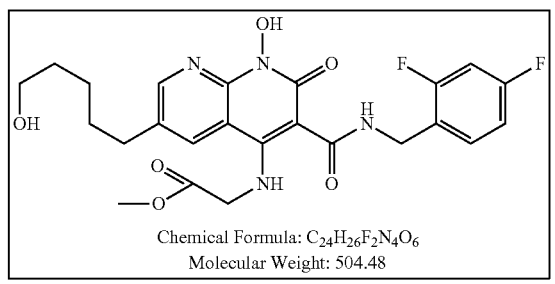 [SMILES: COC(=O)CNc1c(C(=O)NCc2ccc(F)cc2F)c(=O)n(O)c2ncc(CCCCCO)cc12]

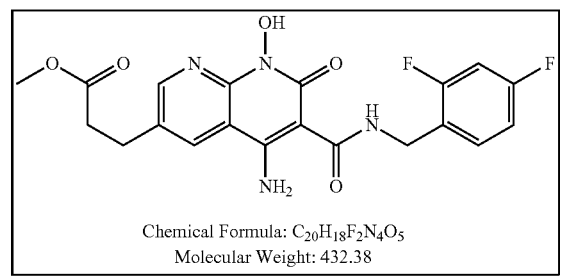

Methyl 2-((3-((2,4-difluorobenzyl)carbamoyl)-1-hydroxy-6-(5-hydroxypentyl)-2-oxo-1,2-dihydro-1,8-naphthyridin-4-yl)amino)acetate (XZ431)

According to general procedure E, the title compound was prepared in 82% yield from methyl 2-((1-(benzyloxy)-3-((2,4-difluorobenzyl)carbamoyl)-6-(5-hydroxypent-1-yn-1-yl)-2-oxo-1,2-dihydro-1,8-naphthyridin-4-yl)amino)acetate (9m) after purification by preparative HPLC (with a linear gradient of 30% B to 60% B over 30 minutes; retention time=20.5 minutes). $^1$H NMR (500 MHz, DMSO-$d_6$) δ 10.22 (bs, 1H), 10.05 (bs, 1H), 8.48 (s, 1H), 8.22 (s, 1H), 7.52 (dd, J=15.6, 8.6 Hz, 1H), 7.24-7.11 (m, 1H), 7.00 (t, J=8.5 Hz, 1H), 4.41 (t, J=5.5 Hz, 4H), 3.59 (s, 3H), 3.32 (t, J=6.5 Hz, 4H), 2.62 (t, J=7.6 Hz, 2H), 1.61-1.47 (m, 2H), 1.45-1.33 (m, 2H), 1.32-1.18 (m, 2H). ESI-MS m/z: 505.2 (MH$^+$). HRMS calcd $C_{24}H_{27}F_2N_4O_6$ [MH$^+$], 505.1893; found, 505.1889.

Methyl 3-(5-amino-6-((2,4-difluorobenzyl)carbamoyl)-8-hydroxy-7-oxo-7,8-dihydro-1,8-naphthyridin-3-yl)propanoate (XZ434)

According to general procedure E, the title compound was prepared 72% yield from (E)-methyl 3-(5-amino-8-(benzyloxy)-6-((2,4-difluorobenzyl)carbamoyl)-7-oxo-7,8-dihydro-1,8-naphthyridin-3-yl)acrylate (10m) after purification by preparative HPLC (with a linear gradient of 30% B to 65% B over 30 minutes; retention time=23.4 minutes). $^1$H NMR (500 MHz, DMSO-$d_6$) δ 10.68 (t, J=5.8 Hz, 1H), 8.62 (d, J=1.4 Hz, 1H), 8.58 (s, 1H), 7.42 (dd, J=15.3, 8.6 Hz, 1H), 7.26-7.22 (m, 1H), 7.07 (t, J=8.5 Hz, 1H), 4.51 (d, J=5.8 Hz, 2H), 3.58 (s, 3H), 2.95 (t, J=7.5 Hz, 2H), 2.77 (t, J=7.6 Hz, 2H). ESI-MS m/z: 433.1 (MH$^+$). HRMS calcd $C_{20}H_{19}F_2N_4O_5$[MH$^+$], 433.1318; found, 433.1311.

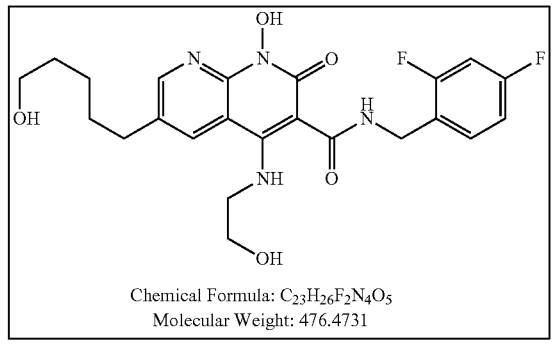 [SMILES: O=C(NCc1ccc(F)cc1F)c1c(NCCO)c2cc(CCCCCO)cnc2n(O)c1=O]

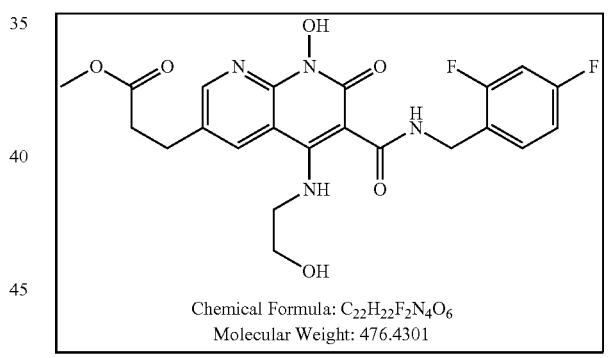

N-(2,4-Difluorobenzyl)-1-hydroxy-4-((2-hydroxyethyl)amino)-6-(5-hydroxypentyl)-2-oxo-1,2-dihydro-1,8-naphthyridine-3-carboxamide (XZ437)

According to general procedure E, the title compound was prepared in 22% yield from 1-(benzyloxy)-N-(2,4-difluorobenzyl)-4-((2-hydroxyethyl)amino)-6-(5-hydroxypent-1-yn-1-yl)-2-oxo-1,2-dihydro-1,8-naphthyridine-3-carboxamide (9n) after purification by preparative HPLC (with a linear gradient of 25% B to 40% B over 30 minutes; retention time=24.5 minutes). $^1$H NMR (500 MHz, DMSO-$d_6$) δ 10.98 (s, 1H), 10.52 (s, 1H), 8.54 (s, 1H), 8.37 (s, 1H), 7.50-7.47 (m, 1H), 7.24 (t, J=10.0 Hz, 1H), 7.07 (t, J=8.4 Hz, 1H), 4.50 (d, J=5.6 Hz, 2H), 3.70 (bs, 2H), 3.61 (bs, 2H), 3.38 (t, J=6.5 Hz, 2H), 2.69 (t, J=7.4 Hz, 2H), 1.63-1.60 (m, 2H), 1.46-1.44 (m, 2H), 1.33-1.24 (m, 2H). ESI-MS m/z: 477.2 (MH$^+$). HRMS calcd $C_{23}H_{26}F_2N_4O_5$[MH$^+$], 477.1944; found, 477.1944.

Methyl 3-(6-((2,4-difluorobenzyl)carbamoyl)-8-hydroxy-5-((2-hydroxyethyl)amino)-7-oxo-7,8-dihydro-1,8-naphthyridin-3-yl)propanoate (XZ438)

According to general procedure E, the title compound was prepared in 20% yield from (E)-methyl 3-(8-(benzyloxy)-6-((2,4-difluorobenzyl)carbamoyl)-5-((2-hydroxyethyl)amino)-7-oxo-7,8-dihydro-1,8-naphthyridin-3-yl)acrylate (9o) after purification by preparative HPLC (with a linear gradient of 30% B to 50% B over 30 minutes; retention time=21.0 minutes). $^1$H NMR (500 MHz, DMSO-$d_6$) δ 11.09 (bs, 1H), 10.54 (t, J=5.7 Hz, 1H), 8.57 (d, J=1.8 Hz, 1H), 8.43 (d, J=1.7 Hz, 1H), 7.46 (dd, J=15.4, 8.6 Hz, 1H), 7.26-7.21 (m, 1H), 7.09-7.05 (m, 1H), 4.50 (d, J=5.7 Hz, 2H), 3.71 (s, 2H), 3.61 (t, J=5.1 Hz, 2H), 3.58 (s, 3H), 2.96 (t, J=7.4 Hz, 2H), 2.73 (t, J=7.4 Hz, 2H). ESI-MS m/z: 477.1

(MH⁺). HRMS calcd C₂₃H₂₆F₂N₄O₅[MH⁺], 477.1580; found, 477.1581.

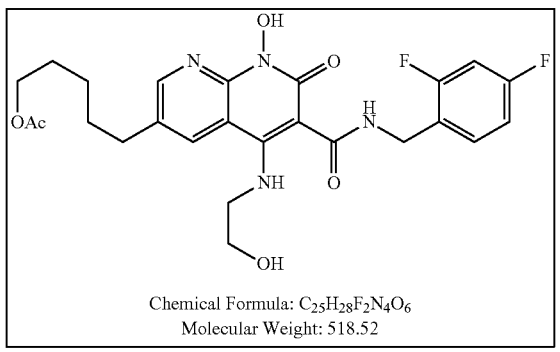 [SMILES: CC(=O)OCCCCCc1cnc2c(c1)c(NCCO)c(C(=O)NCc1ccc(F)cc1F)c(=O)n2O]

Chemical Formula: C₂₅H₂₈F₂N₄O₆
Molecular Weight: 518.52

5-(6-((2,4-Difluorobenzyl)carbamoyl)-8-hydroxy-5-((2-hydroxyethyl)amino)-7-oxo-7,8-dihydro-1,8-naphthyridin-3-yl)pentyl acetate (XZ439)

Purification by preparative HPLC (with a linear gradient of 30% B to 55% B over 30 minutes; retention time=24.1 minutes). ¹H NMR (500 MHz, DMSO-d₆) δ 10.56 (brs, 1H), 10.29 (brs, 1H), 8.53 (s, 1H), 8.30 (s, 1H), 7.53-7.48 (m, 1H), 7.22 (t, J=9.9 Hz, 1H), 7.07-7.03 (m, 1H), 4.48 (d, J=5.8 Hz, 2H), 4.17-4.15 (m, 2H), 3.81 (d, J=4.5 Hz, 2H), 3.38-3.36 (m, 2H), 2.68 (t, J=7.4 Hz, 2H), 1.97 (s, 3H), 1.64-1.57 (m, 2H), 1.47-1.41 (m, 2H), 1.33-1.29 (m, 2H). ESI-MS m/z: 519.2 (MH⁺), 541.1 (MNa⁺).

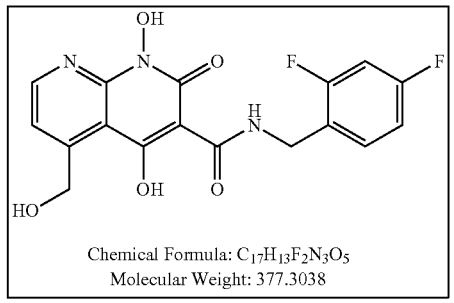 [SMILES: O=C(NCc1ccc(F)cc1F)c1c(O)c2c(CO)ccnc2n(O)c1=O]

Chemical Formula: C₁₇H₁₃F₂N₃O₅
Molecular Weight: 377.3038

N-(2,4-Difluorobenzyl)-1,4-dihydroxy-5-(hydroxymethyl)-2-oxo-1,2-dihydro-1,8-naphthyridine-3-carboxamide (XZ440)

Purification by preparative HPLC (with a linear gradient of 30% B to 60% B over 30 minutes; retention time=20.3 minutes). ¹H NMR (500 MHz, DMSO-d₆) δ 10.91 (brs, 1H), 10.63 (brs, 1H), 8.75 (d, J=5.0 Hz, 1H), 7.65 (d, J=4.9 Hz, 1H), 7.46 (dd, J=15.3, 8.5 Hz, 1H), 7.28-7.24 (m, 1H), 7.08 (t, J=8.6 Hz, 1H), 5.09 (s, 2H), 4.62 (d, J=6.0 Hz, 2H). ESI-MS m/z: 378.1 (MH⁺).

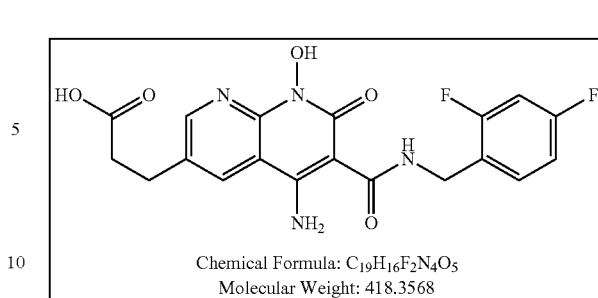

Chemical Formula: C₁₉H₁₆F₂N₄O₅
Molecular Weight: 418.3568

3-(5-Amino-6-((2,4-difluorobenzyl)carbamoyl)-8-hydroxy-7-oxo-7,8-dihydro-1,8-naphthyridin-3-yl)propanoic acid (XZ444)

Purification by preparative HPLC (with a linear gradient of 30% B to 50% B over 30 minutes; retention time=19.5 minutes). ¹H NMR (400 MHz, DMSO-d₆) δ 10.63 (t, J=5.4 Hz, 1H), 8.68-8.66 (m, 1H), 8.63-8.60 (m, 1H), 8.57 (d, J=1.9 Hz, 1H), 8.53 (d, J=1.9 Hz, 1H), 7.40-7.34 (m, 1H), 7.21-7.16 (m, 1H), 7.04-6.99 (m, 1H), 4.47 (d, J=5.5 Hz, 2H), 2.87 (t, J=7.5 Hz, 2H), 2.62 (t, J=7.6 Hz, 2H). ESI-MS m/z: 419.1 (MH⁺). HRMS cacld. for C₁₉H₁₇F₂N₄O₅(MH⁺): 419.1162; Found: 419.1147.

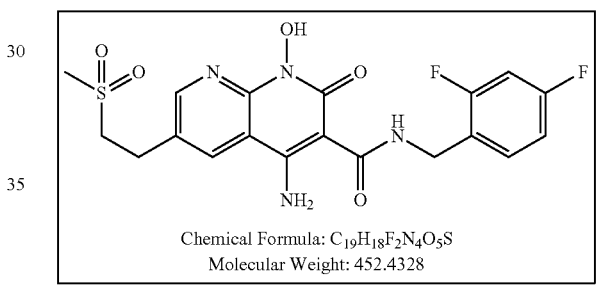

Chemical Formula: C₁₉H₁₈F₂N₄O₅S
Molecular Weight: 452.4328

4-Amino-N-(2,4-difluorobenzyl)-1-hydroxy-6-(2-(methylsulfonyl)ethyl)-2-oxo-1,2-dihydro-1,8-naphthyridine-3-carboxamide (XZ445)

Purification by preparative HPLC (with a linear gradient of 30% B to 50% B over 30 minutes; retention time=20.5 minutes). ¹H NMR (400 MHz, DMSO-d₆) δ 10.67 (t, J=5.8 Hz, 1H), 8.68 (d, J=1.8 Hz, 1H), 8.65 (s, 1H), 7.43 (dd, J=15.4, 8.6 Hz, 1H), 7.28-7.22 (m, 1H), 7.10-7.05 (m, 1H), 4.53 (d, J=5.6 Hz, 2H), 3.54 (dd, J=9.6, 6.7 Hz, 2H), 3.16 (dd, J=9.6, 6.6 Hz, 2H), 3.04 (s, 3H). ESI-MS m/z: 453.1 (MH⁺). HRMS cacld. for C₁₉H₁₉F₂N₄O₅S (MH⁺): 453.1039; Found: 453.1040.

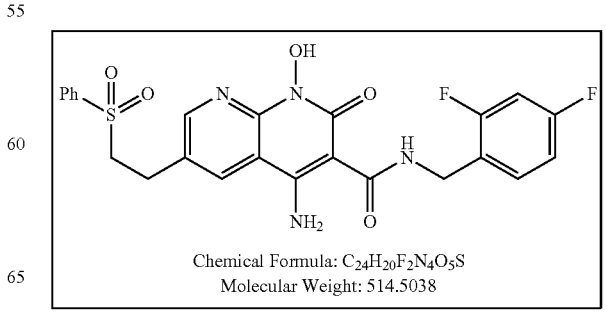

Chemical Formula: C₂₄H₂₀F₂N₄O₅S
Molecular Weight: 514.5038

4-Amino-N-(2,4-difluorobenzyl)-1-hydroxy-2-oxo-6-(2-(phenylsulfonyl)ethyl)-1,2-dihydro-1,8-naphthyridine-3-carboxamide (XZ446)

Purification by preparative HPLC (with a linear gradient of 30% B to 60% B over 30 minutes; retention time=25.5 minutes). $^1$H NMR (400 MHz, DMSO-d$_6$) δ 10.58 (t, J=5.7 Hz, 1H), 10.47 (bs, 2H), 8.52 (s, 1H), 8.43 (s, 1H), 7.83 (d, J=7.4 Hz, 2H), 7.65 (t, J=7.4 Hz, 1H), 7.57 (t, J=7.6 Hz, 2H), 7.35 (dd, J=15.4, 8.4 Hz, 1H), 7.20-7.14 (m, 1H), 7.00 (t, J=8.3 Hz, 1H), 4.44 (d, J=5.7 Hz, 2H), 3.74-3.70 (m, 2H), 2.98-2.95 (m, 2H). ESI-MS m/z: 515.1 (MH$^+$). HRMS cacld. for C$_{24}$H$_{20}$F$_2$N$_4$O$_5$S: 514.1195; Found 515.1193.

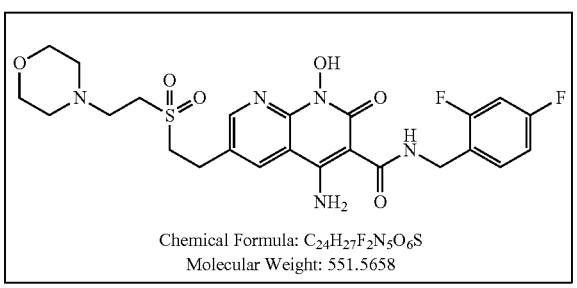 [SMILES: Nc1c(C(=O)NCc2ccc(F)cc2F)c(=O)n(O)c2ncc(CCS(=O)(=O)CCN3CCOCC3)cc12]

4-Amino-N-(2,4-difluorobenzyl)-1-hydroxy-6-(2-((2-morpholinoethyl)sulfonyl)ethyl)-2-oxo-1,2-dihydro-1,8-naphthyridine-3-carboxamide (XZ447)

Purification by preparative HPLC (with a linear gradient of 20% B to 50% B over 30 minutes; retention time=19.5 minutes). $^1$H NMR (400 MHz, DMSO-d$_6$) δ 8.66 (d, J=2.1 Hz, 1H), 8.59 (d, J=2.0 Hz, 1H), 7.42 (dd, J=15.6, 8.5 Hz, 1H), 7.22 (dd, J=14.7, 5.1 Hz, 1H), 7.06 (t, J=8.6 Hz, 1H), 4.50 (s, 2H), 3.76-3.71 (m, 4H), 33.41-3.39 (m, 4H), 3.19-3.15 (m, 4H), 3.11-3.08 (m, 4H). ESI-MS m/z: 552.2 (MH$^+$). HRMS calcd. for C$_{24}$H$_{29}$F$_2$N$_5$O$_6$S (MH$^+$): 552.1723. Found: 552.1713.

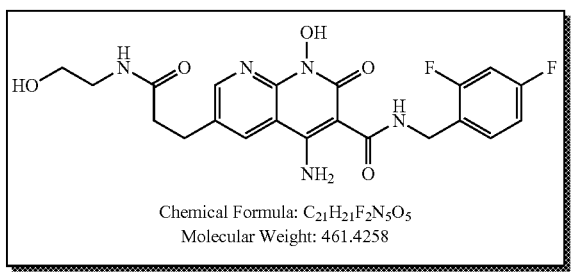

4-Amino-N-(2,4-difluorobenzyl)-1-hydroxy-6-(3-((2-hydroxyethyl)amino)-3-oxopropyl)-2-oxo-1,2-dihydro-1,8-naphthyridine-3-carboxamide Purification by preparative HPLC (with a linear gradient of 20% B to 50% B over 30 minutes; retention time=22.1 minutes). $^1$H NMR (400 MHz, DMSO-d$_6$) δ 8.56 (d, J=1.9 Hz, 1H), 8.49 (d, J=1.8 Hz, 1H), 7.42 (dd, J=15.4, 8.6 Hz, 1H), 7.25-7.19 (m, 1H), 7.06 (dd, J=9.4, 7.7 Hz, 1H), 4.50 (s, 2H), 3.32 (t, J=6.1 Hz, 2H), 3.08 (t, J=6.1 Hz, 2H), 2.92 (t, J=7.5 Hz, 2H), 2.48 (t, J=7.5 Hz, 2H). ESI-MS m/z: 462.1 (MH$^+$), 484.1 (MNa$^+$).

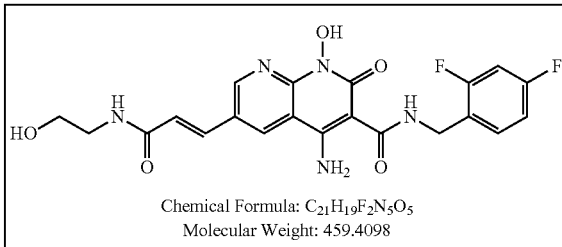

(E)-4-Amino-N-(2,4-difluorobenzyl)-1-hydroxy-6-(3-((2-hydroxyethyl)amino)-3-oxoprop-1-en-1-yl)-2-oxo-1,2-dihydro-1,8-naphthyridine-3-carboxamide Purification by preparative HPLC (with a linear gradient of 20% B to 50% B over 30 minutes; retention time=23.9 minutes). $^1$H NMR (400 MHz, DMSO-d$_6$) δ 10.63 (s, 1H), 10.53 (t, J=5.8 Hz, 1H), 8.85 (s, 1H), 8.83 (s, 1H), 8.09 (t, J=5.8 Hz, 1H), 7.43 (d, J=15.8 Hz, 1H), 7.36 (dd, J=15.4, 8.6 Hz, 1H), 7.20-7.15 (m, 1H), 7.03-6.98 (m, 1H), 6.73 (d, J=15.9 Hz, 1H), 4.65 (brs, 1H), 4.46 (d, J=5.6 Hz, 2H), 3.40 (brs, 2H), 3.20 (dd, J=11.9, 6.0 Hz, 2H). ESI-MS m/z: 460.1 (MH$^+$), 482.1 (MNa$^+$).

4-Amino-N-(2,4-difluorobenzyl)-6-(3-(dimethylamino)-3-oxopropyl)-1-hydroxy-2-oxo-1,2-dihydro-1,8-naphthyridine-3-carboxamide Purification by preparative HPLC (with a linear gradient of 30% B to 45% B over 30 minutes; retention time=20.7 minutes). $^1$H NMR (400 MHz, DMSO-d$_6$) δ 10.62 (t, J=5.8 Hz, 1H), 10.46 (brs, 1H), 8.56 (d, J=1.8 Hz, 1H), 8.50 (d, J=1.8 Hz, 1H), 7.36 (dd, J=15.4, 8.6 Hz, 1H), 7.20-7.14 (m, 1H), 7.00 (td, J=8.6, 1.9 Hz, 1H), 4.45 (d, J=5.7 Hz, 2H), 2.90 (s, 3H), 2.84 (t, J=7.4 Hz, 2H), 2.74 (s, 3H), 2.65 (t, J=7.5 Hz, 2H). ESI-MS m/z: 446.2 (MH$^+$).

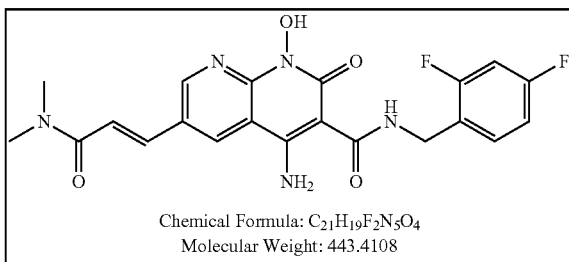

(E)-4-Amino-N-(2,4-difluorobenzyl)-6-(3-(dimethylamino)-3-oxoprop-1-en-1-yl)-1-hydroxy-2-oxo-1,2-dihydro-1,8-naphthyridine-3-carboxamide Purification by preparative HPLC (with a linear gradient of 30% B to 45% B over 30 minutes; retention time=24.1 minutes). $^1$H NMR (400 MHz, DMSO-d$_6$) δ 10.63 (s, 1H), 10.53 (t, J=5.8 Hz, 1H), 8.94 (s, 2H), 7.49 (d, J=15.4 Hz, 1H), 7.37 (dd, J=12.2, 5.3 Hz, 1H), 7.31 (d, J=15.5 Hz, 1H), 7.21-7.15 (m, 1H), 7.01 (td, J=8.9, 2.3 Hz, 1H), 4.46 (d, J=5.7 Hz, 2H), 3.14 (s, 3H), 2.89 (s, 3H). ESI-MS m/z: 444.1 (MH$^+$).

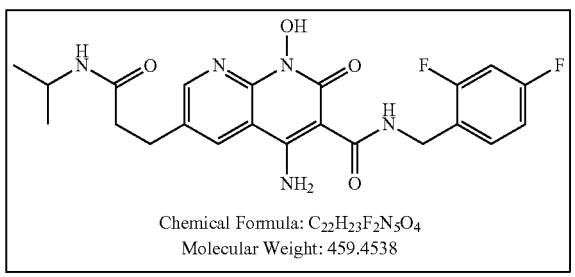 [SMILES: CC(C)NC(=O)CCc1cnc2c(c1)c(N)c(C(=O)NCc1ccc(F)cc1F)c(=O)n2O]

Chemical Formula: C$_{22}$H$_{23}$F$_2$N$_5$O$_4$
Molecular Weight: 459.4538

4-Amino-N-(2,4-difluorobenzyl)-1-hydroxy-6-(3-(isopropylamino)-3-oxopropyl)-2-oxo-1,2-dihydro-1,8-naphthyridine-3-carboxamide Purification by preparative HPLC (with a linear gradient of 30% B to 45% B over 30 minutes; retention time=23.0 minutes). $^1$H NMR (400 MHz, DMSO-d$_6$) δ 10.62 (t, J=5.7 Hz, 1H), 10.46 (brs, 1H), 8.50 (d, J=1.8 Hz, 1H), 8.47 (s, 1H), 7.61 (d, J=7.5 Hz, 1H), 7.36 (dd, J=15.4, 8.7 Hz, 1H), 7.20-7.14 (m, 1H), 7.02-6.98 (m, 1H), 4.45 (d, J=5.7 Hz, 2H), 3.76-3.68 (m, 1H), 2.84 (t, J=7.5 Hz, 2H), 2.36 (t, J=7.6 Hz, 2H), 0.90 (d, J=6.6 Hz, 6H). ESI-MS m/z: 460.2 (MH$^+$).

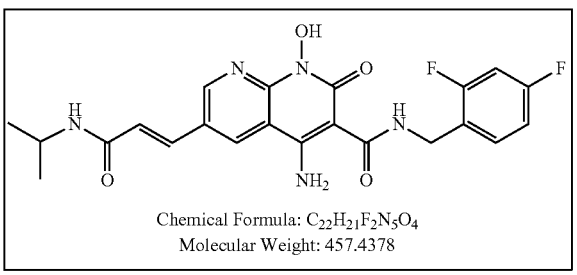 [SMILES: CC(C)NC(=O)/C=C/c1cnc2c(c1)c(N)c(C(=O)NCc1ccc(F)cc1F)c(=O)n2O]

Chemical Formula: C$_{22}$H$_{21}$F$_2$N$_5$O$_4$
Molecular Weight: 457.4378

(E)-4-Amino-N-(2,4-difluorobenzyl)-1-hydroxy-6-(3-(isopropylamino)-3-oxoprop-1-en-1-yl)-2-oxo-1,2-dihydro-1,8-naphthyridine-3-carboxamide Purification by preparative HPLC (with a linear gradient of 30% B to 45% B over 30 minutes; retention time=27.9 minutes). $^1$H NMR (400 MHz, DMSO-d$_6$) δ 10.63 (s, 1H), 10.53 (t, J=5.8 Hz, 1H), 8.84 (s, 1H), 8.82 (s, 1H), 8.01 (d, J=7.7 Hz, 1H), 7.41 (d, J=15.8 Hz, 1H), 7.37-7.33 (m, 1H), 7.20-7.15 (m, 1H), 7.00 (td, J=8.6, 2.3 Hz, 1H), 6.66 (d, J=15.9 Hz, 1H), 4.46 (d, J=5.7 Hz, 2H), 3.91 (td, J=13.3, 6.6 Hz, 1H), 1.05 (d, J=6.6 Hz, 6H). ESI-MS m/z: 458.2 (MH$^+$).

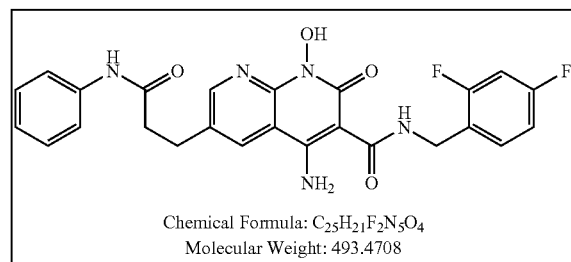

Chemical Formula: C$_{25}$H$_{21}$F$_2$N$_5$O$_4$
Molecular Weight: 493.4708

4-Amino-N-(2,4-difluorobenzyl)-1-hydroxy-2-oxo-6-(3-oxo-3-(phenylamino)propyl)-1,2-dihydro-1,8-naphthyridine-3-carboxamide

Compositions and Methods of Use

The compounds and compositions disclosed herein may be used to inhibit drug-resistant HIV-1 integrase. The compounds and compositions disclosed herein may be used for treating a subject infected with AIDS or an HIV infection. In certain embodiments, the compounds and compositions disclosed herein may be used to inhibit raltegravir-resistant HIV-1 integrase in the subject. In certain embodiments, the compounds and compositions disclosed herein may overcome resistance to raltegravir and/or evitegravir.

In certain embodiments, the compounds disclosed herein may be co-administered with at least one other anti-HIV or anti-AIDS therapeutic agent. Illustrative anti-HIV or anti-AIDS therapeutic agents include nucleoside HIV reverse transcriptase inhibitors, non-nucleoside HIV reverse transcriptase inhibitors, HIV protease inhibitors, HIV fusion inhibitors, HIV attachment inhibitors, inhibitors that block the viruses ability to interact with the co-receptors CXR4 or CCR5, HIV budding or maturation inhibitors, and HIV integrase inhibitors. Illustrative nucleoside HIV reverse transcriptase inhibitors include abacavir, didanosine, emtricitabine, lamivudine, stavudine, tenofovir, zalcitabine, and zidovudine, or a pharmaceutically acceptable salt thereof. Illustrative non-nucleoside HIV reverse transcriptase inhibitors include delavirdine, efavirenz, etravirine, rilpivirine and nevirapine, or a pharmaceutically acceptable thereof. Illustrative HIV protease inhibitors include amprenavir, atazanavir, indinavir, lopinavir, nelfinavir, ritonavir, saquinavir and fosamprenavir, or a pharmaceutically acceptable salt thereof. Illustrative HIV fusion inhibitors include enfuvirtide or T-1249, or a pharmaceutically acceptable salt thereof. Illustrative inhibitors that block the virus's ability to interact with CCR5 include Sch-C, Sch-D, TAK-220, PRO-140, and UK-427,857, or a pharmaceutically acceptable salt thereof. An illustrative inhibitor that block the virus's ability to interact with CXCR4 is AMD-3100, or a pharmaceutically acceptable salt thereof. An illustrative budding or maturation inhibitor is PA-457, or a pharmaceutically acceptable salt thereof.

Also disclosed herein is the use of a compound of formula I in the manufacture of a medicament for the treatment of AIDS or HIV infection.

Another aspect of the disclosure includes pharmaceutical compositions prepared for administration to a subject and which include a therapeutically effective amount of one or more of the compounds disclosed herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In particular, suitable salts include those derived from alkali metals such as potassium and sodium, alkaline earth metals such as calcium and magnesium, among numerous other acids well known in the pharmaceutical art.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl) amine, 2-hydroxy-tert-butylamine, tris(hydroxymethyl) methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, dog, sheep, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth.

EXAMPLES

Assay Protocols:
In Vitro Integrase Assay.
Integrase reactions were carried out by adding drugs or an equivalent volume of 100% dimethyl sulfoxide (DMSO; used as the drug solvent) to a mixture of 20 nM DNA and 400 nM integrase in 50 mM morpholinepropanesulfonic acid (pH 7.2), 7.5 mM $MgCl_2$, and 14 mM 2-mercaptoethanol. Reactions were performed at 37° C. for 2 h and quenched by the addition of an equal volume of loading buffer (formamide containing 1% sodium dodecyl sulfate, 0.25% bromophenol blue, and xylene cyanol). Reaction products were separated in 16% polyacrylamide denaturing sequencing gels. Dried gels were visualized using a Typhoon 8600 (GE Healthcare, Piscataway, N.J.). Densitometric analyses were performed using ImageQuant 5.1 software from GE Healthcare. The data analyses (linear regression, 50% inhibitory concentration [$IC_{50}$] determination, standard deviation [SD]) were performed from at least 3 independent determination using Prism 5.0c software from GraphPad.

Cellular Cytotoxicity Assay.

The human osteosarcoma cell line, HOS, was obtained from Dr. Richard Schwartz (Michigan State University, East Lansing, Mich.) and grown in Dulbecco's modified Eagle's medium (Invitrogen, Carlsbad, Calif.) supplemented with 5% (v/v) fetal bovine serum, 5% newborn calf serum, and penicillin (50 units/mL) plus streptomycin (50 μg/mL; Quality Biological, Gaithersburg, Md.). On the day prior to the screen, HOS cells were seeded in a 96-well luminescence cell culture plate at a density of 4000 cells in 100 μL per well. On the day of the screen, cells were treated with compounds at the appropriate concentration range chosen and incubated at 37° C. for 48 hrs. Cytotoxicity was measured by monitoring ATP levels via a luciferase reporter assay. Cells were lysed in 50 μL cell lysis buffer (PerkinElmer, Waltham, Mass.) and shaken at 700 rpm at room temperature for 5 mins. After the addition of 50 μL of ATPlite buffer (PerkinElmer) directly onto the lysed cells and shaking at 700 rpm at room temperature for 5 mins, ATP levels were monitored by measuring luciferase activity using a microplate reader. Activity was normalized to cytotoxicity in the absence of target compounds. KaleidaGraph (Synergy Software, Reading, Pa.) was used to perform regression analysis on the data. $CC_{50}$ values were determined from the fit model.

Single-Round HIV-1 Infectivity Assay.

Human embryonyl kidney cell culture cell line 293 was acquired from the American type Culture Collection (ATCC). The human osteosarcoma cell line, HOS, was obtained from Dr. Richard Schwartz (Michigan State University, East Lansing, Mich.) and grown in Dulbecco's modified Eagle's medium (Invitrogen, Carlsbad, Calif.) supplemented with 5% (v/v) fetal bovine serum, 5% newborn calf serum, and penicillin (50 units/mL) plus streptomycin (50 μg/mL; Quality Biological, Gaithersburg, Md.). The transfection vector, pNLNgoMIVR⁻ΔLUC was made from pNLNgoMIVR⁻ΔEnv.HSA by removing the HSA reporter gene and replacing it with a luciferase reporter gene between the NotI and XhoI restriction sites (Oh et al. 2007; Zhao et al. 2008).

VSV-g-pseudotyped HIV was produced by transfections of 293 cells as mentioned previously (Julius et al. 2004). On the day prior to transfection, 293 cells were plated on 100-mm-diameter dishes at a density of $1.5 \times 10^6$ cells per plate. 293 cells were transfected with 16 μg of pNLNgoMIVR⁻ΔLUC and 4 μg of pHCMV-g (obtained from Dr. Jane Burns, University of California, San Diego) using the calcium phosphate method. At approximately 6 hrs after the calcium phosphate precipitate was added, 293 cells were washed twice with phosphate-buffered saline (PBS) and incubated with fresh media for 48 hrs. The virus-containing supernatants were then harvested, clarified by low-speed centrifugation, filtrated, and diluted for preparation in infection assays. On the day prior to the screen, HOS cells were seeded in a 96-well luminescence cell culture plate at a density of 4000 cells in 100 μL per well. On the day of the screen, cells were treated with compounds from a concentration range of 10 μM to 0.0005 M using 11 serial dilutions and then incubated at 37° C. for 3 hrs. After compound incorporation and activation in the cell, 100 μL of virus-stock diluted to achieve a maximum luciferase signal between 0.2 and 1.5 RLUs was added to each well and further incubated at 37° C. for 48 hrs. Infectivity was measured by using the Steady-lite plus luminescence reporter gene assay system (PerkinElmer, Waltham, Mass.). Luciferase activity was measured by adding 100 μL of Steady-lite plus buffer (PerkinElmer) to the cells, incubating at room temperature for 20 mins, and measuring luminescence using a microplate reader. Activity was normalized to infectivity in the absence of target compounds. KaleidaGraph (Synergy Software, Reading, Pa.) was used to perform regression analysis on the data. $EC_{50}$ values were determined from the fit model.

Vector Constructs.

pNLNgoMIVR⁻ΔEnv.LUC has been described previously (Zhao et al. 2008). The integrase codon reading frame was removed from pNLNgoMIVR⁻ΔEnv.LUC (between KpnI and SalI sites) and placed between the KpnI and SalI sites of pBluescript II KS+. Using that construct as the wild-type template, we prepared the following HIV-1 Integrase-resistant mutants via the QuikChange II XL (Stratagene, La Jolla, Calif.) site-directed mutagenesis protocol: H51Y, T66I, E92Q, G118R, Y143R, Q148H, Q148K, N155H, R263K, G140S+Q148H, G140A+Q148K, E138K+Q148K, and H51Y+R263K. The following sense with cognate antisense (not shown) oligonucleotides (Integrated DNA Technologies, Coralville, Iowa) were used in the mutagenesis: H51Y, 5'-CTAAAAGGGGAAGCCATG-TATGGACAAGTAGACTGTA-3'; T66I, 5'-CCAG-GAATATGGCAGCTAGATTGTATACATTTA-GAAGGAAAAGTT-3'; E92Q, 5'-GCAGAAGTAATTCCAGCACAGACA-GGGCAAGAAA-3'; G118R, 5'-GTACATACAGA-CAATCGCAGCAATTTCACCAGTAC-3'; E138K, 5'-GGCGGGGATCAAGCAGAAATTTGGCATTCCCTA-3'; G140A, 5'-GGGGATCAAGCAGGAATTTGCCATTC-CCTACAATC-3'; G140S, 5'-GGGGATCAAGCAG-GAATTTAGCATTCCCTACAATC-3'; Y143R, 5'-GCAGGAATTTGGCATTCCCCGCAATC-CCCAAAGTCAAGGA-3'; Q148H, 5'-CATTCCCTA-CAATCCCCAAAGTCATGGAGTAATAGAATCTA-3'; Q148K, 5'-CATTCCCTACAATCCCCAAAG-TAAAGGAGTAATAGAATCTATGAA-3'; N155H, 5'-CCAAAGTCAAGGAGTAATAGAATCTATG-CATAAAGAATTAAAGAAAATTATAGGA CA-3'; R263K 5'-AAAGTAGTGCCAAGAAAAAAAGCAAAGAT-CATC-3'. The double mutation G140S+Q148H was constructed by using the previously generated Q148H mutant and the appropriate oligonucleotide for the $2^{nd}$ mutation, G140S. The double mutation G140A+Q148K was made by using the Q148K mutant and the appropriate oligonucleotide for the $2^{nd}$ mutation, G140A. The double mutation E138K+Q148K was made by using the Q148K mutant and the appropriate oligonucleotide for the $2^{nd}$ mutation, E138K. The double mutation H51Y+R263K was constructed by using the previously generated H51Y mutant and the appropriate oligonucleotides for the $2^{nd}$ mutation, R263K. The DNA sequence of each construct was verified independently by DNA sequence determination. The mutant integrase coding sequences from pBluescript II KS+ were then subcloned into pNLNgoMIVRΔEnv.LUC (between the KpnI and SalI sites) to produce the full-length mutant HIV-1 Integrase constructs. These DNA sequences were additionally checked independently by DNA sequence determination.

TABLE 1

Inhibitory potencies of claimed compounds using an in vitro IN assay.

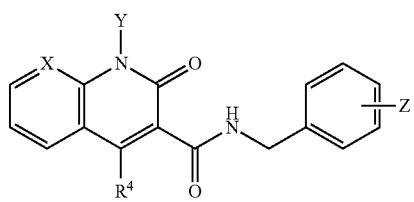

| No. | X | R⁴ | Y | Z | IC₅₀ Values (μM) 3'-Processing | Strand transfer |
|---|---|---|---|---|---|---|
| XZ370 | COCH$_3$ | H | OH | 2,4-diF | >333 | >333 |
| XZ353 | CH | H | OH | 2,4-diF | >333 | 19.7 ± 2.7 |
| XZ369 | COH | H | OH | 2,4-diF | 43 ± 5 | 18 ± 7 |
| XZ374 | COH | H | OH | 3-Cl-4-F | 17 ± 1 | 0.53 ± 0.13 |
| XZ375 | COH | H | OH | 3,4-diF | 24 ± 3 | 0.78 ± 0.22 |
| XZ365 | N | OH | OH | 3-Cl-4-F | 4.7 ± 0.7 | 0.027 ± 0.006 |
| XZ367 | N | OH | OH | 3,4-diF | 3.6 ± 0.6 | 0.040 ± 0.010 |
| XZ351 | N | OH | OH | 2,4-diF | 1.2 ± 0.2 | 0.055 ± 0.008 |
| XZ364 | N | OH | H | 4-F | 136 ± 16 | 5.1 ± 1.5 |

TABLE 1-continued

Inhibitory potencies of claimed compounds using an in vitro IN assay.

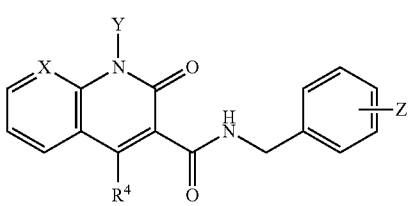

| No. | X | R⁴ | Y | Z | IC₅₀ Values (μM) 3'-Processing | Strand transfer |
|---|---|---|---|---|---|---|
| XZ366 | N | OH | H | 3-Cl-4-F | 125 ± 15 | 7.8 ± 1.1 |
| XZ368 | N | OH | H | 3,4-diF | 93 ± 8 | 8.1 ± 1.8 |
| XZ352 | N | OH | H | 2,4-diF | >333 | 7.1 ± 1.8 |
| XZ390 | N | H | OH | 2,4-diF | 6.1 ± 0.8 | 0.041 ± 0.012 |
| XZ391 | N | H | OH | 3-Cl-4-F | 9.4 ± 1.5 | 0.014 ± 0.003 |
| XZ392 | N | H | OH | 3,4-diF | 13.6 ± 1.8 | 0.017 ± 0.003 |
| XZ393 | N | H | OH | 4-F | 8.9 ± 1.0 | 0.016 ± 0.003 |

TABLE 2

Antiviral potencies of claimed compounds in cells infected with HIV-1 constructs containing wild-type or mutant IN.

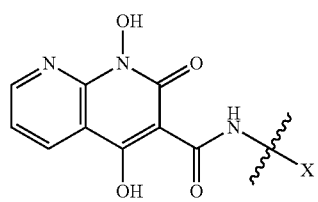

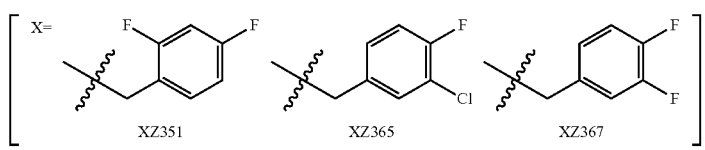

| No. | CC$_{50}$ (μM)[a] | EC$_{50}$ (μM)[b] | SI[c] | Integrase Mutants[d] Y143R | N155H | SH[e] | G118R | KK[f] |
|---|---|---|---|---|---|---|---|---|
| RAL | >100 | 0.004 | ~25,000 | 41x | 38x | 475x | 9x | 375x |
| XZ351 | 136.6 | 0.006 | 22,767 | 2x | 5x | 50x | 6x | 32x |
| XZ365 | 101.9 | 0.035 | 2,911 | 2x | 4x | 14x | — | — |
| XZ367 | 191.7 | 0.020 | 9,585 | 2x | 9x | 25x | — | — |

[a]Cytotoxic concentration resulting in 50% reduction in the level of ATP in human osteosarcoma (HOS) cells;

[b]Values obtained from cells infected with lentiviral vector harboring WT IN;

[c]Selectivity index calculated as the ratio of CC$_{50}$ to EC$_{50}$;

[d]Cells were infected with viral constructs carrying IN mutations and indicated values correspond to the fold-change in EC$_{50}$ relative to WT;

[e]G140S-Q148H double mutant;

[f]E138K-Q148K double mutant.

TABLE 3
Antiviral potencies in cells infected with HIV-1 constructs containing wild-type or mutant IN.
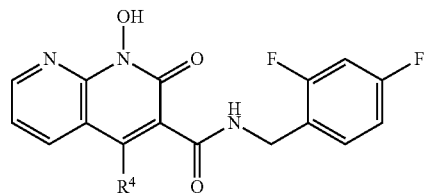
R⁴ =
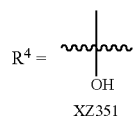
XZ351
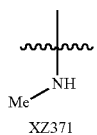
XZ371
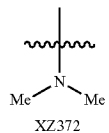
XZ372
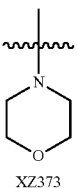
XZ373
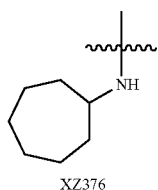 [SMILES: *NC1CCCCCC1]
XZ376
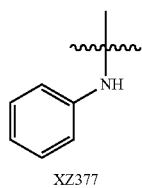 [SMILES: *Nc1ccccc1]
XZ377
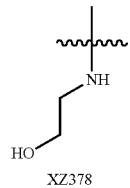
XZ378

TABLE 3-continued
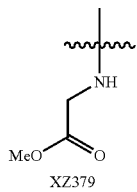
XZ379
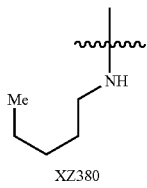 [SMILES: *NCCCCC]
XZ380
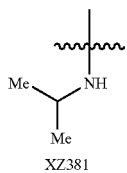
XZ381
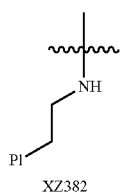
XZ382
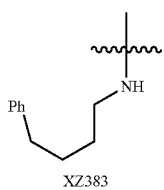 [SMILES: *NCCCCc1ccccc1]
XZ383
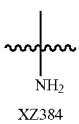
XZ384
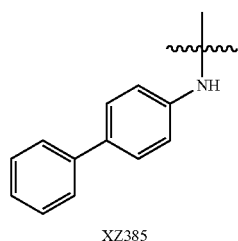 [SMILES: *Nc1ccc(-c2ccccc2)cc1]
XZ385
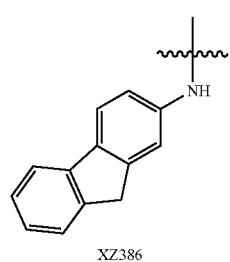 [SMILES: *Nc1ccc2c(c1)Cc1ccccc1-2]
XZ386

TABLE 3-continued
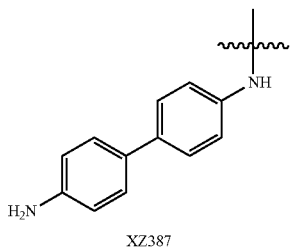 [SMILES: *Nc1ccc(-c2ccc(N)cc2)cc1]
XZ387
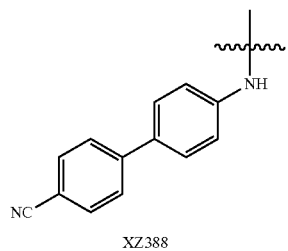 [SMILES: *Nc1ccc(-c2ccc(C#N)cc2)cc1]
XZ388
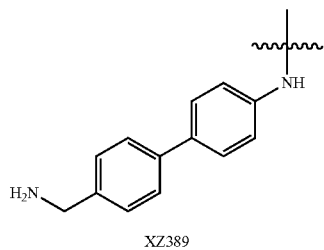 [SMILES: *Nc1ccc(-c2ccc(CN)cc2)cc1]
XZ389
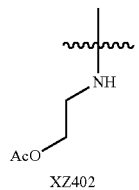 [SMILES: *NCCOC(C)=O]
XZ402
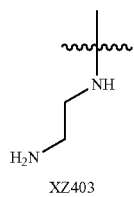 [SMILES: *NCCN]
XZ403
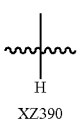
XZ390
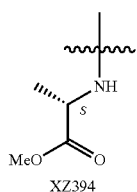
XZ394

TABLE 3-continued
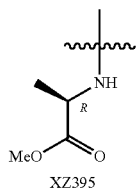
XZ395
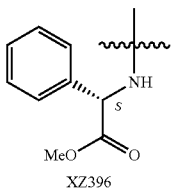
XZ396
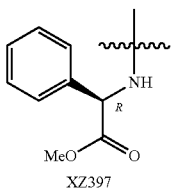
XZ397
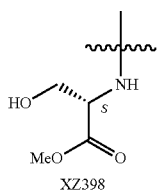
XZ398
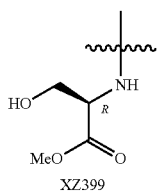
XZ399
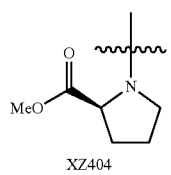 [SMILES: *N1CCC[C@H]1C(=O)OC]
XZ404
| No. | $CC_{50}$ (μM)[a] | $EC_{50}$ (nM, WT)[b] | $EC_{50}$ (nM, IN Mutants[c]) | | | SI[e] |
|---|---|---|---|---|---|---|
| | | | Y143R | N155H | SH[d] | |
| XZ 351 | 136.6 ± 20.1 | 6.2 ± 2.9 | 11.3 ± 1.93 | 30.5 ± 7.76 | 307.9 ± 125 | 22,032 |
| XZ 365 | 101.9 ± 17.8 | 34.9 ± 12.3 | 53.6 ± 9.2 | 147.6 ± 8.3 | 489.3 ± 61.8 | 2,920 |
| XZ 367 | 191.7 ± 19 | 20 ± 6.2 | 44.5 ± 12.2 | 189 ± 70.1 | 507.3 ± 124.7 | 9,585 |
| XZ 371 | >250 | 3.1 ± 0.6 | 6.1 ± 2.5 | 18.1 ± 5.2 | 87.4 ± 10.8 | 80,645 |
| XZ 372 | 13 ± 1.8 | 267.8 ± 8.03 | 273.3 ± 51.7 | 2300 ± 700 | 6800 ± 0.4 | 49 |
| XZ 373 | 8.4 ± 3.2 | 1200 ± 260 | 1800 ± 870 | 3730 ± 920 | 6920 ± 2 | 7 |
| XZ 376 | 68.7 ± 8.7 | 12.2 ± 2.9 | 6.6 ± 1.7 | 13.7 ± 3.8 | 35 ± 11.7 | 4,804 |
| XZ 377 | >250 | 14.2 ± 1.9 | 24.9 ± 6.4 | 110.1 ± 17.2 | 441 M ± 49.4 | >17,857 |
| XZ 378 | 23.5 ± 3 | 5.2 ± 0.6 | 4.6 ± 1.8 | 24.6 ± 3.8 | 43.1 ± 15.3 | 4,519 |
| XZ 379 | >250 | 3.8 ± 1.2 | 4.6 ± 2.2 | 19 ± 6.9 | 35.5 ± 15.9 | >25,000 |
| XZ 380 | 94.2 ± 24.4 | 7.4 ± 1.4 | 8.8 ± 2.7 | 12.2 ± 4.5 | 70.7 ± 0.14 | 13,457 |
| XZ 381 | >250 | 7.2 ± 3 | 7.4 ± 0.5 | 43.8 ± 6.7 | 154.4 ± 16.4 | >25,000 |
| XZ 382 | >250 | 14.1 ± 7.9 | 17.9 ± 2.6 | 78.8 ± 5.2 | 118.8 ± 3.4 | >17,857 |
| XZ 383 | 102 ± 8 | 49.9 ± 13 | 39.9 ± 14.7 | 115.9 ± 21.9 | 242.6 ± 38.7 | 2,040 |
| XZ 384 | >250 | 1.1 ± .66 | 2.5 ± 0.56 | 5.3 ± 2.3 | 35.1 ± 9.1 | >25,000 |
| XZ 385 | >250 | 371.6 ± 63 | 361.3 ± 84 | N/A | N/A | >673 |
| XZ 386 | >250 | 170.9 ± 56.8 | 448.3 ± 28.1 | N/A | N/A | >1,462 |

TABLE 3-continued

| | | | | | | |
|---|---|---|---|---|---|---|
| XZ 387 | >250 | 6.3 ± 2.4 | 101.8 ± 1.4 | 423 ± 167.7 | N/A | >25,000 |
| XZ 388 | >250 | 122.6 ± 20.7 | 345.9 ± 38.3 | N/A | N/A | >2,033 |
| XZ 389 | 0.414 | 411.2 ± 30 | N/A | N/A | N/A | N/A |
| XZ 390 | >250 | 5.1 ± 1.9 | 4.9 ± 0.77 | 134.3 ± 23 | 438.2 ± 121.2 | >25,000 |
| XZ 391 | >250 | 37.5 ± 14.5 | 33.9 ± 5.5 | 90.3 ± 5.6 | N/A | >6,667 |
| XZ 392 | >250 | 61.6 ± 13.8 | 39.7 ± 12.5 | 2200 ± 061 | N/A | >4,058 |
| XZ 393 | >250 | 25.1 ± 9.4 | 24.1 ± 5.3 | 268.1 ± 89 | N/A | >9,960 |
| XZ 394 | >250 | 4.2 ± 1.6 | 4.8 ± 1.4 | 15.3 ± 3.3 | 140.6 ± 19.7 | >25,000 |
| XZ 395 | >250 | 11.3 ± 4.7 | 8.1 ± 1.7 | 27 ± 9.9 | 89.3 ± 26.3 | >22,727 |
| XZ 396 | >250 | 9 ± 2.4 | 8.5 ± 1.9 | 17.6 ± 6.4 | 55.6 ± 6.2 | >25,000 |
| XZ 397 | >250 | 7.4 ± 3.3 | 8.2 ± 1.8 | 21.6 ± 3.7 | 48 ± 11.9 | >25,000 |
| XZ 398 | >250 | 9.7 ± 3 | 11 ± 3.7 | 29.4 ± 7.7 | 122.4 ± 32.5 | >25,000 |
| XZ 399 | >250 | 14.2 ± 3.71 | 10.2 ± 1.4 | 71.1 ± 5 | 283.5 ± 120 | >17605 |
| XZ 402 | >250 | 4.5 ± 1.5 | 4.8 ± 2.9 | 3.1 ± 0.3 | 35.1 ± 13.6 | >25,000 |
| XZ 403 | 9.6 ± 3.7 | 34.7 ± 10.5 | 56.9 ± 13.1 | | | 277 |
| XZ 404 | 18.2 ± 7.1 | 589.9 ± 71.8 | 1660 ± 920 | N/A | N/A | 31 |

[a]Cytotoxic concentration resulting in 50% reduction in the level of ATP in human osteosarcoma (HOS) cells;
[b]Values obtained from cells infected with lentiviral vector harboring WT IN;
[c]Cells were infected with viral constructs carrying IN mutations;
[d]G140S-Q148H double mutant;
[e]Selectivity index calculated as the ratio of $CC_{50}$ to $EC_{50}$.

TABLE 4

Inhibitory potencies of claimed compounds using an in vitro IN assay.

| No | $IC_{50}$ (3'-Processing, μM) | $IC_{50}$ (Strand Transfer, μM) |
|---|---|---|
| XZ371 | 3.7 ± 0.4 | 0.027 ± 0.004 |
| XZ372 | 21 ± 2 | 0.087 ± 0.012 |
| XZ373 | 77 ± 12 | 0.079 ± 0.013 |
| XZ376 | 13.1 ± 1.1 | 0.46 ± 0.18 |
| XZ377 | 6.9 ± 1.1 | 0.018 ± 0.006 |
| XZ378 | 0.55 ± 0.07 | 0.010 ± 0.009 |
| XZ379 | 0.71 ± 0.10 | 0.021 ± 0.011 |
| XZ380 | 8.2 ± 1.6 | 0.024 ± 0.009 |
| XZ381 | 1.8 ± 0.2 | 0.016 ± 0.004 |
| XZ382 | 8.0 ± 1.5 | 0.050 ± 0.012 |
| XZ383 | 12.2 ± 2.0 | 0.28 ± 0.11 |
| XZ384 | 2.5 ± 0.3 | 0.019 ± 0.002 |
| XZ385 | 52 ± 5 | 0.34 ± 0.08 |
| XZ386 | 46 ± 8 | 0.84 ± 0.21 |
| XZ387 | 80 ± 11 | 0.13 ± 0.02 |
| XZ388 | 70 ± 7 | 0.13 ± 0.03 |
| XZ389 | >333 | 29 ± 13 |
| XZ394 | 7.4 ± 0.8 | 0.017 ± 0.002 |
| XZ395 | 5.8 ± 0.6 | 0.027 ± 0.005 |
| XZ396 | 16.7 ± 1.4 | 0.010 ± 0.002 |
| XZ397 | 13.5 ± 1.0 | 0.0082 ± 0.0015 |
| XZ398 | 5.8 ± 0.5 | 0.0084 ± 0.0032 |
| XZ399 | 4.4 ± 0.5 | 0.013 ± 0.04 |
| XZ402 | 5.3 ± 0.5 | 0.027 ± 0.006 |
| XZ403 | 4.5 ± 0.2 | 0.039 ± 0.006 |
| XZ404 | 86 ± 6 | 0.31 ± 0.04 |
| XZ405 | 32 ± 4 | 0.033 ± 0.005 |
| XZ406 | 18 ± 2 | 0.011 ± 0.002 |
| XZ407 | 20 ± 2 | 0.042 ± 0.005 |
| XZ409 | >333 | 70 ± 16 |
| XZ410 | >333 | 54 ± 18 |
| XZ411 | >333 | 96 ± 40 |
| XZ412 | >333 | 1.9 ± 0.2 |
| XZ413 | >333 | 54 ± 10 |
| XZ414 | >333 | 6.2 ± 0.8 |

TABLE 5

Antiviral potencies in cells infected with HIV-1 constructs containing wild-type or mutant IN.

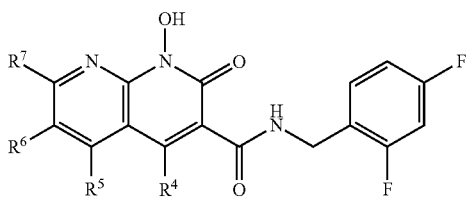

| No. | $R^4$ | $R^5$ | $R^6$ | $R^7$ |
|---|---|---|---|---|
| XZ405 | OH | H | H | $OCH_3$ |
| XZ406 | $NH_2$ | H | H | $OCH_3$ |
| XZ407 | $NHCH_2CO_2CH_3$ | H | H | $OCH_3$ |
| XZ409 | OH | H | H | Piperidine[a] |
| XZ410 | $NH_2$ | H | H | Piperidine[a] |
| XZ411 | $NHCH_2CO_2CH_3$ | H | H | Piperidine[a] |
| XZ412 | OH | H | H | Morphiline[b] |
| XZ413 | $NH_2$ | H | H | Morphiline[b] |
| XZ414 | $NHCH_2CO_2CH_3$ | H | H | Morphiline[b] |

TABLE 5-continued

[a]Piperidine:

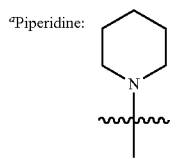 [SMILES: *N1CCCCC1]

[b]Morphiline:

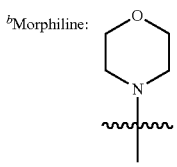 [SMILES: *N1CCOCC1]

| No. | CC$_{50}$ (μM)[a] | EC$_{50}$ (nM, WT)[b] | EC$_{50}$ (nM, IN Mutants[c]) | | | SI[e] |
|---|---|---|---|---|---|---|
| | | | Y143R | N155H | SH[d] | |
| XZ 405 | 12.1 ± 4.6 | 185.9 ± 23.2 | 214.6 ± 31 | N/A | N/A | 65 |
| XZ 406 | 2.2 ± 0.43 | 30.3 ± 9.1 | 62.2 ± 25.6 | 399.8 ± 101.2 | 3600 ± 1600 | 73 |
| XZ 407 | 11.7 ± 3.1 | 32 ± 13 | 51.5 ± 12.6 | 1260 ± 320 | N/A | 366 |

[a]Cytotoxic concentration resulting in 50% reduction in the level of ATP in human osteosarcoma (HOS) cells;
[b]Values obtained from cells infected with lentiviral vector harboring WT IN;
[c]Cells were infected with viral constructs carrying IN mutations;
[d]G140S-Q148H double mutant;
[e]Selectivity index calculated as the ratio of CC$_{50}$ to EC$_{50}$.

TABLE 6

Antiviral potencies of claimed compounds in cells infected with HIV-1 constructs containing wild-type or mutant IN.

| No. | CC$_{50}$ (μM)[a] | EC$_{50}$ (nM, WT)[b] | EC$_{50}$ (nM, IN Mutants[c]) | | | | |
|---|---|---|---|---|---|---|---|
| | | | Y143R | N155H | SH[d] | R263K | G118R |
| Raltegravir | >100 | 4 ± 2 | 162.4 ± 16.2 | 153.6 ± 32.8 | 1900 ± 300 | | |
| XZ 351 | 136.6 ± 20.1 | 6.2 ± 2.9 | 11.3 ± 1.93 | 30.5 ± 7.76 | 307.9 ± 125 | 35.9 ± 7.6 | 107.4 ± 40 |
| XZ 378 | 23.5 ± 3 | 5.2 ± 0.6 | 4.6 ± 1.8 | 24.6 ± 3.8 | 43.1 ± 15.3 | 26 | 27.3 ± 1.4 |
| XZ 379 | >250 | 3.8 ± 1.2 | 4.6 ± 2.2 | 19 ± 6.9 | 35.5 ± 15.9 | 25.9 ± 8.2 | 41.3 ± 18 |
| XZ 384 | >250 | 1.1 ± .66 | 2.5 ± 0.56 | 5.3 ± 2.3 | 35.1 ± 9.1 | 6.4 ± 2.3 | 16.1 ± 4.6 |
| XZ 402 | >250 | 4.5 ± 1.5 | 4.8 ± 2.9 | 3.1 ± 0.3 | 35.1 ± 13.6 | 16 ± 5.1 | 43.5 ± 11.2 |

[a]Cytotoxic concentration resulting in 50% reduction in the level of ATP in human osteosarcoma (HOS) cells;
[b]Values obtained from cells infected with lentiviral vector harboring WT IN;
[c]Cells were infected with viral constructs carrying IN mutations and indicated values correspond to the fold-change in EC$_{50}$ relative to WT;
[d]G140S-Q148H double mutant.

TABLE 7

Inhibitory potencies of compounds using an in vitro IN assay.

| No. | IC$_{50}$ (μM) | |
|---|---|---|
| | 3'-P | ST |
| XZ384 | 2.5 ± 0.3 | 0.019 ± 0.002 |
| XZ418 | 7.9 ± 0.8 | 0.0032 ± 0.0005 |
| XZ420 | 17.9 ± 1.6 | 0.0016 ± 0.0003 |
| XZ428 | 289 ± 49 | 3.275 ± 0.468 |
| XZ429 | 42 ± 4 | 1.982 ± 0.422 |
| XZ430 | 48 ± 4 | 0.0145 ± 0.0034 |
| XZ423 | 4.3 ± 0.6 | 0.0113 ± 0.0027 |
| XZ424 | 14.3 ± 2.1 | 0.0102 ± 0.0016 |
| XZ425 | 3.0 ± 0.4 | 0.0143 ± 0.0022 |
| XZ433 | 32 ± 6 | 0.0054 ± 0.0008 |
| XZ426 | 19 ± 1 | 0.00059 ± 0.00011 |
| XZ427 | 143 ± 14 | 3.344 ± 0.557 |
| XZ432 | 1.5 ± 0.4 | 0.0025 ± 0.0004 |
| XZ419 | 8.2 ± 1.2 | 0.0027 ± 0.0004 |
| XZ421 | 14.3 ± 1.1 | 0.0124 ± 0.0026 |
| XZ431 | 2.1 ± 0.5 | 0.0037 ± 0.0007 |
| XZ437 | 4.0 ± 0.5 | 0.0025 ± 0.0002 |
| XZ434 | 2.9 ± 0.6 | 0.0018 ± 0.0002 |
| XZ438 | 3.2 ± 0.3 | 0.0031 ± 0.0003 |

TABLE 8

Antiviral potencies of compounds in cells infected with HIV-1 constructs containing wild-type or mutant IN.

| Comp. | $CC_{50}$ (μM)[a] | $EC_{50}$ (nM, WT)[b] | $EC_{50}$ (nM, IN mutants)[c] | | | | |
|---|---|---|---|---|---|---|---|
| | | | Y143R | N155H | G140S/Q148H | G118R | R263K |
| RAL[d] | >250 | 4 ± 2 | 162.4 ± 16.2 | 153.6 ± 32.8 | 1900 ± 300 | 35.5 ± 5 | 5.7 ± 2.3 |
| EVG[d] | >250 | 6.4 ± .8 | 7.9 ± 2.3 | 90 ± 17.8 | 5700 ± 1100 | 21 ± 9.5 | 10 ± 6.2 |
| DTG[d] | >250 | 1.6 ± 0.9 | 4.3 ± 1.2 | 3.6 ± 1.3 | 5.8 ± 0.5 | 13 ± 5 | 11.3 ± 3.4 |
| XZ384 | >250 | 1.1 ± 0.66 | 2.5 ± 0.56 | 5.3 ± 2.3 | 35.1 ± 9.1 | 16.1 ± 4.6 | 6.4 ± 2.3 |
| XZ418 | >250 | 0.99 ± 0.19 | 1.95 ± 0.55 | 18.8 ± 5.9 | 112.2 ± 29.4 | — | — |
| XZ419 | >250 | 1.3 ± 0.18 | 3.0 ± 0.47 | 2.4 ± 0.8 | 6.9 ± 2.3 | 5.3 ± 1.6 | 2.6 ± 0.06 |
| XZ420 | 184 ± 23.7 | 3.4 ± .7 | 3.7 ± 1.21 | 18.7 ± 6.6 | 39.6 ± 11.3 | — | — |
| XZ421 | >250 | 23.7 ± 4.01 | 8.3 ± 1.7 | 31.6 ± 3.3 | 28.5 ± 9.5 | — | — |
| XZ423 | >250 | 3.1 ± 1.97 | 2.8 ± 0.88 | 8.5 ± 3.1 | 13.4 ± 6.5 | 10 ± 1.6 | 2.5 ± 0.82 |
| XZ424 | >250 | 1.4 ± .35 | 2.93 ± 0.9 | 5.4 ± 2.5 | 13 ± 7.6 | 5.9 ± 1.44 | 1.75 ± 0.29 |
| XZ425 | 5.0 ± 1.76 | 6.07 ± 2.1 | 7 ± 2.3 | 29.4 ± 9 | 31.7 ± 5.4 | — | — |
| XZ426 | >250 | 2.33 ± 0.6 | 2.1 ± 1.4 | 2.7 ± 0.99 | 9.4 ± 3.6 | 6.4 ± 2.5 | 8.4 ± 2.3 |
| XZ427 | 14.4 ± 4.8 | 4.8 ± 1.6 | 3.5 ± 1.2 | 5.4 ± 1.9 | 21 ± 7.8 | — | — |
| XZ428 | 27.4 ± 3.1 | 53.4 ± 13.9 | 111.5 ± 17.2 | 145.9 ± 13.7 | N/A | — | — |
| XZ429 | 12.8 ± 2.4 | 10.6 ± 2.3 | 4.7 ± 0 | 38.8 ± 9.8 | 127.7 ± 44.3 | — | — |
| XZ430 | 17.6 ± 1.6 | 5.6 ± 1.9 | 5.5 ± 2.4 | 21.1 ± 5 | 139.9 ± 33.6 | — | — |
| XZ431 | >250 | 3.3 ± 1.7 | 3.5 ± 1.6 | 11.1 ± 1.5 | 41.6 ± 1.7 | — | — |
| XZ432 | >250 | 1.6 ± .21 | 1.2 ± .58 | 4.2 ± 1.5 | 35.3 ± 3.7 | — | — |
| XZ433 | >250 | 3.7 ± 0.4 | 3.2 ± 0.8 | 6.5 ± 2.7 | 7.7 ± 1.9 | 11.1 ± 1.2 | 3.8 ± 1.1 |
| XZ434 | >250 | 0.67 ± 0.15 | 0.67 ± 0.23 | 2.3 ± 0.23 | 5.3 ± 1.8 | 4.8 ± 1.5 | 0.5 ± 0 |
| XZ437 | >250 | 13 ± 4.2 | 11.6 ± 2.1 | 15 ± 3.7 | 15.5 ± 6.8 | 23.9 ± 8.3 | 18.1 ± 1.7 |
| XZ438 | >250 | 4.1 ± 1 | 3.8 ± 1.9 | 3.9 ± 2.1 | 15.9 ± 3.5 | 4.8 ± 0.64 | 6.5 ± 0.76 |
| XZ439 | >100 | 5.3 ± 1.2 | 4.1 ± 1 | 10.3 ± 2.3 | 5.3 ± 2.1 | 14.5 ± 1.9 | 3.6 ± 0.85 |
| XZ440 | >250 | 7.3 ± 0.56 | 2.6 ± 0.4 | 14.9 ± 3.6 | 14.7 ± 1.1 | 23 ± 2.6 | 4 ± 1.4 |
| XZ444 | >250 | 1.9 ± 0.5 | 4.9 ± 1.5 | 10.3 ± 3.1 | 194.8 ± 24.6 | — | — |
| XZ445 | 95.4 ± 4.3 | 27 ± 3.2 | 27.5 ± 0.4 | 32.8 ± 6 | 117.8 ± 31.3 | — | — |
| XZ446 | >250 | 2 ± 0.1 | 0.6 ± 0.1 | 2.1 ± 1.2 | 5.2 ± 0.3 | 11.4 ± 3.5 | 5.3 ± 0.8 |
| XZ447 | >250 | 267.9 ± 68.8 | 108.6 ± 16.2 | 139.7 ± 4.9 | 412.5 ± 119.5 | — | — |

| Comp. | $EC_{50}$ (nM, IN mutants)[c] | | | |
|---|---|---|---|---|
| | T66I | E92Q | H51Y | H51Y/R263K |
| RAL[d] | 2.8 ± .4 | 29.8 ± 10.2 | 3.4 ± 0.17 | 6 ± 2.3 |
| EVG[d] | 66.2 ± .71 | 153.7 ± 34 | 4.5 ± 2.1 | 52.6 ± 18.2 |
| DTG[d] | 0.9 ± 0.8 | 2.3 ± 0.4 | 3.2 ± 0.2 | 16 ± 1.9 |
| XZ384 | 0.6 ± 0.3 | 3 ± 1.77 | 1 ± .6 | 3.2 ± 0.92 |
| XZ418 | — | — | — | — |
| XZ419 | 0.93 ± 0.24 | 3.8 ± 2.3 | 3.8 ± .6 | 2.6 ± 1.4 |
| XZ420 | — | — | — | — |
| XZ421 | — | — | — | — |
| XZ423 | 1.1 ± 0.14 | 4.8 ± 2 | 2.6 ± 0.5 | 14.7 ± 2.2 |
| XZ424 | 0.75 ± 0.07 | 1.2 ± .07 | 0.8 ± 0.24 | 3.9 ± 1.9 |
| XZ425 | — | — | — | — |
| XZ426 | 0.5 ± 0.35 | 0.74 ± 0.13 | 1.6 ± 0.14 | 5.2 ± 1.6 |
| XZ427 | — | — | — | — |
| XZ428 | — | — | — | — |
| XZ429 | — | — | — | — |
| XZ430 | — | — | — | — |
| XZ431 | — | — | — | — |
| XZ432 | — | — | — | — |
| XZ433 | 1.7 ± .52 | 2.6 ± 0.2 | 4.8 ± 1.1 | 22.4 ± 8.3 |
| XZ434 | 0.53 ± 0.06 | 2 ± 1.1 | 0.63 ± 0.3 | 2.4 ± 0.8 |
| XZ437 | 1.9 ± 0.07 | 6.5 ± 0.8 | 10.8 ± 1.4 | 30.9 ± 9.9 |
| XZ438 | 0.62 ± 0.15 | 2.7 ± 1.2 | 6.9 ± 2.9 | 2.5 ± 0.14 |
| XZ439 | 1.2 ± 0.45 | 3.8 ± 1.3 | 7.4 ± 0.85 | 15.2 ± 1.8 |
| XZ440 | 1.4 ± .5 | 4 ± 0.6 | 5 ± 0.71 | 9 ± 0.6 |
| XZ444 | — | — | — | — |
| XZ445 | — | — | — | — |
| XZ446 | — | 1.2 ± 0.6 | — | — |
| XZ447 | — | — | — | — |

[a] Cytotoxic concentration resulting in 50% reduction in the level of ATP in human osteosarcoma (HOS) cells;
[b] Values obtained from cells infected with lentiviral vector harboring WT IN;
[c] Cells were infected with viral constructs carrying IN mutations and indicated values in $EC_{50}$;
[d] FDA-approved INSTIs.

TABLE 9

XZ compounds and activities in
high growth serum assays in cells.

| Compound | $EC_{50}$ (nM, WT Normal 5%) | $EC_{50}$ (nM, WT 10% FBS) | $EC_{50}$ (nM, WT 15% FBS) |
| --- | --- | --- | --- |
| XZ379 | 3.8 ± 1.2 | 5 ± 0.5 | 1 ± 0.2 |
| XZ384 | 1.1 ± 0.66 | 0.8 ± 0.3 | 0.5 ± .05 |
| XZ402 | 4.5 ± 1.5 | 2.2 ± 0.3 | 1 ± 0.4 |
| XZ419 | 1.3 ± 0.2 | 0.93 ± 0.2 | 2.1 ± 0.4 |
| XZ426 | 2.3 ± 0.6 | 0.8 ± 0.2 | |
| XZ434 | 0.7 ± 0.2 | 0.62 ± 0.2 | 0.6 |

TABLE 10

HIV-1 IN inhibitory
potencies in assays in vitro.

| Compound | $IC_{50}$ (nM, ST) |
| --- | --- |
| XZ 440 | 14.5 ± 0.8 |
| XZ 444 | 3.9 ± 1.3 |
| XZ 445 | ~0.07 |
| XZ 446 | 3.7 ± 1.3 |
| XZ 447 | 2.5 ± 1.3 |
| DTG | 12.4 ± 2.6 |

In view of the many possible embodiments to which the principles of the disclosed compounds, compositions and methods may be applied, it should be recognized that the illustrated embodiments are only preferred examples of the invention and should not be taken as limiting the scope of the invention.

What is claimed is:

1. A method of inhibiting drug-resistant HIV-1 integrase in a subject comprising administering to a subject in need thereof a therapeutically effective amount of a compound of formula I, or a pharmaceutically acceptable salt or ester thereof, having a structure of:

wherein X is N;
Y is OH;
each of $Z^1$-$Z^5$ is independently H or halogen;
$R^4$ is H, OH, $NH_2$, $NHR^8$, $NR^8R^9$ or $R^8$;
$R^5$ and $R^7$ is each independently H, halogen, $OR^8$, $R^8$, $NHR^8$, $NR^8R^9$, $CO_2R^8$, $CONR^8R^9$, or $SO_2NR^8R^9$;
$R^6$ is halogen, optionally-substituted alkenyl, optionally-substituted alkynyl, optionally-substituted aryl, optionally-substituted cycloalkyl, optionally-substituted cycloalkylene, or optionally-substituted heterocycle; and
$R^8$ and $R^9$ is each independently H, optionally-substituted alkyl, optionally-substituted alkenyl, optionally-substituted alkynyl, optionally-substituted aryl, optionally-substituted cycloalkyl, optionally-substituted cycloalkylene, optionally-substituted heterocycle, optionally-substituted amide, optionally-substituted ester, or $R^8$ and $R^9$ together with the nitrogen to which $R^8$ and $R^9$ are attached form an optionally-substituted heterocycle.

2. The method of claim 1, wherein at least one of $Z^1$-$Z^5$ is halogen.

3. The method of claim 1, wherein at least two of $Z^1$-$Z^5$ are halogen.

4. The method of claim 1, wherein the compound is a compound of formula IV, or a pharmaceutically acceptable salt or ester thereof, having a structure of:

5. The method of claim 1, wherein $R^4$ is OH.
6. The method of claim 1, wherein $R^4$ is $NH_2$.
7. The method of claim 1, wherein $R^4$ is $NHR^8$.
8. The method of claim 1, wherein the subject has been administered at least one HIV-1 integrase inhibitor other than the compound of claim 1.
9. The method of claim 1, wherein the method comprises inhibiting raltegravir-resistant HIV-1 integrase in the subject.
10. The method of claim 1, further comprising co-administering with the compound at least one anti-HIV therapeutic agent other than the compound of claim 1.
11. A compound of formula IV, or a pharmaceutically acceptable salt or ester thereof, having a structure of:

$R^4$ is H, OH, $NH_2$, $NHR^8$, $NR^8R^9$ or $R^8$;
$R^5$ and $R^7$ is each independently H, halogen, $OR^8$, $R^8$, $NHR^8$, $NR^8R^9$, $CO_2R^8$, $CONR^8R^9$, or $SO_2NR^8R^9$;
$R^6$ is halogen, optionally-substituted alkenyl, optionally-substituted alkynyl, optionally-substituted aryl, optionally-substituted cycloalkyl, optionally-substituted cycloalkylene, optionally-substituted heterocycle, optionally-substituted amide, or optionally-substituted ester; and
$R^8$ and $R^9$ is each independently H, optionally-substituted alkyl, optionally-substituted alkenyl, optionally-substituted alkynyl, optionally-substituted aryl, optionally-substituted cycloalkyl, optionally-substituted cycloalkylene, optionally-substituted heterocycle, optionally-substituted amide, optionally-substituted ester, or $R^8$ and $R^9$ together with the nitrogen to which $R^8$ and $R^9$ are attached form an optionally-substituted heterocycle.

12. The compound of claim 11, wherein $R^4$ is OH, $NH_2$, $NHR^8$, or $R^8$.

13. A compound, or a pharmaceutically acceptable salt or ester thereof, having a structure of:

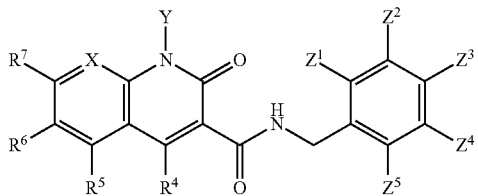

wherein X is N;
Y is OH;
each of $Z^1$-$Z^5$ is independently H or halogen;
$R^4$ is H, OH, $NH_2$, $NHR^8$, $NR^8R^9$ or $R^8$;
$R^5$ and $R^7$ is each independently H, halogen, $OR^8$, $R^8$, $NHR^8$, $NR^8R^9$, $CO_2R^8$, $CONR^8R^9$, or $SO_2NR^8R^9$;
$R^6$ is halogen, optionally-substituted alkenyl, optionally-substituted alkynyl, optionally-substituted aryl, optionally-substituted cycloalkyl, optionally-substituted cycloalkylene, or optionally-substituted heterocycle; and
$R^8$ and $R^9$ is each independently H, optionally-substituted alkyl, optionally-substituted alkylene, optionally-substituted aryl, optionally-substituted cycloalkyl, optionally-substituted cycloalkylene, optionally-substituted heterocycle, optionally-substituted amide, optionally-substituted ester, or $R^8$ and $R^9$ together with the nitrogen to which $R^8$ and $R^9$ are attached form an optionally-substituted heterocycle.

14. The compound of claim 13, wherein at least one of $Z^1$-$Z^5$ is halogen.

15. The compound of claim 13, wherein $R^4$ is $NH_2$.

16. The compound of claim 14, wherein $R^4$ is $NH_2$.

17. The method of claim 1, wherein $R^6$ is halogen, optionally-substituted alkenyl, or optionally-substituted aryl.

18. The compound of claim 11, wherein $R^6$ is halogen, optionally-substituted alkenyl, or optionally-substituted aryl.

19. The compound of claim 13, wherein $R^6$ is halogen, optionally-substituted alkenyl, or optionally-substituted aryl.

20. A method of inhibiting drug-resistant HIV-1 integrase in a subject comprising administering to a subject in need thereof a therapeutically effective amount of a compound of formula I, or a pharmaceutically acceptable salt or ester thereof, having a structure of:

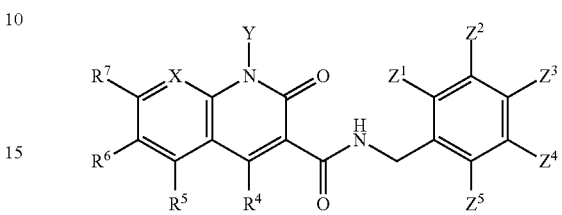

wherein X is N;
Y is OH;
each of $Z^1$-$Z^5$ is independently H or halogen, provided at least one of $Z^1$-$Z^5$ is halogen;
$R^4$ is H, OH, $NH_2$, $NHR^8$, $NR^8R^9$ or $R^8$;
$R^5$ and $R^7$ is each independently H, halogen, $OR^8$, $R^8$, $NHR^8$, $NR^8R^9$, $CO_2R^8$, $CONR^8R^9$, or $SO_2NR^8R^9$;
$R^6$ is halogen, optionally-substituted alkenyl, optionally-substituted alkynyl, optionally-substituted aryl, optionally-substituted cycloalkyl, optionally-substituted cycloalkylene, optionally-substituted heterocycle, optionally-substituted amide, or optionally-substituted ester; and
$R^8$ and $R^9$ is each independently H, optionally-substituted alkyl, optionally-substituted alkenyl, optionally-substituted alkynyl, optionally-substituted aryl, optionally-substituted cycloalkyl, optionally-substituted cycloalkylene, optionally-substituted heterocycle, optionally-substituted amide, optionally-substituted ester, or $R^8$ and $R^9$ together with the nitrogen to which $R^8$ and $R^9$ are attached form an optionally-substituted heterocycle.

21. The method of claim 20, wherein at least two of $Z^1$-$Z^5$ are halogen.

* * * * *